US007750210B2

(12) United States Patent
McGonigle et al.

(10) Patent No.: US 7,750,210 B2
(45) Date of Patent: Jul. 6, 2010

(54) COMPOSITIONS WITH INCREASED PHYTOSTEROL LEVELS OBTAINED FROM PLANTS WITH DECREASED TRITERPENE SAPONIN LEVELS

(75) Inventors: Brian McGonigle, Wilmington, DE (US); Carl A. Maxwell, Elkton, MD (US); Aideen Oonagh Hession, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 686 days.

(21) Appl. No.: 11/593,880

(22) Filed: Nov. 7, 2006

(65) Prior Publication Data

US 2007/0107081 A1    May 10, 2007

Related U.S. Application Data

(60) Provisional application No. 60/734,682, filed on Nov. 7, 2005, provisional application No. 60/760,515, filed on Jan. 19, 2006.

(51) Int. Cl.
    C12N 15/29      (2006.01)
    C12N 15/82      (2006.01)
(52) U.S. Cl. ............... 800/298; 800/281; 536/23.1; 536/23.2; 536/23.6
(58) Field of Classification Search ............ None
    See application file for complete search history.

(56) References Cited

U.S. PATENT DOCUMENTS

| 5,306,862 | A | 4/1994 | Chappell et al. |
| 5,349,126 | A | 9/1994 | Chappell et al. |
| 5,365,017 | A | 11/1994 | Chappell et al. |
| 5,589,619 | A | 12/1996 | Chappell et al. |
| 6,822,142 | B2 | 11/2004 | Karunanandaa et al. |
| 2003/0208791 | A1 | 11/2003 | Bryan et al. |

FOREIGN PATENT DOCUMENTS

| WO | 00/44909 A1 | 8/2000 |
| WO | 01/04314 A2 | 1/2001 |
| WO | WO 01/66773 * | 3/2001 |
| WO | 01/66773 A2 | 9/2001 |
| WO | 02/061072 A2 | 8/2002 |
| WO | 03/095615 A | 11/2003 |

OTHER PUBLICATIONS

Robert A. Moreau et al., Phytosterols, Phytostanols, and Their Conjugates in Foods: Structural Diversity, Quantitative Analysis, and Health-Promoting Uses, Progress in *Lipid Res.*, vol. 41:457-500, 2002.

Hong Zhang et al., Oxidosqualene Cyclases From Cell Suspension Cultures of *Betula Platyphylla Var. Japonica*: Molecular Evolution of Oxidosqualene Cyclases in Higher Plants, Biol. Pharm. Bull., vol. 26(5):642-650, 2003.
K. Haralampidis et al., A New Class of Oxidosqualene Cyclases Directs Synthesis of Antimicrobial Phytoprotectants in Monocots, PNAS, vol. 98(23):13431-13436, 2001.
Hiroaki Hayashi et al., Cloning and Characterization of a CDNA Encoding Beta-Amyrin Synthase Involved in Glycyrrhizin and Soyasaponin Biosyntheses in Licorice, Biol. Pharm. Bull. vol. 24(8):912-916, 2001.
Inaki Iturbe-Ormaetxe et al., Molecular Cloning and Characterization of Triterpene Synthases from Medicago Truncatula and Lotus Japonicus, Plant Molecular Biology, vol. 51:731-743, 2003.
Woosuk Jung et al., Identification and Expression of Isoflavone Synthase, The Key Enzyme for Biosynthesis of Isoflavones in Legumes, Nature Biotechnology, vol. 18:208-212, 2000.
Tetsuo Kushiro et al., Beta-Amyrin Synthase—Cloning of Oxidosqualene Cyclase that Catalyzes the Formation of the Most Popular Triterpene Among Higher Plants, Eur. J. Biochem., vol. 256:238-244, 1998.
Masayo Morita et al., Molecular Cloning and Functional Expression of Triterpene Synthases From Pea (Pisum Sativum), Eur. J. Biochem., vol. 267:3453-3460, 2000.
National Center for Biotechnology Information General Identifier No. 7288452, Accession No: AF195818, Mar. 23, 2000, W. Jung et al., Identification and Expression of Isoflavone Synthase, The Key Enzyme for Biosynthesis of Isoflavones in Legumes.
Hubert Schaller et al., Expression of the Hevea Brasiliensis (H.B.K.) Mull. Arg. 3-Hydroxy-3-Methylglutaryl-Coenzyme a Reductase 1 in Tobacco Results in Sterol Overproduction, Plant Physiol., vol. 109:761-770, 1995.
Mark Harker et al., Enhancement of Seed Phytosterol Levels by Expression of an N-Terminal Truncated Hevea Brasiliensis (Rubber Tree) 3-Hydroxy-3-Methylglutary 1-COA Reductase, Plant Biotechnology Journal, vol. 1(2):113-121, 2003.
Mi-Hyun Lee et al., Enhanced Triterpene and Phytosterol Biosynthesis in Panax Ginseng Overexpressing Squalene Synthase Gene, Plant and Cell Physiology, vol. 45(8):976-984, 2004.

* cited by examiner

*Primary Examiner*—Russell Kallis

(57) ABSTRACT

This invention is in the field of plant molecular biology. More specifically, this invention pertains to compositions having increased levels of at least one phytosterol, said compositions being obtained from plants or plant parts, and methods thereof. The plants may have decreased levels of triterpene saponins. The plants or plant parts may comprise at least one recombinant DNA molecule comprising a promoter operably linked to at least a portion of at least one polynucleotide from at least one oxidosqualene cyclase gene, said recombinant DNA molecule sufficient to increase the production of at least one phytosterol; or any progeny of said plant, wherein said progeny comprise said recombinant DNA molecule. Compositions, oils, as well as food and feed products obtained from or prepared with said compositions are also part of the invention.

4 Claims, 5 Drawing Sheets

US 7,750,210 B2

SEQUENCE LISTING

<160> NUMBER OF SEQ ID NOS: 32

<210> SEQ ID NO 1
<211> LENGTH: 2766
<212> TYPE: DNA
<213> ORGANISM: Glycine max
<220> FEATURE:
<221> NAME/KEY: misc_feature
<222> LOCATION: (1)..(2766)
<223> OTHER INFORMATION: cDNA insert in clone sah1c.pk002.n23

<400> SEQUENCE: 1

```
ttcatctccc acgcttcact ttctccctcc ccctccctct ccctctccct ctccccaccc      60
cgagacctca ccctcccctc cttctccctt tcgccaccac aacgcccaac gtccacataa     120
gctagatgag atcaatctga agcaaatggt tataatttca aaattttaag agtggaggac     180
ctgtgttgtg cacgttagag tgaatcgttc aagattaatc cttaacaacc tgaccaccag     240
gaacaaccag ctatcatttt acattgaact agaaattcat ttagaagatc aaagacaaaa     300
ttttccgatt aaaacgtact taaattgaag aggggttgtt ggcattgtgc accaaaaagg     360
aaaaaaaatg tggaggttaa agatagcaga tggagggaat gatccctata tatttagcac     420
aaataatttt gtggggaggc aaacatggga gtttgattct gaggcaggta ccgctgagga     480
acgagctcaa attgaagcag ctcgtcaaaa ctttttatgaa aatcgcttca tggtcaaggc     540
ttgtggtgat cgactttggc ggtttcagat tttgagggaa ataatttca aacaaacaat      600
aagtggcgta agatagaag atgatgagaa aattacatgc gagaaaatta ggagcaccat     660
gaagagggcc actcattacc tatcgtcact acagactagt gatggtcatt ggcctgctca     720
tcttggaggt tccctctttt ttactccacc gttggtcatt tgtttatata ttacaggaca     780
tattgattct atattttcag aagagtatcg taaagagatt cttcgttaca tatattacca     840
ccagaacaaa gatggaggtt ggggactaca catagaaggt cacagtatca tgttttgcac     900
tacactcaat tatatatgca tgcgaattct tggagaagga cctaatggag tcataacaa      960
tgcttgtgct aaagcaagaa agtggattca tgatcatggt ggtgcaacac atataccttc    1020
atgggggaaa ttttggcttt cggtacttgg tatagttgat tggtgtggaa gcaacccaat    1080
gccgcctgaa ttttggatcc ttccttcttt tctccctatg catccgggta aaatgtggtg    1140
ttattgtcgg ttggtataca tgcccatgtc ttatttgtat gggaagaaat ttacgggtcc    1200
aatcacaccg ttagttgtaa atttgagaga agaacttttt attcaacctt atgatgaaaa    1260
tagttggaag aaagcacgtc ataaatgtgc aaatgaagat ctttactatc cccatcattg    1320
gatacaagat ctattatggg atagtttgta tgtattcacc gagcctcttc taaattgttg    1380
gcctttcaac aagttggtta gagaaaaggc acttcaagta acaatgaaac atattcatta    1440
tgaagacgaa aatagtcggt atattgccat cgggtgtgtg gaaaaggttc tatgtatgct    1500
tgcttgttgg gttgaagatc caaatggaga tgctttcaag aagcatcttg caaggatccc    1560
agattattta tgggttttctg aagatggaat gaccatgcag ggtattggta ctcaatcatg    1620
ggatgttggt ttcattgttc aagctttact tgctactaac cttatagatg attttggacc    1680
tacaattgca aaagctcacg atttcatcaa gaaatctcag gtaagagaaa atccttcggg    1740
agattttaag agtatgtatc gtcacatttg taaaggctca tggacccttg ccgatagaga    1800
tcatgcatgg caagtttctg ataccactgc agaatgtttg aagtgttgtc tactttatc     1860
agtgctgcca caagatattg tgggagaaaa aatggaactt gaaaagttac atgattcaat    1920
caatttgata ctgtcacttc agagtaaaaa tggaggtatg actgcgtggg agcccgcagg    1980
agcttataaa tggttggaac tactcaatcc tacggaattt tttgctgaca tagtagttga    2040
gcacgaatat cttgaatgca ctgcatcagc aattcaggtt ttagtgttgt tcaaaaagct    2100
ttaccctgag catagaaagg aagagataga gaacttcatt gctaaagcag taacattcat    2160
tgaagataca caattagaga atggttcttg gtatgggaat tgggcagttt gtttcactta    2220
cagctcttgg tttgcacttg gaggtctagt tgctgctggc aagacttaca caaattgtgt    2280
tactattcgt aaagctgtga aatttctact caaaatacaa aataaggacg gtgggtgggg    2340
```

```
agagagttat ctttcttgcc caaggaagat gtacgtacct cttgaaggaa gtcgatcaaa    2400
tgttgtacaa acatcatggg ctctaatggc tctaattcat gctgagcagg ctgagagaga    2460
tccaactccc cttcatcatg cagcaaagtt actcattaat tctcagttag aagatggcga    2520
ttggccccaa caagaaactc ttggagtata cttgagaaat tgcttggttc attactcatt    2580
ctatagaaat attttccaa tgtgggcttt ggctgaatac cgcacaaatg ttttattgcc      2640
ttcctttact atttaagttg aaaaattgtg agctcaaaaa gataatgtca taccaataaa    2700
agtctagaaa aaaaaaagtt ggtaatgaag tttaataggc ttattcataa aaaaaaaaa     2760 aaaaaa                                                                2766
```

```
<210> SEQ ID NO 2
<211> LENGTH: 2478
<212> TYPE: DNA
<213> ORGANISM: Glycine max
<220> FEATURE:
<221> NAME/KEY: misc_feature
<222> LOCATION: (1)..(2478)
<223> OTHER INFORMATION: cDNA insert in clone src3c.pk024.m11

<400> SEQUENCE: 2
```

```
ggtttgtttg gtgtgagtga atagggatca gggatgtgga ggctgaagat agcagatgga      60
ggaaatgatc catacatatt cagcacaaac aatttcgttg ggaggcagac atgggagttt    120
gatcctgaag caggcagtcc agaggaacgg gcccaggttg aagcagctcg tcagcatttc    180
taccacaacc gcttcaaggt caagccctgc gctgacctcc tttggcgttt tcaggttctc    240
agagaaaata acttcaaaca aacaattcct cgtgtgacta tagaagatgg agaggaaatc    300
acataccaaa aagtcacaag cgccgtcaga aggggcgcac accaccttgc ggcactgcag    360
acctctgatg gccattggcc tgctcaaatt gcaggtcctc tcttctttct tcctcccttg    420 gtttttgta tgtatattac aggaaatctt gaatcagtat ttccagaaga acatcgcaaa     480
gaaattcttc gttacacata ttatcaccag aatgaagacg gaggatgggg actacacata    540
gagggtcata gcactatgtt ttgtactgca ctgaactata tatgcatgcg aatgcttgga    600
gaaggaccta atggaggtca tgacaatgct tgtgctagag caagaaagtg gattcgagat    660
catggtggtg taacacatat accttcatgg ggaaaaactt ggcttcgat actcggtgta     720 tttgattggt gcggaagcaa cccaatgccc ccagagtttt ggatccttcc atcttttctt    780
cctatgcatc cagctaagat gtggtgttac tgtcgattgg tatacatgcc tatgtcttac    840
ttatatggga agaggtttgt gggtccaatc acaccactca tcttacaatt aagagaagag    900
ttgtttactc aaccttatga aaagttaat tggaagaaag cgcgtcacca atgtgcaaag     960
gaagatcttt actatcccca tcctttgata caagacctaa tatgggatag tttatacata    1020
ttcactgaac cgctacttac tcgttggcct ttcaacaagt tgattagaga aaaggccctt    1080
caagtaacta tgaaacatat tcattatgaa gatgagacta gtcgatacat aaccattggt    1140
tgtgtggaaa aggtttttatg tatgcttgct tgttgggtgg aagatccaaa cggagatgct    1200
ttcaagaagc atcttgcaag ggtcccagat tactatgggg tttctgaaga tggaatgacc    1260
atgcagagtt ttggtagcca agaatgggat gctggctttg ctgttcaagc tttgcttgcc    1320
actaacataa ttgaagaaat tggtcctacg tttgcaaaag gacatgattt catcaagaag    1380
tctcaggtga aggataatcc ttttggagat tttaaaagta tgcatcgtca tatttctaaa    1440
gggtcttgga cattctctga tcaagaccat ggatggcaag tttctgattg cactgcagaa    1500
```

```
ggtttaaagt gttgtctact tctatcaatg ttgccaccag agattgtggg agaaaagatg    1560
gaacctgaaa gattatacga ttcagtcaat gtcttgttgt cgcttcagag taaaaaaggt    1620
ggtttagcag catgggagcc tgcaggagct caagagtggt tagaattact caatcccaca    1680 gaatttttg cggacattgt agttgaacat gaatatgttg agtgcactgg atctgcaatc    1740
caagctttag ttttgttcaa gaagctatat ccaggacata ggaagaaaga gatagaaaat    1800
ttcattacca atgcagttcg attccttgaa gatacacaaa cagctgatgg ttcatggtat    1860
ggaaattggg gagtttgctt cacttatggc tcttggtttg cacttggagg tctagcagct    1920
gctggtaaga cttacaccaa ttgtgctgcc attcgcaaag ccgttaaatt tctacttaca    1980
acacaaagag aggacggtgg atggggagag agttatcttt caagcccaaa aaagatatat    2040
gtacctctag aaggaagccg atcaaatgtt gtacatacag catgggctct tatgggacta    2100
attcatgctg acaggcgga tagagacccc atgcctcttc accgtgctgc aaagttgctc    2160
attaattctc agttggaaga gggtgattgg ccccaacagg aaatcacggg agtattcatg    2220
aaaaattgca tgttgcatta tccaatgtac agagatattt atccaatgtg ggctctagct    2280
gaatatcgaa ggcgggttcc attgccttcc actgaagttt aatttagaat ggtttgagca    2340
cgaaaaggca aaggcatttt cattaagatt gaggcaaata agttgtgtgt aatcaagctt    2400
aatcaatttt ttcatattcc tatgtttatt tcctacatat attggtagaa aaattatttc    2460
aaaaaaaaaa aaaaaaaa                                                  2478

<210> SEQ ID NO 3
<211> LENGTH: 7701
<212> TYPE: DNA
<213> ORGANISM: Artificial Sequence
<220> FEATURE:
<223> OTHER INFORMATION: Expression vector pKS151
<220> FEATURE:
<221> NAME/KEY: misc_feature
<222> LOCATION: (6516)..(6516)
<223> OTHER INFORMATION: n is a, c, g, or t

<400> SEQUENCE: 3
cgcgcccgat catccggata tagttcctcc tttcagcaaa aaacccctca agacccgttt      60
agaggcccca aggggttatg ctagttattg ctcagcggtg gcagcagcca actcagcttc     120
ctttcgggct ttgttagcag ccggatcgat ccaagctgta cctcactatt cctttgccct     180
cggacgagtg ctggggcgtc ggtttccact atcggcgagt acttctacac agccatcggt     240
ccagacggcc gcgcttctgc gggcgatttg tgtacgcccg acagtcccgg ctccggatcg     300
gacgattgcg tcgcatcgac cctgcgccca agctgcatca tcgaaattgc cgtcaaccaa     360
gctctgatag agttggtcaa gaccaatgcg gagcatatac gcccggagcc gcggcgatcc     420
tgcaagctcc ggatgcctcc gctcgaagta gcgcgtctgc tgctccatac aagccaacca     480
cggcctccag aagaagatgt tggcgacctc gtattgggaa tccccgaaca tcgcctcgct     540
ccagtcaatg accgctgtta tgcggccatt gtccgtcagg acattgttgg agccgaaatc     600
cgcgtgcacg aggtgccgga cttcggggca gtcctcggcc caaagcatca gctcatcgag     660
agcctgcgcg acggacgcac tgacggtgtc gtccatcaca gtttgccagt gatacacatg     720
gggatcagca atcgcgcata tgaaatcacg ccatgtagtg tattgaccga ttccttgcgg     780
tccgaatggg ccgaacccgc tcgtctggct aagatcggcc gcagcgatcg catccatagc     840
ctccgcgacc ggctgcagaa cagcgggcag ttcggtttca ggcaggtctt gcaacgtgac     900
accctgtgca cggcgggaga tgcaataggt caggctctcg ctgaattccc caatgtcaag     960
```

-continued

```
cacttccgga atcgggagcg cggccgatgc aaagtgccga taaacataac gatctttgta    1020
gaaaccatcg gcgcagctat ttacccgcag acatatcca cgccctccta catcgaagct    1080
gaaagcacga gattcttcgc cctccgagag ctgcatcagg tcggagacgc tgtcgaactt    1140
ttcgatcaga aacttctcga cagacgtcgc ggtgagttca ggcttttcca tgggtatatc    1200
tccttcttaa agttaaacaa aattatttct agagggaaac cgttgtggtc tccctatagt    1260
gagtcgtatt aatttcgcgg gatcgagatc gatccaattc caatcccaca aaaatctgag    1320
cttaacagca cagttgctcc tctcagagca gaatcgggta ttcaacaccc tcatatcaac    1380
tactacgttg tgtataacgg tccacatgcc ggtatatacg atgactgggg ttgtacaaag    1440
gcggcaacaa acggcgttcc cggagttgca cacaagaaat ttgccactat tacagaggca    1500
agagcagcag ctgacgcgta cacaacaagt cagcaaacag acaggttgaa cttcatcccc    1560
aaaggagaag ctcaactcaa gcccaagagc tttgctaagg ccctaacaag cccaccaaag    1620
caaaaagccc actggctcac gctaggaacc aaaaggccca gcagtgatcc agccccaaaa    1680
gagatctcct ttgccccgga gattacaatg gacgatttcc tctatcttta cgatctagga    1740
aggaagttcg aaggtgaagg tgacgacact atgttcacca ctgataatga aaggttagc    1800 ctcttcaatt tcagaaagaa tgctgaccca cagatggtta gagaggccta cgcagcaggt    1860
ctcatcaaga cgatctaccc gagtaacaat ctccaggaga tcaaatacct tcccaagaag    1920
gttaaagatg cagtcaaaag attcaggact aattgcatca agaacacaga gaaagacata    1980
tttctcaaga tcagaagtac tattccagta tggacgattc aaggcttgct tcataaacca    2040
aggcaagtaa tagagattgg agtctctaaa aaggtagttc ctactgaatc taaggccatg    2100
catggagtct aagattcaaa tcgaggatct aacagaactc gccgtgaaga ctggcgaaca    2160
gttcatacag agtcttttac gactcaatga caagaagaaa atcttcgtca acatggtgga    2220
gcacgacact ctggtctact ccaaaaatgt caaagataca gtctcagaag accaaagggc    2280
tattgagact tttcaacaaa ggataatttc gggaaacctc ctcggattcc attgcccagc    2340
tatctgtcac ttcatcgaaa ggacagtaga aaaggaaggt ggctcctaca aatgccatca    2400
ttgcgataaa ggaaaggcta tcattcaaga tgcctctgcc gacagtggtc ccaaagatgg    2460 accccaccc acgaggagca tcgtggaaaa agaagacgtt ccaaccacgt cttcaaagca    2520
agtggattga tgtgacatct ccactgacgt aagggatgac gcacaatccc actatccttc    2580
gcaagaccct tcctctatat aaggaagttc atttcatttg gagaggacac gctcgagctc    2640
atttctctat tacttcagcc ataacaaaag aactcttttc tcttcttatt aaaccatgaa    2700
aaagcctgaa ctcaccgcga cgtctgtcga agtttctg atcgaaaagt tcgacagcgt    2760
ctccgacctg atgcagctct cggagggcga agaatctcgt gctttcagct tcgatgtagg    2820
agggcgtgga tatgtcctgc gggtaaatag ctgcgccgat ggtttctaca agatcgtta    2880 tgtttatcgg cactttgcat cggccgcgct cccgattccg gaagtgcttg acattgggga    2940
attcagcgag agcctgacct attgcatctc ccgccgtgca cagggtgtca cgttgcaaga    3000
cctgcctgaa accgaactgc ccgctgttct gcagccggtc gcggaggcca tggatgcgat    3060
cgctgcggcc gatcttagcc agacgagcgg gttcggccca ttcggaccgc aaggaatcgg    3120
tcaatacact acatggcgtg atttcatatg cgcgattgct gatccccatg tgtatcactg    3180
gcaaactgtg atggacgaca ccgtcagtgc gtccgtcgcg caggctctcg atgagctgat    3240
gctttgggcc gaggactgcc ccgaagtccg gcacctcgtg cacgcggatt tcggctccaa    3300
```

```
caatgtcctg acggacaatg gccgcataac agcggtcatt gactggagcg aggcgatgtt    3360
cggggattcc caatacgagg tcgccaacat cttcttctgg aggccgtggt tggcttgtat    3420
ggagcagcag acgcgctact tcgagcggag gcatccggag cttgcaggat cgccgcggct    3480
ccgggcgtat atgctccgca ttggtcttga ccaactctat cagagcttgg ttgacggcaa    3540
tttcgatgat gcagcttggg cgcagggtcg atgcgacgca atcgtccgat ccggagccgg    3600
gactgtcggg cgtacacaaa tcgcccgcag aagcgcggcc gtctggaccg atggctgtgt    3660
agaagtactc gccgatagtg gaaaccgacg ccccagcact cgtccgaggg caaaggaata    3720
gtgaggtacc taaagaagga gtgcgtcgaa gcagatcgtt caaacatttg gcaataaagt    3780
ttcttaagat tgaatcctgt tgccggtctt gcgatgatta tcatataatt tctgttgaat    3840
tacgttaagc atgtaataat taacatgtaa tgcatgacgt tatttatgag atgggttttt    3900
atgattagag tcccgcaatt atacatttaa tacgcgatag aaaacaaaat atagcgcgca    3960
aactaggata aattatcgcg cgcggtgtca tctatgttac tagatcgatg tcgaatctga    4020
tcaacctgca ttaatgaatc ggccaacgcg cggggagagg cggtttgcgt attgggcgct    4080
cttccgcttc ctcgctcact gactcgctgc gctcggtcgt tcggctgcgg cgagcggtat    4140
cagctcactc aaaggcggta atacggttat ccacagaatc aggggataac gcaggaaaga    4200
acatgtgagc aaaaggccag caaaaggcca ggaaccgtaa aaaggccgcg ttgctggcgt    4260
ttttccatag gctccgcccc cctgacgagc atcacaaaaa tcgacgctca agtcagaggt    4320
ggcgaaaccc gacaggacta taaagatacc aggcgtttcc ccctggaagc tccctcgtgc    4380
gctctcctgt tccgaccctg ccgcttaccg gatacctgtc cgcctttctc ccttcgggaa    4440
gcgtggcgct ttctcaatgc tcacgctgta ggtatctcag ttcggtgtag tcgttcgct    4500 ccaagctggg ctgtgtgcac gaaccccccg ttcagcccga ccgctgcgcc ttatccggta    4560
actatcgtct tgagtccaac ccggtaagac acgacttatc gccactggca gcagccactg    4620
gtaacaggat tagcagagcg aggtatgtag gcggtgctac agagttcttg aagtggtggc    4680
ctaactacgg ctacactaga aggacagtat ttggtatctg cgctctgctg aagccagtta    4740
ccttcggaaa aagagttggt agctcttgat ccggcaaaca accaccgct ggtagcggtg    4800 gtttttttgt ttgcaagcag cagattacgc gcagaaaaaa aggatctcaa gaagatcctt    4860
tgatcttttc tacgggtct gacgctcagt ggaacgaaaa ctcacgttaa gggattttgg    4920
tcatgacatt aacctataaa aataggcgta tcacgaggcc ctttcgtctc gcgcgtttcg    4980
gtgatgacgg tgaaaacctc tgacacatgc agctcccgga gcggtcaca gcttgtctgt    5040 aagcggatgc cgggagcaga caagcccgtc agggcgcgtc agcgggtgtt ggcgggtgtc    5100
ggggctggct taactatgcg gcatcagagc agattgtact gagagtgcac catatggaca    5160
tattgtcgtt agaacgcggc tacaattaat acataacctt atgtatcata cacatacgat    5220
ttaggtgaca ctatagaacg gcgcgccgtc gacggatata atgagccgta acaaagatg    5280 attaagtagt aattaatacg tactagtaaa agtggcaaaa gataacgaga aagaaccaat    5340
ttctttgcat tcggccttag cggaaggcat atataagctt tgattatttt atttagtgta    5400
atgatttcgt acaaccaaag catttattta gtactctcac acttgtgtcg cggccggagc    5460
tggtcatctc gctcatcgtc gagtcggcgg ccggagctgg tcatctcgct catcgtcgag    5520
tcggcggccg ccgactcgac gatgagcgag atgaccagct ccggccgccg actcgacgat    5580
gagcgagatg accagctccg gccgcttggg gggctatgga agactttctt agttagttgt    5640
gtgaataagc aatgttggga gaatcgggac tacttatagg ataggaataa aacagaaaag    5700
```

```
tattaagtgc taatgaaata tttagactga taattaaaat cttcacgtat gtccacttga    5760
tataaaaacg tcaggaataa aggaagtaca gtagaattta aaggtactct ttttatatat    5820
acccgtgttc tcttttttggc tagctagttg cataaaaaat aatctatatt tttatcatta    5880
ttttaaatat cttatgagat ggtaaatatt tatcataatt ttttttacta ttatttatta    5940
tttgtgtgtg taatacatat agaagttaat tacaaattt atttacttt tcattatttt    6000 gatatgattc accattaatt tagtgttatt atttataata gttcatttta atctttttgt    6060
atatattatg cgtgcagtac ttttttccta catataacta ctattacatt ttatttatat    6120
aatattttta ttaatgaatt ttcgtgataa tatgtaatat tgttcattat tatttcagat    6180
tttttaaaaa tatttgtgtt attatttatg aaatatgtaa ttttttttagt atttgatttt    6240 atgatgataa agtgttctaa attcaaaaga aggggggaaag cgtaaacatt aaaaaacgtc    6300
atcaaacaaa aacaaaatct tgttaataaa gataaaactg tttgttttga tcactgttat    6360
ttcgtaatat aaaaacatta tttatattta tattgttgac aaccaaattt gcctatcaaa    6420
tctaaccaat ataatgcatg cgtggcaggt aatgtactac catgaactta agtcatgaca    6480
taataaaccg tgaatctgac caatgcatgt acctanctaa attgtatttg tgacacgaag    6540
caaatgattc aattcacaat ggagatggga acaaataat gaagaaccca gaactaagaa    6600
agcttttctg aaaaataaaa taaaggcaat gtcaaaagta tactgcatca tcagtccaga    6660
aagcacatga tattttttta tcagtatcaa tgcagctagt tttattttac aatatcgata    6720
tagctagttt aaatatattg cagctagatt tataaatatt tgtgttatta tttatcattt    6780
gtgtaatcct gttttagta ttttagttta tatatgatga taatgtattc caaatttaaa    6840
agaagggaaa taaattaaaa caagaaaaaa agtcatcaaa caaaaaacaa atgaaagggt    6900
ggaaagatgt taccatgtaa tgtgaatgtt acagtatttc ttttattata gagttaacaa    6960
attaactaat atgattttgt taataatgat aaaatatttt ttttattatt atttcataat    7020
ataaaaatag tttacttaat ataaaaaaaa ttctatcgtt cacaacaaag ttggccacct    7080
aatttaacca tgcatgtacc catggaccat attaggtaac catcaaacct gatgaagaga    7140
taaagagatg aagacttaag tcataacaca aaaccataaa aaacaaaaat acaatcaacc    7200
gtcaatctga ccaatgcatg aaaaagctgc aatagtgagt ggcgacacaa agcacatgat    7260
tttcttacaa cggagataaa accaaaaaaa tatttcatga acaacctaga acaaataaag    7320
cttttatata ataaatatat aaataaataa aggctatgga ataatatact tcaatatatt    7380
tggattaaat aaaattgttgg cggggttgat atatttatac acacctaaag tcacttcaat    7440
ctcattttca cttaactttt atttttttt tctttttatt tatcataaag agaatattga    7500
taatatactt tttaacatat ttttatgaca tttttttattg gtgaaaactt attaaaaatc    7560
ataaattttg taagttagat ttatttaaag agttcctctt cttatttaa attttttaat    7620 aaatttttaa ataactaaaa tttgtgttaa aaatgttaaa aaatgtgtta ttaacccttc    7680
tcttcgagga tccaagcttg g                                              7701
```

<210> SEQ ID NO 4
<211> LENGTH: 36
<212> TYPE: DNA
<213> ORGANISM: Artificial
<220> FEATURE:
<223> OTHER INFORMATION: 36 nucleotide sequence

<400> SEQUENCE: 4

-continued

```
cggccggagc tggtcatctc gctcatcgtc gagtcg                                    36

<210> SEQ ID NO 5
<211> LENGTH: 30
<212> TYPE: DNA
<213> ORGANISM: Artificial sequence
<220> FEATURE:
<223> OTHER INFORMATION: Oligonucleotide primer BM1

<400> SEQUENCE: 5
gcggccgcca acaatttaga agaggctcgg                                           30

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide primer BM2

<400> SEQUENCE: 6
ttcttggaga aggacctaat ggaggtcatg                                           30

<210> SEQ ID NO 7
<211> LENGTH: 30
<212> TYPE: DNA
<213> ORGANISM: Artificial Sequence
<220> FEATURE:
<223> OTHER INFORMATION: Oligonucleotide primer BM3

<400> SEQUENCE: 7
gcggccgcat gtggaggctg aagatagcag                                           30

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide primer BM4

<400> SEQUENCE: 8
gtcatgacct ccattaggtc cttctccaag                                           30

<210> SEQ ID NO 9
<211> LENGTH: 1013
<212> TYPE: DNA
<213> ORGANISM: Artificial Sequence
<220> FEATURE:
<223> OTHER INFORMATION: Chimera comprising portions of sah1c.pk002.n23
      and src3c.pk024.m11

<400> SEQUENCE: 9
atgtggaggc tgaagatagc agatggagga atgatccat acatattcag cacaaacaat           60
ttcgttggga ggcagacatg ggagtttgat cctgaagcag gcagtccaga ggaacgggcc          120
caggttgaag cagctcgtca gcatttctac cacaaccgct tcaaggtcaa gccctgcgct          180
gacctccttt ggcgttttca ggttctcaga gaaaataact tcaaacaaac aattcctcgt         240
gtgactatag aagatggaga ggaaatcaca taccaaaaag tcacaagcgc cgtcagaagg          300
ggcgcacacc accttgcggc actgcagacc tctgatggcc attggcctgc tcaaattgca          360
ggtcctctct tctttcttcc tcccttggtt ttttgtatgt atattacagg aaatcttgaa          420
tcagtatttc cagaagaaca tcgcaaagaa attcttcgtt acacatatta tcaccagaat          480
gaagacggag gatggggact acacatagag ggtcatagca ctatgttttg tactgcactg          540
```

-continued

| | |
|---|---|
| aactatatat gcatgcgaat kcttggagaa ggacctaatg gaggtcatra caatgcttgt | 600 |
| gctaaagcaa gaaagtggat tcatgatcat ggtggtgcaa cacatatacc ttcatggggg | 660 |
| aaattttggc tttcggtact tggtatagtt gattggtgtg gaagcaaccc aatgccgcct | 720 |
| gaattttgga tccttccttc ttttctccct atgcatccgg gtaaaatgtg gtgttattgt | 780 |
| cggttggtat acatgcccat gtcttatttg tatgggaaga aatttacggg tccaatcaca | 840 |
| ccgttagttg taaatttgag agaagaactt tttattcaac cttatgatga aaatagttgg | 900 |
| aagaaagcac gtcataaatg tgcaaatgaa gatctttact atccccatca ttggatacaa | 960 |
| gatctattat gggatagttt gtatgtattc accgagcctc ttctaaattg ttg | 1013 |

<210> SEQ ID NO 10
<211> LENGTH: 8724
<212> TYPE: DNA
<213> ORGANISM: Artificial Sequence
<220> FEATURE:
<223> OTHER INFORMATION: plasmid AC18
<220> FEATURE:
<221> NAME/KEY: misc_feature
<222> LOCATION: (985)..(985)
<223> OTHER INFORMATION: n is a, c, g, or t

<400> SEQUENCE: 10

| | |
|---|---|
| cgactcgacg atgagcgaga tgaccagctc cggccgccga ctcgacgatg agcgagatga | 60 |
| ccagctccgg ccgcttgggg ggctatggaa gactttctta gttagttgtg tgaataagca | 120 |
| atgttgggag aatcgggact acttatagga taggaataaa acagaaaagt attaagtgct | 180 |
| aatgaaatat ttagactgat aattaaaatc ttcacgtatg tccacttgat ataaaaacgt | 240 |
| caggaataaa ggaagtacag tagaatttaa aggtactctt tttatatata cccgtgttct | 300 |
| cttttttggct agctagttgc ataaaaaata atctatattt ttatcattat tttaaatatc | 360 |
| ttatgagatg gtaaatattt atcataattt ttttactat tatttattat ttgtgtgtgt | 420 |
| aatacatata gaagttaatt acaaattta tttacttttt cattattttg atatgattca | 480 |
| ccattaattt agtgttatta tttataatag ttcattttaa tcttttttgta tatattatgc | 540 |
| gtgcagtact ttttccctac atataactac tattacattt tatttatata atattttat | 600 |
| taatgaattt tcgtgataat atgtaatatt gttcattatt atttcagatt ttttaaaaat | 660 |
| atttgtgtta ttatttatga aatatgtaat ttttttagta tttgatttta tgatgataaa | 720 |
| gtgttctaaa ttcaaaagaa gggggaaagc gtaaacatta aaaacgtca tcaaacaaaa | 780 |
| acaaaatctt gttaataaag ataaaactgt ttgttttgat cactgttatt tcgtaatata | 840 |
| aaaacattat ttatatttat attgttgaca accaaatttg cctatcaaat ctaaccaata | 900 |
| taatgcatgc gtggcaggta atgtactacc atgaacttaa gtcatgacat aataaaccgt | 960 |
| gaatctgacc aatgcatgta cctanctaaa ttgtatttgt gacacgaagc aaatgattca | 1020 |
| attcacaatg gagatgggaa acaaataatg aagaacccag aactaagaaa gcttttctga | 1080 |
| aaaataaaat aaaggcaatg tcaaagtat actgcatcat cagtccagaa agcacatgat | 1140 |
| atttttttat cagtatcaat gcagctagtt ttattttaca atatcgatat agctagttta | 1200 |
| aatatattgc agctagattt ataaatattt gtgttattat ttatcatttg tgtaatcctg | 1260 |
| ttttttagtat tttagtttat atatgatgat aatgtattcc aaatttaaaa gaagggaaat | 1320 |
| aaatttaaac aagaaaaaaa gtcatcaaac aaaaaacaaa tgaaagggtg gaaagatgtt | 1380 |
| accatgtaat gtgaatgtta cagtatttct tttattatag agttaacaaa ttaactaata | 1440 |
| tgattttgtt aataatgata aaatattttt tttattatta tttcataata taaaaatagt | 1500 |

```
ttacttaata taaaaaaaat tctatcgttc acaacaaagt tggccaccta atttaaccat    1560
gcatgtaccc atggaccata ttaggtaacc atcaaacctg atgaagagat aaagagatga    1620
agacttaagt cataacacaa aaccataaaa aacaaaaata caatcaaccg tcaatctgac    1680
caatgcatga aaaagctgca atagtgagtg gcgacacaaa gcacatgatt ttcttacaac    1740
ggagataaaa ccaaaaaaat atttcatgaa caacctagaa caaataaagc ttttatataa    1800
taaatatata aataaataaa ggctatggaa taatatactt caatatattt ggattaaata    1860
aattgttggc ggggttgata tatttataca cacctaaagt cacttcaatc tcattttcac    1920
ttaacttta ttttttttt ctttttattt atcataaaga gaatattgat aatatacttt     1980
ttaacatatt tttatgacat tttttattgg tgaaaactta ttaaaaatca taaattttgt    2040
aagttagatt tattttaaaga gttcctcttc ttattttaaa ttttttaata aattttaaa    2100
taactaaaat ttgtgttaaa aatgttaaaa aatgtgttat taaccttct cttcgaggat     2160
ccaagcttgg cgcgcccgat catccggata tagttcctcc tttcagcaaa aaacccctca    2220
agacccgttt agaggcccca aggggttatg ctagttattg ctcagcggtg gcagcagcca    2280
actcagcttc ctttcgggct tgttagcag ccggatcgat ccaagctgta cctcactatt      2340
cctttgccct cggacgagtg ctggggcgtc ggtttccact atcggcgagt acttctacac    2400
agccatcggt ccagacggcc gcgcttctgc gggcgatttg tgtacgcccg acagtcccgg    2460
ctccggatcg gacgattgcg tcgcatcgac cctgcgccca agctgcatca tcgaaattgc    2520
cgtcaaccaa gctctgatag agttggtcaa gaccaatgcg gagcatatac gcccggagcc    2580
gcggcgatcc tgcaagctcc ggatgcctcc gctcgaagta gcgcgtctgc tgctccatac    2640
aagccaacca cggcctccag aagaagatgt tggcgacctc gtattgggaa tccccgaaca    2700
tcgcctcgct ccagtcaatg accgctgtta tgcggccatt gtccgtcagg acattgttgg    2760
agccgaaatc cgcgtgcacg aggtgccgga cttcggggca gtcctcggcc caaagcatca    2820
gctcatcgag agcctgcgcg acggacgcac tgacggtgtc gtccatcaca gtttgccagt    2880
gatacacatg gggatcagca atcgcgcata tgaaatcacg ccatgtagtg tattgaccga    2940
ttccttgcgg tccgaatggg ccgaacccgc tcgtctggct aagatcggcc gcagcgatcg    3000
catccatagc ctccgcgacc ggctgcagaa cagcgggcag ttcggtttca ggcaggtctt    3060
gcaacgtgac accctgtgca cggcgggaga tgcaataggt caggctctcg ctgaattccc    3120
caatgtcaag cacttccgga atcgggagcg cggccgatgc aaagtgccga taaacataac    3180
gatctttgta gaaaccatcg gcgcagctat ttacccgcag gacatatcca cgccctccta    3240
catcgaagct gaaagcacga gattcttcgc cctccgagag ctgcatcagg tcggagacgc    3300
tgtcgaactt ttcgatcaga aacttctcga cagacgtcgc ggtgagttca ggcttttcca    3360
tgggtatatc tccttcttaa agttaaacaa aattatttct agagggaaac cgttgtggtc    3420
tccctatagt gagtcgtatt aatttcgcgg gatcgagatc gatccaattc caatcccaca    3480
aaaatctgag cttaacagca cagttgctcc tctcagagca gaatcgggta ttcaacaccc    3540
tcatatcaac tactacgttg tgtataacgg tccacatgcc ggtatatacg atgactgggg    3600
ttgtacaaag gcggcaacaa acggcgttcc cggagttgca cacaagaaat ttgccactat    3660
tacagaggca agagcagcag ctgacgcgta cacaacaagt cagcaaacag acaggttgaa    3720
cttcatcccc aaaggagaag ctcaactcaa gcccaagagc tttgctaagg ccctaacaag    3780
cccaccaaag caaaaagccc actggctcac gctaggaacc aaaaggccca gcagtgatcc    3840
```

```
agccccaaaa gagatctcct ttgccccgga gattacaatg gacgatttcc tctatcttta    3900
cgatctagga aggaagttcg aaggtgaagg tgacgacact atgttcacca ctgataatga    3960
gaaggttagc ctcttcaatt tcagaaagaa tgctgaccca cagatggtta gagaggccta    4020
cgcagcaggt ctcatcaaga cgatctaccc gagtaacaat ctccaggaga tcaaatacct    4080
tcccaagaag gttaaagatg cagtcaaaag attcaggact aattgcatca agaacacaga    4140
gaaagacata tttctcaaga tcagaagtac tattccagta tggacgattc aaggcttgct    4200
tcataaacca aggcaagtaa tagagattgg agtctctaaa aaggtagttc ctactgaatc    4260
taaggccatg catggagtct aagattcaaa tcgaggatct aacagaactc gccgtgaaga    4320
ctggcgaaca gttcatacag agtcttttac gactcaatga caagaagaaa atcttcgtca    4380
acatggtgga gcacgacact ctggtctact ccaaaaatgt caaagataca gtctcagaag    4440
accaaagggc tattgagact tttcaacaaa ggataatttc gggaaacctc ctcggattcc    4500
attgcccagc tatctgtcac ttcatcgaaa ggacagtaga aaaggaaggt ggctcctaca    4560
aatgccatca ttgcgataaa ggaaaggcta tcattcaaga tgcctctgcc gacagtggtc    4620
ccaaagatgg accccaccc acgaggagca tcgtggaaaa agaagacgtt ccaaccacgt    4680
cttcaaagca agtggattga tgtgacatct ccactgacgt aagggatgac gcacaatccc    4740
actatccttc gcaagaccct tcctctatat aaggaagttc atttcatttg gagaggacac    4800
gctcgagctc atttctctat tacttcagcc ataacaaaag aactcttttc tcttcttatt    4860
aaaccatgaa aaagcctgaa ctcaccgcga cgtctgtcga agtttctg atcgaaaagt    4920
tcgacagcgt ctccgacctg atgcagctct cggagggcga agaatctcgt gctttcagct    4980
tcgatgtagg agggcgtgga tatgtcctgc gggtaaatag ctgcgccgat ggtttctaca    5040
aagatcgtta tgtttatcgg cactttgcat cggccgcgct cccgattccg gaagtgcttg    5100
acattgggga attcagcgag agcctgacct attgcatctc ccgccgtgca cagggtgtca    5160
cgttgcaaga cctgcctgaa accgaactgc ccgctgttct gcagccggtc gcggaggcca    5220
tggatgcgat cgctgcggcc gatcttagcc agacgagcgg gttcggccca ttcggaccgc    5280
aaggaatcgg tcaatacact acatggcgtg atttcatatg cgcgattgct gatccccatg    5340
tgtatcactg gcaaactgtg atggacgaca ccgtcagtgc gtccgtcgcg caggctctcg    5400
atgagctgat gctttgggcc gaggactgcc ccgaagtccg gcacctcgtg cacgcggatt    5460
tcggctccaa caatgtcctg acggacaatg gccgcataac agcggtcatt gactggagcg    5520
aggcgatgtt cggggattcc caatacgagg tcgccaacat cttcttctgg aggccgtggt    5580
tggcttgtat ggagcagcag acgcgctact cgagcggag gcatccgag cttgcaggat    5640
cgccgcggct ccgggcgtat atgctccgca ttggtcttga ccaactctat cagagcttgg    5700
ttgacggcaa tttcgatgat gcagcttggg cgcagggtcg atgcgacgca atcgtccgat    5760
ccggagccga gactgtcggg cgtacacaaa tcgcccgcag aagcgcggcc gtctggaccg    5820
atggctgtgt agaagtactc gccgatagtg gaaaccgacg ccccagcact cgtccgaggg    5880
caaaggaata gtgaggtacc taagaaggga gtgcgtcgaa gcagatcgtt caaacatttg    5940
gcaataaagt ttcttaagat tgaatcctgt tgccggtctt gcgatgatta tcatataatt    6000
tctgttgaat tacgttaagc atgtaataat taacatgtaa tgcatgacgt tatttatgag    6060
atgggttttt atgattagag tcccgcaatt atacatttaa tacgcgatag aaaacaaaat    6120
atagcgcgca aactaggata aattatcgcg cgcggtgtca tctatgttac tagatcgatg    6180
tcgaatctga tcaacctgca ttaatgaatc ggccaacgcg cggggagagg cggtttgcgt    6240
```

-continued

```
attgggcgct cttccgcttc ctcgctcact gactcgctgc gctcggtcgt tcggctgcgg   6300
cgagcggtat cagctcactc aaaggcggta atacggttat ccacagaatc aggggataac   6360
gcaggaaaga acatgtgagc aaaaggccag caaaaggcca ggaaccgtaa aaaggccgcg   6420
ttgctggcgt ttttccatag gctccgcccc cctgacgagc atcacaaaaa tcgacgctca   6480
agtcagaggt ggcgaaaccc gacaggacta taaagatacc aggcgtttcc ccctggaagc   6540
tccctcgtgc gctctcctgt tccgaccctg ccgcttaccg gatacctgtc cgcctttctc   6600
ccttcgggaa gcgtggcgct ttctcaatgc tcacgctgta ggtatctcag ttcggtgtag   6660
gtcgttcgct ccaagctggg ctgtgtgcac gaaccccccg ttcagcccga ccgctgcgcc   6720
ttatccggta actatcgtct tgagtccaac ccggtaagac acgacttatc gccactggca   6780
gcagccactg gtaacaggat tagcagagcg aggtatgtag gcggtgctac agagttcttg   6840
aagtggtggc ctaactacgg ctacactaga aggacagtat ttggtatctg cgctctgctg   6900
aagccagtta ccttcggaaa aagagttggt agctcttgat ccggcaaaca aaccaccgct   6960
ggtagcggtg gttttttgt ttgcaagcag cagattacgc gcagaaaaaa aggatctcaa   7020
gaagatcctt tgatcttttc tacggggtct gacgctcagt ggaacgaaaa ctcacgttaa   7080
gggattttgg tcatgacatt aacctataaa aataggcgta tcacgaggcc ctttcgtctc   7140
gcgcgtttcg gtgatgacgg tgaaaacctc tgacacatgc agctcccgga cggtcaca    7200
gcttgtctgt aagcggatgc cgggagcaga caagcccgtc agggcgcgtc agcgggtgtt   7260
ggcgggtgtc ggggctggct taactatgcg gcatcagagc agattgtact gagagtgcac   7320
catatggaca tattgtcgtt agaacgcggc tacaattaat acataacctt atgtatcata   7380
cacatacgat ttaggtgaca ctatagaacg gcgcgccgtc gacggatata atgagccgta   7440
aacaaagatg attaagtagt aattaatacg tactagtaaa agtggcaaaa gataacgaga   7500
aagaaccaat ttctttgcat tcggccttag cggaaggcat atataagctt tgattatttt   7560
atttagtgta atgatttcgt acaaccaaag catttattta gtactctcac acttgtgtcg   7620
cggccggagc tggtcatctc gctcatcgtc gagtcggcgg ccggagctgg tcatctcgct   7680
catcgtcgag tcggcgcggc cgcatgtgga ggctgaagat agcagatgga ggaaatgatc   7740
catacatatt cagcacaaac aatttcgttg gaggcagac atgggagttt gatcctgaag   7800
caggcagtcc agaggaacgg gcccaggttg aagcagctcg tcagcatttc taccacaacc   7860
gcttcaaggt caagccctgc gctgacctcc tttggcgttt tcaggttctc agagaaaata   7920
acttcaaaca aacaattcct cgtgtgacta tagaagatgg agaggaaatc ataccaaaa   7980
aagtcacaag cgccgtcaga aggggcgcac accaccttgc ggcactgcag acctctgatg   8040
gccattggcc tgctcaaatt gcaggtcctc tcttctttct tcctcccttg gttttttgta   8100
tgtatattac aggaaatctt gaatcagtat ttccagaaga acatcgcaaa gaaattcttc   8160
gttacacata ttatcaccag aatgaagacg gaggatgggg actacacata gagggtcata   8220
gcactatgtt ttgtactgca ctgaactata tatgcatgcg aatkcttgga gaaggaccta   8280
atggaggtca tracaatgct tgtgctaaag caagaaagtg gattcatgat catggtggtg   8340
caacacatat accttcatgg gggaaatttt ggctttcggt acttggtata gttgattggt   8400
gtggaagcaa cccaatgccg cctgaatttt ggatccttcc ttcttttctc cctatgcatc   8460
cgggtaaaat gtggtgttat tgtcggttgg tatacatgcc catgtcttat ttgtatggga   8520
agaaatttac gggtccaatc acaccgttag ttgtaaattt gagagaagaa cttttttattc   8580
```

-continued

```
aaccttatga tgaaaatagt tggaagaaag cacgtcataa atgtgcaaat gaagatcttt    8640
actatcccca tcattggata caagatctat tatgggatag tttgtatgta ttcaccgagc    8700
ctcttctaaa ttgttggcgg ccgc                                          8724
```

<210> SEQ ID NO 11
<211> LENGTH: 6383
<212> TYPE: DNA
<213> ORGANISM: Artificial Sequence
<220> FEATURE:
<223> OTHER INFORMATION: Plant selectable marker gene expression
      cassette +promoter and terminator separated by Not I
<220> FEATURE:
<221> NAME/KEY: misc_feature
<222> LOCATION: (1212)..(1212)
<223> OTHER INFORMATION: n is a, c, g, or t

<400> SEQUENCE: 11

```
cgggcccccc ctcgaggtcg acggtatcga taagcttgat atcgaattcc tgcagcccgg      60
gggatccact agttctagag cggccgcgc cgtcgacgga tataatgagc cgtaaacaaa     120
gatgattaag tagtaattaa tacgtactag taaaagtggc aaaagataac gagaaagaac     180
caatttcttt gcattcggcc ttagcggaag gcatatataa gctttgatta ttttatttag     240
tgtaatgatt tcgtacaacc aaagcattta tttagtactc tcacacttgt gtcgcggccg     300
cttggggggc tatggaagac tttcttagtt agttgtgtga ataagcaatg ttgggagaat     360
cgggactact tataggatag gaataaaaca gaaaagtatt aagtgctaat gaaatattta     420
gactgataat taaaatcttc acgtatgtcc acttgatata aaaacgtcag gaataaagga     480
agtacagtag aatttaaagg tactcttttt atatataccc gtgttctctt tttggctagc     540
tagttgcata aaaaataatc tatttttta tcattatttt aaatatctta tgagatggta     600
aatatttatc ataatttttt ttactattat ttattatttg tgtgtgtaat acatatagaa     660
gttaattaca aatttattt acttttttcat tattttgata tgattcacca ttaatttagt     720
gttattattt ataatagttc attttaatct ttttgtatat attatgcgtg cagtacttt      780 ttcctacata taactactat tacattttat ttatataata ttttttattaa tgaattttcg     840 tgataatatg taatattgtt cattattatt tcagattttt taaaaatatt tgtgttatta     900
tttatgaaat atgtaatttt tttagtattt gattttatga tgataaagtg ttctaaattc     960
aaaagaaggg ggaaagcgta acattaaaaa aacgtcatca acaaaaaaca aaatcttgtt    1020
aataaagata aaactgtttg ttttgatcac tgttatttcg taatataaaa acattattta    1080
tatttatatt gttgacaacc aaatttgcct atcaaatcta accaatataa tgcatgcgtg    1140
gcaggtaatg tactaccatg aacttaagtc atgacataat aaaccgtgaa tctgaccaat    1200
gcatgtacct anctaaattg tatttgtgac acgaagcaaa tgattcaatt cacaatggag    1260
atgggaaaca aataatgaag aacccagaac taagaaagct tttctgaaaa ataaaataaa    1320
ggcaatgtca aaagtatact gcatcatcag tccagaaagc acatgatatt ttttttatcag   1380 tatcaatgca gctagtttta ttttacaata tcgatatagc tagtttaaat atattgcagc    1440
tagatttata aatatttgtg ttattattta tcatttgtgt aatcctgttt ttagtatttt    1500
agtttatata tgatgataat gtattccaaa tttaaaagaa gggaaataaa tttaaacaag    1560
aaaaaaagtc atcaaacaaa aaacaaatga aagggtggaa agatgttacc atgtaatgtg    1620
aatgttacag tatttctttt attatagagt taacaaatta actaatatga ttttgttaat    1680
aatgataaaa tatttttttt attattattt cataatataa aaatagttta cttaatataa    1740
```

-continued

```
aaaaaattct atcgttcaca acaaagttgg ccacctaatt taaccatgca tgtacccatg    1800
gaccatatta ggtaaccatc aaacctgatg aagagataaa gagatgaaga cttaagtcat    1860
aacacaaaac cataaaaaac aaaaatacaa tcaaccgtca atctgaccaa tgcatgaaaa    1920
agctgcaata gtgagtggcg acacaaagca catgattttc ttacaacgga gataaaacca    1980
aaaaaatatt tcatgaacaa cctagaacaa ataaagcttt tatataataa atatataaat    2040
aaataaaggc tatggaataa tatacttcaa tatatttgga ttaaataaat tgttggcggg    2100
gttgatatat ttatacacac ctaaagtcac ttcaatctca ttttcactta acttttattt    2160 ttttttttctt tttatttatc ataaagaaa tattgataat atacttttta acatatttt     2220 atgacatttt ttattggtga aaacttatta aaaatcataa attttgtaag ttagatttat    2280
ttaaagagtt cctcttctta ttttaaattt tttaataaat ttttaaataa ctaaatttg     2340 tgttaaaaat gttaaaaaag tgtgttatta acccttctct tcgaggatcc aagcttggcg    2400
cgggccgcca ccgcggtggg gtcgactcta gtaagctttg ctctagatca aactcacatc    2460
caaacataac atggatatct tccttaccaa tcatactaat tattttgggt taaatattaa    2520
tcattatttt taagatatta attaagaaat taaaagattt tttaaaaaaa tgtataaaat    2580
tatattattc atgatttttc atacatttga ttttgataat aaatatattt ttttttaattt  2640 cttaaaaaat gttgcaagac acttattaga catagtcttg ttctgtttac aaaagcattc    2700
atcatttaat acattaaaaa atatttaata ctaacagtag aatcttcttg tgagtggtgt    2760
gggagtaggc aacctggcat tgaaacgaga gaaagagagt cagaaccaga agacaaataa    2820
aaagtatgca acaaacaaat caaaatcaaa gggcaaaggc tggggttggc tcaattggtt    2880
gctacattca atttttcaact cagtcaacgg ttgagattca ctctgacttc cccaatctaa    2940
gccgcggatg caaacggttg aatctaaccc acaatccaat ctcgttactt agggggctttt   3000 ccgtcattaa ctcaccccctg ccaccccggtt tccctataaa ttggaactca atgctccct    3060 ctaaactcgt atcgcttcag agttgagacc aagacacact cgttcatata tctctctgct    3120
cttctcttct cttctacctc tcaaggtact tttcttctcc ctctaccaaa tcctagattc    3180
cgtggttcaa tttcggatct tgcacttctg gtttgctttg ccttgctttt tcctcaactg    3240
ggtccatcta ggatccatgt gaaactctac tctttcttta atatctgcgg aatacgcgtt    3300
ggactttcag atcagtcga aatcatttca taattgcctt tctttctttt agcttatgag     3360
aaataaaatc acttttttttt tatttcaaaa taaaccttgg gccttgtgct gactgagatg    3420
gggtttggtg attacagaat tttagcgaat tttgtaattg tacttgtttg tctgtagttt    3480
tgttttgttt tcttgtttct catacattcc ttaggcttca attttattcg agtataggtc    3540
acaataggaa ttcaaacttt gagcagggga attaatccct tccttcaaat ccagtttgtt    3600
tgtatatatg tttaaaaaat gaaacttttg ctttaaattc tattataact ttttttatgg    3660
ctgaaatttt tgcatgtgtc tttgctctct gttgtaaatt tactgtttag gtactaactc    3720
taggcttgtt gtgcagtttt tgaagtataa ccatgccaca caacacaatg gcggccaccg    3780
cttccagaac cacccgattc tcttcttcct cttcacaccc caccttcccc aaacgcatta    3840
ctagatccac cctccctctc tctcatcaaa ccctcaccaa acccaaccac gctctcaaaa    3900
tcaaatgttc catctccaaa cccccacacg cggcgccctt caccaaggaa cgccgaccca    3960
cggagccctt cgtgtcacgg ttcgcctccg gcgaacctcg caagggcgcg gacatccttg    4020
tggaggcgct ggagaggcag ggcgtgacga cggtgttcgc gtaccccggc ggtgcgtcga    4080
tggagatcca ccaggcgctc acgcgctccg ccgccatccg caacgtgctc ccgcgccacg    4140
```

-continued

```
agcagggcgg cgtcttcgcc gccgaaggct acgcgcgttc ctccggcctc cccggcgtct   4200
gcattgccac ctccggcccc ggcgccacca acctcgtgag cggcctcgcc gacgctttaa   4260
tggacagcgt cccagtcgtc gccatcaccg gccaggtcgc ccgccggatg atcggcaccg   4320
acgccttcca agaaaccccg atcgtggagg tgagcagatc catcacgaag cacaactacc   4380
tcatcctcga cgtcgacgac atccccgcg ctgtcgccga ggctttcttc gtcgccacct   4440
ccggccgccc cggtccggtc ctcatcgaca ttcccaaaga cgttcagcag caactcgccg   4500
tgcctaattg ggacgagccc gttaacctcc ccggttacct cgccaggctg cccaggcccc   4560
ccgccgaggc ccaattggaa cacattgtca gactcatcat ggaggcccaa aagcccgttc   4620
tctacgtcgg cggtggcagt ttgaattcca gtgctgaatt gaggcgcttt gttgaactca   4680
ctggtattcc cgttgctagc actttaatgg gtcttggaac ttttcctatt ggtgatgaat   4740
attcccttca gatgctgggt atgcatggta ctgtttatgc taactatgct gttgacaata   4800
gtgatttgtt gcttgccttt ggggtaaggt ttgatgaccg tgttactggg aagcttgagg   4860
cttttgctag tagggctaag attgttcaca ttgatattga ttctgccgag attgggaaga   4920
acaagcaggc gcacgtgtcg gtttgcgcgg atttgaagtt ggccttgaag ggaattaata   4980
tgattttgga ggagaaagga gtggagggta agtttgatct tggaggttgg agagaagaga   5040
ttaatgtgca gaaacacaag tttccattgg gttacaagac attccaggac gcgatttctc   5100
cgcagcatgc tatcgaggtt cttgatgagt tgactaatgg agatgctatt gttagtactg   5160
gggttgggca gcatcaaatg tgggctgcgc agttttacaa gtacaagaga ccgaggcagt   5220
ggttgacctc aggggtctt ggagccatgg gttttggatt gcctgcggct attggtgctg   5280
ctgttgctaa ccctggggct gttgtggttg acattgatgg ggatggtagt ttcatcatga   5340
atgttcagga gttggccact ataagagtgg agaatctccc agttaagata ttgttgttga   5400
acaatcagca tttgggtatg gtggttcagt tggaggatag gttctacaag tccaatagag   5460
ctcacaccta tcttggagat ccgtctagcg agagcgagat attcccaaac atgctcaagt   5520
ttgctgatgc ttgtgggata ccggcagcgc gagtgacgaa gaaggaagag cttagagcgg   5580
caattcagag aatgttggac accctggcc cctaccttct tgatgtcatt gtgccccatc   5640
aggagcatgt gttgccgatg attcccagta atggatcctt caaggatgtg ataactgagg   5700
gtgatggtag aacgaggtac tgattgccta gaccaaatgt tccttgatgc ttgttttgta   5760
caatatatat aagataatgc tgtcctagtt gcaggatttg gcctgtggtg agcatcatag   5820
tctgtagtag ttttggtagc aagacatttt attttccttt tatttaactt actacatgca   5880
gtagcatcta tctatctctg tagtctgata tctcctgttg tctgtattgt gccgttggat   5940
tttttgctgt agtgagactg aaaatgatgt gctagtaata atatttctgt tagaaatcta   6000
agtagagaat ctgttgaaga agtcaaaagc taatggaatc aggttacata tcaatgttt    6060 tctttttta gcggttggta gacgtgtaga ttcaacttct cttggagctc acctaggcaa    6120
tcagtaaaat gcatattcct tttttaactt gccatttatt tacttttagt ggaaattgtg   6180
accaatttgt tcatgtagaa cggatttgga ccattgcgtc cacaaaacgt ctcttttgct   6240
cgatcttcac aaagcgatac cgaaatccag agatagtttt caaagtcag aaatggcaaa    6300 gttataaata gtaaaacaga atagatgctg taatcgactt caataacaag tggcatcacg   6360
tttctagttc tagacccggg tac                                          6383
```

<210> SEQ ID NO 12

<211> LENGTH: 656
<212> TYPE: PRT
<213> ORGANISM: Artificial Sequence
<220> FEATURE:
<223> OTHER INFORMATION: Mutant soybean ALS

<400> SEQUENCE: 12

```
Met Pro His Asn Thr Met Ala Ala Thr Ala Ser Arg Thr Thr Arg Phe
1               5                   10                  15

Ser Ser Ser Ser Ser His Pro Thr Phe Pro Lys Arg Ile Thr Arg Ser
            20                  25                  30

Thr Leu Pro Leu Ser His Gln Thr Leu Thr Lys Pro Asn His Ala Leu
        35                  40                  45

Lys Ile Lys Cys Ser Ile Ser Lys Pro Pro Thr Ala Ala Pro Phe Thr
    50                  55                  60

Lys Glu Ala Pro Thr Thr Glu Pro Phe Val Ser Arg Phe Ala Ser Gly
65                  70                  75                  80

Glu Pro Arg Lys Gly Ala Asp Ile Leu Val Glu Ala Leu Glu Arg Gln
                85                  90                  95

Gly Val Thr Thr Val Phe Ala Tyr Pro Gly Gly Ala Ser Met Glu Ile
            100                 105                 110

His Gln Ala Leu Thr Arg Ser Ala Ala Ile Arg Asn Val Leu Pro Arg
        115                 120                 125

His Glu Gln Gly Gly Val Phe Ala Ala Glu Gly Tyr Ala Arg Ser Ser
    130                 135                 140

Gly Leu Pro Gly Val Cys Ile Ala Thr Ser Gly Pro Gly Ala Thr Asn
145                 150                 155                 160

Leu Val Ser Gly Leu Ala Asp Ala Leu Met Asp Ser Val Pro Val Val
                165                 170                 175

Ala Ile Thr Gly Gln Val Ala Arg Arg Met Ile Gly Thr Asp Ala Phe
            180                 185                 190

Gln Glu Thr Pro Ile Val Glu Val Ser Arg Ser Ile Thr Lys His Asn
        195                 200                 205

Tyr Leu Ile Leu Asp Val Asp Asp Ile Pro Arg Val Val Ala Glu Ala
    210                 215                 220

Phe Phe Val Ala Thr Ser Gly Arg Pro Gly Pro Val Leu Ile Asp Ile
225                 230                 235                 240

Pro Lys Asp Val Gln Gln Gln Leu Ala Val Pro Asn Trp Asp Glu Pro
                245                 250                 255

Val Asn Leu Pro Gly Tyr Leu Ala Arg Leu Pro Arg Pro Pro Ala Glu
            260                 265                 270

Ala Gln Leu Glu His Ile Val Arg Leu Ile Met Glu Ala Gln Lys Pro
        275                 280                 285

Val Leu Tyr Val Gly Gly Gly Ser Leu Asn Ser Ser Ala Glu Leu Arg
    290                 295                 300

Arg Phe Val Glu Leu Thr Gly Ile Pro Val Ala Ser Thr Leu Met Gly
305                 310                 315                 320

Leu Gly Thr Phe Pro Ile Gly Asp Glu Tyr Ser Leu Gln Met Leu Gly
                325                 330                 335

Met His Gly Thr Val Tyr Ala Asn Tyr Ala Val Asp Asn Ser Asp Leu
            340                 345                 350

Leu Leu Ala Phe Gly Val Arg Phe Asp Asp Arg Val Thr Gly Lys Leu
        355                 360                 365

Glu Ala Phe Ala Ser Arg Ala Lys Ile Val His Ile Asp Ile Asp Ser
    370                 375                 380
```

| Ala | Glu | Ile | Gly | Lys | Asn | Lys | Gln | Ala | His | Val | Ser | Val | Cys | Ala | Asp |
| 385 | | | | 390 | | | | | 395 | | | | | | 400 |

| Leu | Lys | Leu | Ala | Leu | Lys | Gly | Ile | Asn | Met | Ile | Leu | Glu | Glu | Lys | Gly |
| | | | | 405 | | | | | 410 | | | | | 415 | |

| Val | Glu | Gly | Lys | Phe | Asp | Leu | Gly | Gly | Trp | Arg | Glu | Glu | Ile | Asn | Val |
| | | | 420 | | | | | 425 | | | | | 430 | | |

| Gln | Lys | His | Lys | Phe | Pro | Leu | Gly | Tyr | Lys | Thr | Phe | Gln | Asp | Ala | Ile |
| | | | 435 | | | | | 440 | | | | | 445 | | |

| Ser | Pro | Gln | His | Ala | Ile | Glu | Val | Leu | Asp | Glu | Leu | Thr | Asn | Gly | Asp |
| | 450 | | | | | 455 | | | | | 460 | | | | |

| Ala | Ile | Val | Ser | Thr | Gly | Val | Gly | Gln | His | Gln | Met | Trp | Ala | Ala | Gln |
| 465 | | | | 470 | | | | | 475 | | | | | | 480 |

| Phe | Tyr | Lys | Tyr | Lys | Arg | Pro | Arg | Gln | Trp | Leu | Thr | Ser | Gly | Gly | Leu |
| | | | | 485 | | | | | 490 | | | | | 495 | |

| Gly | Ala | Met | Gly | Phe | Gly | Leu | Pro | Ala | Ala | Ile | Gly | Ala | Ala | Val | Ala |
| | | | 500 | | | | | 505 | | | | | 510 | | |

| Asn | Pro | Gly | Ala | Val | Val | Asp | Ile | Asp | Gly | Asp | Gly | Ser | Phe | Ile |
| | | 515 | | | | 520 | | | | | 525 | | | | |

| Met | Asn | Val | Gln | Glu | Leu | Ala | Thr | Ile | Arg | Val | Glu | Asn | Leu | Pro | Val |
| | 530 | | | | | 535 | | | | | 540 | | | | |

| Lys | Ile | Leu | Leu | Leu | Asn | Asn | Gln | His | Leu | Gly | Met | Val | Val | Gln | Leu |
| 545 | | | | | 550 | | | | | 555 | | | | | 560 |

| Glu | Asp | Arg | Phe | Tyr | Lys | Ser | Asn | Arg | Ala | His | Thr | Tyr | Leu | Gly | Asp |
| | | | | 565 | | | | | 570 | | | | | 575 | |

| Pro | Ser | Ser | Glu | Ser | Glu | Ile | Phe | Pro | Asn | Met | Leu | Lys | Phe | Ala | Asp |
| | | | 580 | | | | | 585 | | | | | 590 | | |

| Ala | Cys | Gly | Ile | Pro | Ala | Ala | Arg | Val | Thr | Lys | Lys | Glu | Glu | Leu | Arg |
| | | 595 | | | | | 600 | | | | | 605 | | | |

| Ala | Ala | Ile | Gln | Arg | Met | Leu | Asp | Thr | Pro | Gly | Pro | Tyr | Leu | Leu | Asp |
| 610 | | | | | 615 | | | | | 620 | | | | | |

| Val | Ile | Val | Pro | His | Gln | Glu | His | Val | Leu | Pro | Met | Ile | Pro | Ser | Asn |
| 625 | | | | | 630 | | | | | 635 | | | | | 640 |

| Gly | Ser | Phe | Lys | Asp | Val | Ile | Thr | Glu | Gly | Asp | Gly | Arg | Thr | Arg | Tyr |
| | | | | 645 | | | | | 650 | | | | | 655 | |

<210> SEQ ID NO 13
<211> LENGTH: 8966
<212> TYPE: DNA
<213> ORGANISM: Artificial Sequence
<220> FEATURE:
<223> OTHER INFORMATION: Plasmid pKS210
<220> FEATURE:
<221> NAME/KEY: misc_feature
<222> LOCATION: (1177)..(1177)
<223> OTHER INFORMATION: n is a, c, g, or t

<400> SEQUENCE: 13

| gatcctcgaa gagaagggtt aataacacat tttttaacat ttttaacaca aattttagtt | 60 |
| atttaaaaat ttattaaaaa atttaaaata agaagaggaa ctctttaaat aaatctaact | 120 |
| tacaaaattt atgattttta ataagttttc accaataaaa aatgtcataa aaatatgtta | 180 |
| aaagtatat tatcaatatt ctctttatga taaataaaaa gaaaaaaaaa ataaagtta | 240 |
| agtgaaaatg agattgaagt gactttaggt gtgtataaat atatcaaccc cgccaacaat | 300 |
| ttatttaatc caaatatatt gaagtatatt attccatagc ctttatttat ttatatattt | 360 |
| attatataaa agcttttattt gttctaggtt gttcatgaaa tatttttttg gttttatctc | 420 |

```
cgttgtaaga aaatcatgtg ctttgtgtcg ccactcacta ttgcagcttt ttcatgcatt      480
ggtcagattg acggttgatt gtattttgt tttttatggt tttgtgttat gacttaagtc       540
ttcatctctt tatctcttca tcaggtttga tggttaccta atatggtcca tgggtacatg      600
catggttaaa ttaggtggcc aactttgttg tgaacgatag aatttttttt atattaagta      660 aactatttt atattatgaa ataataataa aaaaaatatt ttatcattat taacaaaatc       720
atattagtta atttgttaac tctataataa aagaaatact gtaacattca cattacatgg      780
taacatcttt ccacccttc atttgttttt tgtttgatga cttttttct tgtttaaatt        840 tatttccctt cttttaaatt tggaatacat tatcatcata tataaactaa aatactaaaa      900
acaggattac acaaatgata aataataaca caaatattta taaatctagc tgcaatatat     960
ttaaactagc tatatcgata ttgtaaaata aaactagctg cattgatact gataaaaaaa     1020
tatcatgtgc tttctggact gatgatgcag tatacttttg acattgcctt tattttattt    1080
ttcagaaaag ctttcttagt tctgggttct tcattatttg tttcccatct ccattgtgaa    1140
ttgaatcatt tgcttcgtgt cacaaataca atttagntag gtacatgcat tggtcagatt    1200
cacggtttat tatgtcatga cttaagttca tggtagtaca ttacctgcca cgcatgcatt    1260
atattggtta gatttgatag gcaaatttgg ttgtcaacaa tataaatata aataatgttt    1320
ttatattacg aaataacagt gatcaaaaca aacagtttta tctttattaa caagattttg    1380
tttttgtttg atgacgtttt ttaatgttta cgctttcccc cttcttttga atttagaaca    1440
ctttatcatc ataaaatcaa atactaaaaa aattacatat tcataaaata ataacacaaa    1500
tatttttaaa aaatctgaaa taataatgaa caatattaca tattatcacg aaaattcatt    1560
aataaaaata ttatataaat aaaatgtaat agtagttata tgtaggaaaa aagtactgca    1620
cgcataatat atacaaaaag attaaaatga actattataa ataataacac taaattaatg    1680
gtgaatcata tcaaaataat gaaaagtaa ataaaatttg taattaactt ctatatgtat     1740
tacacacaca aataataaat aatagtaaaa aaaattatga taaatattta ccatctcata    1800
agatatttaa aataatgata aaaatataga ttattttta tgcaactagc tagccaaaaa     1860
gagaacacgg gtatatataa aaagagtacc tttaaattct actgtacttc ctttattcct    1920
gacgttttta tatcaagtgg acatacgtga agattttaat tatcagtcta aatatttcat    1980
tagcacttaa tacttttctg ttttattcct atcctataag tagtcccgat tctcccaaca    2040
ttgcttattc acacaactaa ctaagaaagt cttccatagc cccccaagcg gccggagctg    2100
gtcatctcgc tcatcgtcga gtcggcggcc ggagctggtc atctcgctca tcgtcgagtc    2160
ggcggccgcc gactcgacga tgagcgagat gaccagctcc ggccgccgac tcgacgatga    2220
gcgagatgac cagctccggc gcgacacaa gtgtgagagt actaaataaa tgctttggtt     2280
gtacgaaatc attacactaa ataaaataat caaagcttat atatgccttc cgctaaggcc    2340
gaatgcaaag aaattggttc tttctcgtta tcttttgcca cttttactag tacgtattaa    2400
ttactactta atcatctttg tttacggctc attatatccg tcgacggcgc gcccgatcat    2460
ccggatatag ttcctccttt cagcaaaaaa cccctcaaga cccgtttaga ggccccaagg    2520
ggttatgcta gttattgctc agcggtggca gcagccaact cagcttcctt tcgggctttg    2580
ttagcagccg gatcgatcca agctgtacct cactattcct ttgccctcgg acgagtgctg    2640
gggcgtcggt ttccactatc ggcgagtact tctacacagc catcggtcca gacggccgcg    2700
cttctgcggg cgatttgtgt acgcccgaca gtcccggctc cggatcggac gattgcgtcg    2760
```

```
catcgaccct gcgcccaagc tgcatcatcg aaattgccgt caaccaagct ctgatagagt   2820
tggtcaagac caatgcggag catatacgcc cggagccgcg gcgatcctgc aagctccgga   2880
tgcctccgct cgaagtagcg cgtctgctgc tccatacaag ccaaccacgg cctccagaag   2940
aagatgttgg cgacctcgta ttgggaatcc ccgaacatcg cctcgctcca gtcaatgacc   3000
gctgttatgc ggccattgtc cgtcaggaca ttgttggagc cgaaatccgc gtgcacgagg   3060
tgccggactt cggggcagtc ctcggcccaa agcatcagct catcgagagc ctgcgcgacg   3120
gacgcactga cggtgtcgtc catcacagtt tgccagtgat acacatgggg atcagcaatc   3180
gcgcatatga aatcacgcca tgtagtgtat tgaccgattc cttgcggtcc gaatgggccg   3240
aacccgctcg tctggctaag atcggccgca gcgatcgcat ccatagcctc gcgaccggc    3300 tgcagaacag cgggcagttc ggtttcaggc aggtcttgca acgtgacacc ctgtgcacgg   3360
cgggagatgc aataggtcag gctctcgctg aattccccaa tgtcaagcac ttccggaatc   3420
gggagcgcgg ccgatgcaaa gtgccgataa acataacgat ctttgtagaa accatcggcg   3480
cagctattta cccgcaggac atatccacgc cctcctacat cgaagctgaa agcacgagat   3540
tcttcgccct ccgagagctg catcaggtcg agacgctgt cgaactttc gatcagaaac     3600 ttctcgacag acgtcgcggt gagttcaggc ttttccatgg gtatatctcc ttcttaaagt   3660
taaacaaaat tatttctaga gggaaaccgt tgtggtctcc ctatagtgag tcgtattaat   3720
ttcgcgggat cgagatctga tcaacctgca ttaatgaatc ggccaacgcg cggggagagg   3780
cggtttgcgt attgggcgct cttccgcttc ctcgctcact gactcgctgc gctcggtcgt   3840
tcggctgcgg cgagcggtat cagctcactc aaaggcggta atacggttat ccacagaatc   3900
aggggataac gcaggaaaga acatgtgagc aaaaggccag caaaaggcca ggaaccgtaa   3960
aaaggccgcg ttgctggcgt ttttccatag gctccgcccc cctgacgagc atcacaaaaa   4020
tcgacgctca gtcagaggt ggcgaaaccc gacaggacta taaagatacc aggcgtttcc     4080
ccctggaagc tccctcgtgc gctctcctgt tccgaccctg ccgcttaccg gatacctgtc   4140
cgcctttctc ccttcgggaa gcgtggcgct ttctcaatgc tcacgctgta ggtatctcag   4200
ttcggtgtag gtcgttcgct ccaagctggg ctgtgtgcac gaacccccg ttcagcccga     4260 ccgctgcgcc ttatccggta actatcgtct tgagtccaac ccggtaagac acgacttatc   4320
gccactggca gcagccactg gtaacaggat tagcagagcg aggtatgtag gcggtgctac   4380
agagttcttg aagtggtggc ctaactacgg ctacactaga aggacagtat ttggtatctg   4440
cgctctgctg aagccagtta ccttcggaaa aagagttggt agctcttgat ccggcaaaca   4500
aaccaccgct ggtagcggtg ttttttttgt ttgcaagcag cagattacgc gcagaaaaaa   4560
aggatctcaa gaagatcctt tgatctttc tacggggtct gacgctcagt ggaacgaaaa     4620
ctcacgttaa gggattttgg tcatgacatt aacctataaa aataggcgta tcacgaggcc   4680
ctttcgtctc gcgcgtttcg gtgatgacgg tgaaaacctc tgacacatgc agctcccgga   4740
gacggtcaca gcttgtctgt aagcggatgc cgggagcaga caagcccgtc agggcgcgtc   4800
agcgggtgtt ggcgggtgtc ggggctggct taactatgcg gcatcagagc agattgtact   4860
gagagtgcac catatggaca tattgtcgtt agaacgcggc tacaattaat acataacctt   4920
atgtatcata cacatacgat ttaggtgaca ctatagaacg gcgcgccaag cttggatccg   4980
cgccaagctt ggatcctaga actagaaacg tgatgccact tgttattgaa gtcgattaca   5040
gcatctattc tgttttacta tttataactt tgccatttct gacttttgaa aactatctct   5100
ggatttcggt atcgctttgt gaagatcgag caaaagagac gttttgtgga cgcaatggtc   5160
```

```
caaatccgtt ctacatgaac aaattggtca caatttccac taaaagtaaa taaatggcaa      5220
gttaaaaaag gaatatgcat tttactgatt gcctaggtga gctccaagag aagttgaatc      5280
tacacgtcta ccaaccgcta aaaaagaaa aacattgata tgtaacctga ttccattagc      5340
ttttgacttc ttcaacagat tctctactta gatttctaac agaaatatta ttactagcac      5400
atcattttca gtctcactac agcaaaaaat ccaacggcac aatacagaca acaggagata      5460
tcagactaca gagatagata gatgctactg catgtagtaa gttaaataaa aggaaaataa      5520
aatgtcttgc taccaaaact actacagact atgatgctca ccacaggcca aatcctgcaa      5580
ctaggacagc attatcttat atatattgta caaaacaagc atcaaggaac atttggtcta      5640
ggcaatcagt acctcgttct accatcaccc tcagttatca catccttgaa ggatccatta      5700
ctgggaatca tcggcaacac atgctcctga tggggcacaa tgacatcaag aaggtagggg      5760
ccaggggtgt ccaacattct ctgaattgcc gctctaagct cttccttctt cgtcactcgc      5820
gctgccggta tcccacaagc atcagcaaac ttgagcatgt ttgggaatat ctcgctctcg      5880
ctagacggat ctccaagata ggtgtgagct ctattggact tgtagaacct atcctccaac      5940
tgaaccacca tacccaaatg ctgattgttc aacaacaata tcttaactgg gagattctcc      6000
actcttatag tggccaactc ctgaacattc atgatgaaac taccatcccc atcaatgtca      6060
accacaacag ccccagggtt agcaacagca gcaccaatag ccgcaggcaa tccaaaaccc      6120
atggctccaa gaccccctga ggtcaaccac tgcctcggtc tcttgtactt gtaaaactgc      6180
gcagcccaca tttgatgctg cccaaccca gtactaacaa tagcatctcc attagtcaac      6240
tcatcaagaa cctcgatagc atgctgcgga gaaatcgcgt cctggaatgt cttgtaaccc      6300
aatgaaaact tgtgtttctg cacattaatc tcttctctcc aacctccaag atcaaactta      6360
ccctccactc ctttctcctc caaaatcata ttaattccct tcaaggccaa cttcaaatcc      6420
gcgcaaaccg acacgtgcgc ctgcttgttc ttcccaatct cggcagaatc aatatcaatg      6480
tgaacaatct tagccctact agcaaaagcc tcaagcttcc cagtaacacg gtcatcaaac      6540
cttaccccaa aggcaagcaa caaatcacta ttgtcaacag catagttagc ataaacagta      6600
ccatgcatac ccagcatctg aagggaatat tcatcaccaa taggaaaagt tccaagaccc      6660
attaaagtgc tagcaacggg aataccagtg agttcaacaa agcgcctcaa ttcagcactg      6720
gaattcaaac tgccaccgcc gacgtagaga acgggctttt gggcctccat gatgagtctg      6780
acaatgtgtt ccaattgggc ctcggcgggg ggcctgggca gcctggcgag gtaaccgggg      6840
aggttaacgg gctcgtccca attaggcacg gcgagttgct gctgaacgtc tttgggaatg      6900
tcgatgagga ccggaccggg gcggccggag gtggcgacga agaaagcctc ggcgacgacg      6960
cgggggatgt cgtcgacgtc gaggatgagg tagttgtgct tcgtgatgga tctgctcacc      7020
tccacgatcg gggtttcttg gaaggcgtcg gtgccgatca tccggcgggc gacctggccg      7080
gtgatggcga cgactgggac gctgtccatt aaagcgtcgg cgaggccgct cacgaggttg      7140
gtggcgccgg ggccggaggt ggcaatgcag acgccgggga ggccgaggga acgcgcgtag      7200
ccttcggcgg cgaagacgcc gccctgctcg tggcgcggga gcacgttgcg gatggcggcg      7260
gagcgcgtga gcgcctggtg gatctccatc gacgcaccgc cggggtacgc gaacaccgtc      7320
gtcacgccct gcctctccag cgcctccaca aggatgtccg cgcccttgcg aggttcgccg      7380
gaggcgaacc gtgacacgaa gggctccgtg gtcggcgctt ccttggtgaa gggcgccgcc      7440 gtgggggggtt tggagatgga acatttgatt ttgagagcgt ggttgggttt ggtgagggtt      7500
```

```
tgatgagaga gagggagggt ggatctagta atgcgtttgg ggaaggtggg gtgtgaagag    7560
gaagaagaga atcgggtggt tctggaagcg gtggccgcca ttgtgttgtg tggcatggtt    7620
atacttcaaa aactgcacaa caagcctaga gttagtacct aaacagtaaa tttacaacag    7680
agagcaaaga cacatgcaaa aatttcagcc ataaaaaaag ttataataga atttaaagca    7740
aaagtttcat tttttaaaca tatatacaaa caaactggat ttgaaggaag ggattaattc    7800
ccctgctcaa agtttgaatt cctattgtga cctatactcg aataaaattg aagcctaagg    7860
aatgtatgag aaacaagaaa acaaacaaa actacagaca aacaagtaca attacaaaat    7920
tcgctaaaat tctgtaatca ccaaacccca tctcagtcag cacaaggccc aaggtttatt    7980
ttgaaataaa aaaaagtga tttatttct cataagctaa agaagagaaa ggcaattatg    8040
aaatgatttc gactagatct gaaagtccaa cgcgtattcc gcagatatta agaaagagt    8100 agagtttcac atggatccta gatggaccca gttgaggaaa aagcaaggca agcaaaacca    8160
gaagtgcaag atccgaaatt gaaccacgga atctaggatt tggtagaggg agaagaaaag    8220
taccttgaga ggtagaagag aagagaagag cagagagata tatgaacgag tgtgtcttgg    8280
tctcaactct gaagcgatac gagtttagag gggagcattg agttccaatt tataggaaa    8340 ccgggtggca ggggtgagtt aatgacggaa aagcccctaa gtaacgagat tggattgtgg    8400
gttagattca accgtttgca tccgcggctt agattgggga agtcagagtg aatctcaacc    8460
gttgactgag ttgaaaattg aatgtagcaa ccaattgagc caaccccagc ctttgccctt    8520
tgattttgat ttgtttgttg catacttttt atttgtcttc tggttctgac tctcttctc    8580 tcgtttcaat gccaggttgc ctactcccac accactcaca agaagattct actgttagta    8640
ttaaatattt tttaatgtat taatgatga atgcttttgt aaacagaaca agactatgtc    8700
taataagtgt cttgcaacat ttttaagaa attaaaaaaa atatatttat tatcaaaatc    8760
aaatgtatga aaaatcatga ataatataat tttatacatt tttttaaaaa atctttaat    8820 ttcttaatta atatcttaaa aataatgatt aatatttaac ccaaaataat tagtatgatt    8880
ggtaaggaag atatccatgt tatgtttgga tgtgagtttg atctagagca aagcttacta    8940
gagtcgaccg atccgtcgac ggcgcg                                         8966
```

<210> SEQ ID NO 14
<211> LENGTH: 40
<212> TYPE: DNA
<213> ORGANISM: Artificial Sequence
<220> FEATURE:
<223> OTHER INFORMATION: Oligonucleotide primer BM5

<400> SEQUENCE: 14
gccggggtac cggcgcgccc gatcatccgg atatagttcc                40

<210> SEQ ID NO 15
<211> LENGTH: 40
<212> TYPE: DNA
<213> ORGANISM: Artificial Sequence
<220> FEATURE:
<223> OTHER INFORMATION: Oligonucleotide primer BM6

<400> SEQUENCE: 15
gccggggtac cggcgcgccg ttctatagtg tcacctaatc                40

<210> SEQ ID NO 16
<211> LENGTH: 8911
<212> TYPE: DNA
<213> ORGANISM: Artificial Sequence
<220> FEATURE:
<223> OTHER INFORMATION: Plasmid pDN10
<220> FEATURE:
<221> NAME/KEY: misc_feature
<222> LOCATION: (3740)..(3740)
<223> OTHER INFORMATION: n is a, c, g, or t

<400> SEQUENCE: 16

| | | | | | |
|---|---|---|---|---|---|
| cggcgcgccc | gatcatccgg | atatagttcc | tcctttcagc | aaaaaacccc | tcaagacccg | 60 |
| tttagaggcc | ccaaggggtt | atgctagtta | ttgctcagcg | gtggcagcag | ccaactcagc | 120 |
| ttcctttcgg | gctttgttag | cagccggatc | gatccaagct | gtacctcact | attcctttgc | 180 |
| cctcggacga | gtgctggggc | gtcggtttcc | actatcggcg | agtacttcta | cacagccatc | 240 |
| ggtccagacg | gccgcgcttc | tgcgggcgat | tgtgtacgc | ccgacagtcc | cggctccgga | 300 |
| tcggacgatt | gcgtcgcatc | gaccctgcgc | ccaagctgca | tcatcgaaat | tgccgtcaac | 360 |
| caagctctga | tagagttggt | caagaccaat | gcggagcata | tacgcccgga | gccgcggcga | 420 |
| tcctgcaagc | tccggatgcc | tccgctcgaa | gtagcgcgtc | tgctgctcca | tacaagccaa | 480 |
| ccacggcctc | cagaagaaga | tgttggcgac | ctcgtattgg | gaatcccga | acatcgcctc | 540 |
| gctccagtca | atgaccgctg | ttatgcggcc | attgtccgtc | aggacattgt | tggagccgaa | 600 |
| atccgcgtgc | acgaggtgcc | ggacttcggg | gcagtcctcg | gcccaaagca | tcagctcatc | 660 |
| gagagcctgc | gcgacggacg | cactgacggt | gtcgtccatc | acagtttgcc | agtgatacac | 720 |
| atggggatca | gcaatcgcgc | atatgaaatc | acgccatgta | gtgtattgac | cgattccttg | 780 |
| cggtccgaat | gggccgaacc | cgctcgtctg | gctaagatcg | gccgcagcga | tcgcatccat | 840 |
| agcctccgcg | accggctgca | gaacagcggg | cagttcggtt | tcaggcaggt | cttgcaacgt | 900 |
| gacaccctgt | gcacggcggg | agatgcaata | ggtcaggctc | tcgctgaatt | ccccaatgtc | 960 |
| aagcacttcc | ggaatcggga | gcgcggccga | tgcaaagtgc | cgataaacat | aacgatcttt | 1020 |
| gtagaaacca | tcggcgcagc | tatttacccg | caggacatat | ccacgccctc | ctacatcgaa | 1080 |
| gctgaaagca | cgagattctt | cgccctccga | gagctgcatc | aggtcggaga | cgctgtcgaa | 1140 |
| cttttcgatc | agaaacttct | cgacagacgt | cgcggtgagt | tcaggctttt | ccatgggtat | 1200 |
| atctccttct | taaagttaaa | caaaattatt | tctagaggga | aaccgttgtg | gtctccctat | 1260 |
| agtgagtcgt | attaatttcg | cgggatcgag | atctgatcaa | cctgcattaa | tgaatcggcc | 1320 |
| aacgcgcggg | gagaggcggt | ttgcgtattg | ggcgctcttc | cgcttcctcg | ctcactgact | 1380 |
| cgctgcgctc | ggtcgttcgg | ctgcggcgag | cggtatcagc | tcactcaaag | gcggtaatac | 1440 |
| ggttatccac | agaatcaggg | gataacgcag | gaaagaacat | gtgagcaaaa | ggccagcaaa | 1500 |
| aggccaggaa | ccgtaaaaag | gccgcgttgc | tggcgttttt | ccataggctc | cgccccctg | 1560 |
| acgagcatca | caaaaatcga | cgctcaagtc | agaggtggcg | aaacccgaca | ggactataaa | 1620 |
| gataccaggc | gtttccccct | ggaagctccc | tcgtgcgctc | tcctgttccg | accctgccgc | 1680 |
| ttaccggata | cctgtccgcc | tttctccctt | cgggaagcgt | ggcgctttct | caatgctcac | 1740 |
| gctgtaggta | tctcagttcg | gtgtaggtcg | ttcgctccaa | gctgggctgt | gtgcacgaac | 1800 |
| cccccgttca | gcccgaccgc | tgcgccttat | ccggtaacta | tcgtcttgag | tccaacccgg | 1860 |
| taagacacga | cttatcgcca | ctggcagcag | ccactggtaa | caggattagc | agagcgaggt | 1920 |
| atgtaggcgg | tgctacagag | ttcttgaagt | ggtggcctaa | ctacggctac | actagaagga | 1980 |
| cagtatttgg | tatctgcgct | ctgctgaagc | cagttacctt | cggaaaaaga | gttggtagct | 2040 |
| cttgatccgg | caaacaaacc | accgctggta | gcggtggttt | ttttgtttgc | aagcagcaga | 2100 |

```
ttacgcgcag aaaaaaagga tctcaagaag atcctttgat cttttctacg gggtctgacg   2160
ctcagtggaa cgaaaactca cgttaaggga ttttggtcat gacattaacc tataaaaata   2220
ggcgtatcac gaggcccttt cgtctcgcgc gtttcggtga tgacggtgaa aacctctgac   2280
acatgcagct cccggagacg gtcacagctt gtctgtaagc ggatgccggg agcagacaag   2340
cccgtcaggg cgcgtcagcg ggtgttggcg ggtgtcgggg ctggcttaac tatgcggcat   2400
cagagcagat tgtactgaga gtgcaccata tggacatatt gtcgttagaa cgcggctaca   2460
attaatacat aaccttatgt atcatacaca tacgatttag gtgacactat agaacggcgc   2520
gccggtaccg ggccccccct cgaggtcgac ggtatcgata agcttgatat cgaattcctg   2580
cagcccgggg gatccactag ttctagagcg gcccgcgccg tcgacggata taatgagccg   2640
taaacaaaga tgattaagta gtaattaata cgtactagta aaagtggcaa aagataacga   2700
gaaagaacca atttctttgc attcggcctt agcggaaggc atatataagc tttgattatt   2760
ttatttagtg taatgatttc gtacaaccaa agcatttatt tagtactctc acacttgtgt   2820
cgcggccgct tgggggggcta tggaagactt tcttagttag ttgtgtgaat aagcaatgtt   2880
gggagaatcg ggactactta taggatagga ataaaacaga aaagtattaa gtgctaatga   2940
aatatttaga ctgataatta aaatcttcac gtatgtccac ttgatataaa aacgtcagga   3000
ataaaggaag tacagtagaa tttaaaggta ctctttttat atatacccgt gttctctttt   3060
tggctagcta gttgcataaa aaataatcta tattttatc attattttaa atatcttatg   3120
agatggtaaa tatttatcat aattttttt actattattt attatttgtg tgtgtaatac   3180
atatagaagt taattacaaa ttttatttac tttttcatta ttttgatatg attccacatt   3240
aatttagtgt tattatttat aatagttcat tttaatcttt ttgtatatat tatgcgtgca   3300 gtacttttt cctacatata actactatta cattttattt atataatatt tttattaatg   3360
aattttcgtg ataatatgta atattgttca ttattatttc agatttttta aaaatatttg   3420
tgttattatt tatgaaatat gtaattttt tagtatttga ttttatgatg ataaagtgtt   3480
ctaaattcaa aagaagggg aaagcgtaaa cattaaaaaa cgtcatcaaa caaaaacaaa   3540
atcttgttaa taaagataaa actgtttgtt ttgatcactg ttatttcgta atataaaaac   3600
attatttata tttatattgt tgacaaccaa atttgcctat caaatctaac caatataatg   3660
catgcgtggc aggtaatgta ctaccatgaa cttaagtcat gacataataa accgtgaatc   3720
tgaccaatgc atgtacctan ctaaattgta tttgtgacac gaagcaaatg attcaattca   3780
caatggagat gggaaacaaa taatgaagaa cccagaacta agaaagcttt tctgaaaaat   3840
aaaataaagg caatgtcaaa agtatactgc atcatcagtc cagaaagcac atgatatttt   3900
tttatcagta tcaatgcagc tagttttatt ttacaatatc gatatagcta gtttaaatat   3960
attgcagcta gatttataaa tatttgtgtt attatttatc atttgtgtaa tcctgttttt   4020 agtatttag tttatatatg atgataatgt attccaaatt taaagaagg gaaataaatt   4080 taaacaagaa aaaagtcat caaacaaaaa acaaatgaaa gggtggaaag atgttaccat   4140
gtaatgtgaa tgttacagta tttctttat tatagagtta acaaattaac taatatgatt   4200
ttgttaataa tgataaaata tttttttttat tattatttca taatataaaa atagtttact   4260 taatatataaa aaaattctat cgttcacaac aaagttggcc acctaatta accatgcatg   4320 tacccatgga ccatattagg taaccatcaa acctgatgaa gagataaaga gatgaagact   4380
taagtcataa cacaaaaccaa taaaaaacaa aaatacaatc aaccgtcaat ctgaccaatg   4440
catgaaaaag ctgcaatagt gagtggcgac acaaagcaca tgattttctt acaacggaga   4500
```

```
taaaaccaaa aaaatatttc atgaacaacc tagaacaaat aaagctttta tataataaat      4560
atataaataa ataaaggcta tggaataata tacttcaata tatttggatt aaataaattg      4620
ttggcggggt tgatatattt atacacacct aaagtcactt caatctcatt ttcacttaac      4680 ttttatttt ttttttcttt tatttatcat aaagagaata ttgataatat acttttaac       4740 atattttat gacatttttt attggtgaaa acttattaaa aatcataaat tttgtaagtt       4800
agatttattt aaagagttcc tcttcttatt ttaaatttt taataaattt ttaaataact       4860
aaaatttgtg ttaaaaatgt taaaaaagtg tgttattaac ccttctcttc gaggatccaa      4920
gcttggcgcg ggccgccacc gcggtggggt cgactctagt aagctttgct ctagatcaaa      4980
ctcacatcca aacataacat ggatatcttc cttaccaatc atactaatta ttttgggtta     5040
aatattaatc attattttta agatattaat taagaaatta aaagattttt taaaaaaatg    5100
tataaaatta tattattcat gattttcat acatttgatt ttgataataa atatattttt      5160
tttaatttct taaaaaatgt tgcaagacac ttattagaca tagtcttgtt ctgtttacaa     5220
aagcattcat catttaatac attaaaaaat atttaatact aacagtagaa tcttcttgtg     5280
agtggtgtgg gagtaggcaa cctggcattg aaacgagaga aagagagtca gaaccagaag     5340
acaaataaaa agtatgcaac aaacaaatca aaatcaaagg gcaaaggctg gggttggctc     5400
aattggttgc tacattcaat tttcaactca gtcaacggtt gagattcact ctgacttccc      5460
caatctaagc cgcggatgca aacggttgaa tctaacccac aatccaatct cgttacttag     5520
gggcttttcc gtcattaact cacccctgcc acccggtttc cctataaatt ggaactcaat     5580
gctcccctct aaactcgtat cgcttcagag ttgagaccaa gacacactcg ttcatatatc     5640
tctctgctct tctcttctct tctacctctc aaggtacttt tcttctccct ctaccaaatc     5700
ctagattccg tggttcaatt tcggatcttg cacttctggt ttgctttgcc ttgcttttc      5760 ctcaactggg tccatctagg atccatgtga aactctactc tttctttaat atctgcggaa     5820
tacgcgttgg actttcagat ctagtcgaaa tcatttcata attgcctttc tttcttttag     5880
cttatgagaa ataaaatcac ttttttttta tttcaaaata aaccttgggc cttgtgctga     5940
ctgagatggg gtttggtgat tacagaattt tagcgaattt tgtaattgta cttgtttgtc     6000
tgtagttttg ttttgttttc ttgtttctca tacattcctt aggcttcaat tttattcgag      6060
tataggtcac aataggaatt caaactttga gcaggggaat taatcccttc cttcaaatcc     6120
agtttgtttg tatatatgtt taaaaaatga aacttttgct ttaaattcta ttataacttt     6180
ttttatggct gaaatttttg catgtgtctt tgctctctgt tgtaaattta ctgtttaggt     6240
actaactcta ggcttgttgt gcagttttg aagtataacc atgccacaca acacaatggc      6300
ggccaccgct tccagaacca cccgattctc ttcttcctct tcacacccca ccttcccaa      6360 acgcattact agatccaccc tccctctctc tcatcaaacc ctcaccaaac ccaaccacgc     6420
tctcaaaatc aaatgttcca tctccaaacc ccccacggcg gcgcccttca ccaaggaagc    6480
gccgaccacg gagcccttcg tgtcacggtt cgcctccggc gaacctcgca agggcgcgga    6540
catccttgtg gaggcgctgg agaggcaggg cgtgacgacg gtgttcgcgt accccggcgg    6600
tgcgtcgatg gagatccacc aggcgctcac gcgctccgcc gccatccgca acgtgctccc    6660
gcgccacgag cagggcggcg tcttcgccgc cgaaggctac gcgcgttcct ccggcctccc    6720
cggcgtctgc attgccacct ccggcccegg cgccaccaac ctcgtgagcg gcctcgccga    6780
cgctttaatg gacagcgtcc cagtcgtcgc catcaccggc caggtcgccc gccggatgat    6840
```

```
cggcaccgac gccttccaag aaacccgat cgtggaggtg agcagatcca tcacgaagca    6900
caactacctc atcctcgacg tcgacgacat ccccgcgtc gtcgccgagg ctttcttcgt    6960
cgccacctcc ggccgccccg tccggtcct catcgacatt cccaaagacg ttcagcagca    7020
actcgccgtg cctaattggg acgagcccgt taacctcccc ggttacctcg ccaggctgcc    7080
caggcccccc gccgaggccc aattggaaca cattgtcaga ctcatcatgg aggcccaaaa    7140
gcccgttctc tacgtcggcg gtggcagttt gaattccagt gctgaattga ggcgctttgt    7200
tgaactcact ggtattcccg ttgctagcac tttaatgggt cttggaactt ttcctattgg    7260
tgatgaatat tcccttcaga tgctgggtat gcatggtact gtttatgcta actatgctgt    7320
tgacaatagt gatttgttgc ttgcctttgg ggtaaggttt gatgaccgtg ttactgggaa    7380
gcttgaggct tttgctagta gggctaagat tgttcacatt gatattgatt ctgccgagat    7440
tgggaagaac aagcaggcgc acgtgtcggt ttgcgcggat ttgaagttgg ccttgaaggg    7500
aattaatatg attttggagg agaaggagt ggagggtaag tttgatcttg gaggttggag    7560
agaagagatt aatgtgcaga acacaagtt tccattgggt tacaagacat tccaggacgc    7620
gatttctccg cagcatgcta tcgaggttct tgatgagttg actaatggag atgctattgt    7680
tagtactggg gttgggcagc atcaaatgtg ggctgcgcag ttttacaagt acaagagacc    7740
gaggcagtgg ttgaccctcag ggggtcttgg agccatgggt tttggattgc ctgcggctat    7800
tggtgctgct gttgctaacc ctgggggctgt tgtggttgac attgatgggg atggtagttt    7860
catcatgaat gttcaggagt tggccactat aagagtggga aatctcccag ttaagatatt    7920
gttgttgaac aatcagcatt tgggtatggt ggttcagttg gaggataggt tctacaagtc    7980
caatagagct cacacctatc ttggagatcc gtctagcgag agcgagatat tcccaaacat    8040
gctcaagttt gctgatgctt gtgggatacc ggcagcgcga gtgacgaaga aggaagagct    8100
tagagcggca attcagagaa tgttggacac ccctggcccc taccttcttg atgtcattgt    8160
gccccatcag gagcatgtgt tgccgatgat tcccagtaat ggatccttca aggatgtgat    8220
aactgagggt gatggtagaa cgaggtactg attgcctaga ccaaatgttc cttgatgctt    8280
gttttgtaca atatatataa gataatgctg tcctagttgc aggatttggc ctgtggtgag    8340
catcatagtc tgtagtagtt ttggtagcaa gacattttat tttccttta tttaacttac    8400 tacatgcagt agcatctatc tatctctgta gtctgatatc tcctgttgtc tgtattgtgc    8460
cgttggattt tttgctgtag tgagactgaa aatgatgtgc tagtaataat atttctgtta    8520
gaaatctaag tagagaatct gttgaagaag tcaaaagcta atggaatcag gttacatatc    8580 aatgttttc ttttttagc ggttggtaga cgtgtagatt caacttctct tggagctcac    8640
ctaggcaatc agtaaaatgc atattccttt tttaacttgc catttattta cttttagtgg    8700
aaattgtgac caatttgttc atgtagaacg gatttggacc attgcgtcca caaaacgtct    8760
cttttgctcg atcttcacaa agcgataccg aaatccagag atagttttca aaagtcagaa    8820
atggcaaagt tataaatagt aaaacagaat agatgctgta atcgacttca ataacaagtg    8880
gcatcacgtt tctagttcta gacccgggta c                                  8911
```

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide primer BM7

<400> SEQUENCE: 17

```
gcggccgcat gtggaggctg aagatagcag                                        30

<210> SEQ ID NO 18
<211> LENGTH: 31
<212> TYPE: DNA
<213> ORGANISM: Artificial Sequence
<220> FEATURE:
<223> OTHER INFORMATION: Oligonucleotide primer BM8

<400> SEQUENCE: 18
gcggccgctt aaacttcagt ggaaggcaat g                                      31

<210> SEQ ID NO 19
<211> LENGTH: 2305
<212> TYPE: DNA
<213> ORGANISM: Artificial Sequence
<220> FEATURE:
<223> OTHER INFORMATION: Amplification product obtained from clone
      src3c.pk024.m11 using primers BM7 and BM8

<400> SEQUENCE: 19
gcggccgcat gtggaggctg aagatagcag atggaggaaa tgatccatac atattcagca       60
caaacaattt cgttgggagg cagacatggg agtttgatcc tgaagcaggc agtccagagg      120
aacgggccca ggttgaagca gctcgtcagc atttctacca caaccgcttc aaggtcaagc      180
cctgcgctga cctcctttgg cgttttcagg ttctcagaga aataacttc aaacaaacaa       240 ttcctcgtgt gactatagaa gatggagagg aaatcacata ccaaaaagtc acaagcgccg      300
tcagaagggg cgcacaccac cttgcggcac tgcagacctc tgatggccat tggcctgctc      360
aaattgcagg tcctctcttc tttcttcctc ccttggtttt ttgtatgtat attacaggaa      420
atcttgaatc agtatttcca gaagaacatc gcaaagaaat tcttcgttac acatattatc      480
accagaatga agacggagga tggggactac acatagaggg tcatagcact atgttttgta      540
ctgcactgaa ctatatatgc atgcgaatgc ttggagaagg acctaatgga ggtcatgaca      600
atgcttgtgc tagagcaaga aagtggattc gagatcatgg tggtgtaaca catatacctt      660
catggggaaa aacttggctt tcgatactcg gtgtatttga ttggtgcgga agcaacccaa      720
tgcccccaga gttttggatc cttccatctt ttcttcctat gcatccagct aagatgtggt      780
gttactgtcg attggtatac atgcctatgt cttacttata tgggaagagg tttgtgggtc      840
caatcacacc actcatctta caattaagag aagagttgtt tactcaacct tatgaaaaag      900
ttaattggaa gaaagcgcgt caccaatgtg caaaggaaga tctttactat ccccatcctt      960
tgatacaaga cctaatatgg gatagtttat acatattcac tgaaccgcta cttactcgtt     1020
ggcctttcaa caagttgatt agagaaaagg cccttcaagt aactatgaaa catattcatt     1080
atgaagatga gactagtcga tacataacca ttggttgtgt ggaaaaggtt ttatgtatgc     1140
ttgcttgttg ggtggaagat ccaaacggag atgctttcaa gaagcatctt gcaagggtcc     1200
cagattactt atgggtttct gaagatggaa tgaccatgca gagttttggt agccaagaat     1260
gggatgctgg ctttgctgtt caagctttgc ttgccactaa cataattgaa gaaattggtc     1320
ctacgtttgc aaaaggacat gatttcatca gaagtctca ggtgaaggat aatccttttg      1380
gagattttaa aagtatgcat cgtcatattt ctaaagggtc ttggacattc tctgatcaag     1440
accatggatg gcaagttttct gattgcactg cagaaggttt aaagtgttgt ctacttctat     1500
caatgttgcc accagagatt gtgggagaaa agatggaacc tgaaagatta tacgattcag     1560
tcaatgtctt gttgtcgctt cagagtaaaa aaggtggttt agcagcatgg gagcctgcag     1620
```

```
gagctcaaga gtggttagaa ttactcaatc ccacagaatt ttttgcggac attgtagttg      1680
aacatgaata tgttgagtgc actggatctg caatccaagc tttagttttg ttcaagaagc      1740
tatatccagg acataggaag aaagagatag aaaatttcat taccaatgca gttcgattcc      1800
ttgaagatac acaaacagct gatggttcat ggtatggaaa ttggggagtt tgcttcactt      1860
atggctcttg gtttgcactt ggaggtctag cagctgctgg taagacttac accaattgtg      1920
ctgccattcg caaagccgtt aaatttctac ttacaacaca agagaggac ggtggatggg       1980 gagagagtta tctttcaagc ccaaaaaaga tatatgtacc tctagaagga agccgatcaa      2040
atgttgtaca tacagcatgg gctcttatgg gactaattca tgctggacag gcggatagag      2100
accccatgcc tcttcaccgt gctgcaaagt tgctcattaa ttctcagttg gaagagggtg      2160
attggcccca acaggaaatc acgggagtat tcatgaaaaa ttgcatgttg cattatccaa      2220
tgtacagaga tatttatcca atgtgggctc tagctgaata tcgaaggcgg gttccattgc      2280
cttccactga agtttaagcg gccgc                                            2305

<210> SEQ ID NO 20
<211> LENGTH: 11208
<212> TYPE: DNA
<213> ORGANISM: Artificial Sequence
<220> FEATURE:
<223> OTHER INFORMATION: plasmid PHP20767
<220> FEATURE:
<221> NAME/KEY: misc_feature
<222> LOCATION: (6037)..(6037)
<223> OTHER INFORMATION: n is a, c, g, or t

<400> SEQUENCE: 20
cggcgcgccc gatcatccgg atatagttcc tcctttcagc aaaaaacccc tcaagacccg        60
tttagaggcc ccaagggggtt atgctagtta ttgctcagcg gtggcagcag ccaactcagc      120
ttcctttcgg gctttgttag cagccggatc gatccaagct gtacctcact attcctttgc      180
cctcggacga gtgctggggc gtcggtttcc actatcggcg agtacttcta cacagccatc      240
ggtccagacg gccgcgcttc tgcgggcgat ttgtgtacgc ccgacagtcc cggctccgga      300
tcggacgatt gcgtcgcatc gaccctgcgc ccaagctgca tcatcgaaat tgccgtcaac      360
caagctctga tagagttggt caagaccaat gcggagcata tacgcccgga gccgcggcga      420
tcctgcaagc tccggatgcc tccgctcgaa gtagcgcgtc tgctgctcca tacaagccaa      480
ccacggcctc cagaagaaga tgttggcgac ctcgtattgg gaatccccga catcgcctc      540 gctccagtca atgaccgctg ttatgcggcc attgtccgtc aggacattgt tggagccgaa      600
atccgcgtgc acgaggtgcc ggacttcggg gcagtcctcg gcccaaagca tcagctcatc      660
gagagcctgc gcgacggacg cactgacggt gtcgtccatc acagtttgcc agtgatacac      720
atggggatca gcaatcgcgc atatgaaatc acgccatgta gtgtattgac cgattccttg      780
cggtccgaat gggccgaacc cgctcgtctg gctaagatcg gccgcagcga tcgcatccat      840
agcctccgcg accggctgca gaacagcggg cagttcggtt tcaggcaggt cttgcaacgt      900
gacaccctgt gcacggcggg agatgcaata ggtcaggctc tcgctgaatt ccccaatgtc      960
aagcacttcc ggaatcggga gcgcggccga tgcaaagtgc cgataaacat aacgatcttt     1020
gtagaaacca tcggcgcagc tatttacccg caggacatat ccacgccctc ctacatcgaa     1080
gctgaaagca cgagattctt cgccctccga gagctgcatc aggtcggaga cgctgtcgaa     1140
cttttcgatc agaaacttct cgacagacgt cgcggtgagt tcaggctttt ccatgggtat     1200
```

```
atctccttct taaagttaaa caaaattatt tctagaggga aaccgttgtg gtctccctat    1260
agtgagtcgt attaatttcg cgggatcgag atctgatcaa cctgcattaa tgaatcggcc    1320
aacgcgcggg gagaggcggt ttgcgtattg ggcgctcttc cgcttcctcg ctcactgact    1380
cgctgcgctc ggtcgttcgg ctgcggcgag cggtatcagc tcactcaaag gcggtaatac    1440
ggttatccac agaatcaggg gataacgcag gaaagaacat gtgagcaaaa ggccagcaaa    1500
aggccaggaa ccgtaaaaag gccgcgttgc tggcgttttt ccataggctc cgcccccctg    1560
acgagcatca caaaaatcga cgctcaagtc agaggtggcg aaacccgaca ggactataaa    1620
gataccaggc gtttccccct ggaagctccc tcgtgcgctc tcctgttccg accctgccgc    1680
ttaccggata cctgtccgcc tttctccctt cgggaagcgt ggcgctttct caatgctcac    1740
gctgtaggta tctcagttcg gtgtaggtcg ttcgctccaa gctgggctgt gtgcacgaac    1800
cccccgttca gcccgaccgc tgcgccttat ccggtaacta tcgtcttgag tccaacccgg    1860
taagacacga cttatcgcca ctggcagcag ccactggtaa caggattagc agagcgaggt    1920
atgtaggcgg tgctacagag ttcttgaagt ggtggcctaa ctacggctac actagaagga    1980
cagtatttgg tatctgcgct ctgctgaagc cagttacctt cggaaaaaga gttggtagct    2040
cttgatccgg caaacaaacc accgctggta gcggtggttt ttttgtttgc aagcagcaga    2100
ttacgcgcag aaaaaaagga tctcaagaag atcctttgat cttttctacg ggtctgacg    2160 ctcagtggaa cgaaaactca cgttaaggga ttttggtcat gacattaacc tataaaaata    2220
ggcgtatcac gaggcccttt cgtctcgcgc gtttcggtga tgacggtgaa aacctctgac    2280
acatgcagct cccggagacg gtcacagctt gtctgtaagc ggatgccggg agcagacaag    2340
cccgtcaggg cgcgtcagcg ggtgttggcg ggtgtcgggg ctggcttaac tatgcggcat    2400
cagagcagat tgtactgaga gtgcaccata tggacatatt gtcgttagaa cgcggctaca    2460
attaatacat aaccttatgt atcatacaca tacgatttag gtgacactat agaacggcgc    2520
gccggtaccg ggccccccct cgaggtcgac ggtatcgata agcttgatat cgaattcctg    2580
cagcccgggg gatccactag ttctagagcg gccgcgccg tcgacggata taatgagccg    2640
taaacaaaga tgattaagta gtaattaata cgtactagta aaagtggcaa aagataacga    2700
gaaagaacca atttctttgc attcggcctt agcggaaggc atatataagc tttgattatt    2760
ttatttagtg taatgatttc gtacaaccaa agcatttatt tagtactctc acacttgtgt    2820
cgcggccgct taaacttcag tggaaggcaa tggaacccgc cttcgatatt cagctagagc    2880
ccacattgga taaatatctc tgtacattgg ataatgcaac atgcaatttt tcatgaatac    2940
tcccgtgatt tcctgttggg gccaatcacc ctcttccaac tgagaattaa tgagcaactt    3000
tgcagcacgg tgaagaggca tggggtctct atccgcctgt ccagcatgaa ttagtcccat    3060
aagagcccat gctgtatgta caacatttga tcggcttcct tctagaggta catatatctt    3120
ttttgggctt gaaagataac tctctcccca tccaccgtcc tctctttgtg ttgtaagtag    3180
aaatttaacg gctttgcgaa tggcagcaca attggtgtaa gtcttaccag cagctgctag    3240
acctccaagt gcaaaccaag agccataagt gaagcaaact ccccaatttc cataccatga    3300
accatcagct gtttgtgtat cttcaaggaa tcgaactgca ttggtaatga aattttctat    3360
ctctttcttc ctatgtcctg gatatagctt cttgaacaaa actaaagctt ggattgcaga    3420
tccagtgcac tcaacatatt catgttcaac tacaatgtcc gcaaaaaatt ctgtgggatt    3480
gagtaattct aaccactctt gagctcctgc aggctcccat gctgctaaac caccttttt    3540 actctgaagc gacaacaaga cattgactga atcgtataat ctttcaggtt ccatcttttc    3600
```

```
tcccacaatc tctggtggca acattgatag aagtagacaa cactttaaac cttctgcagt    3660
gcaatcagaa acttgccatc catggtcttg atcagagaat gtccaagacc ctttagaaat    3720
atgacgatgc atacttttaa aatctccaaa aggattatcc ttcacctgag acttcttgat    3780
gaaatcatgt cctttgcaa acgtaggacc aatttcttca attatgttag tggcaagcaa     3840
agcttgaaca gcaaagccag catcccattc ttggctacca aaactctgca tggtcattcc    3900
atcttcagaa acccataagt aatctgggac ccttgcaaga tgcttcttga aagcatctcc    3960
gtttggatct tccacccaac aagcaagcat acataaaacc ttttccacac aaccaatggt    4020
tatgtatcga ctagtctcat cttcataatg aatatgtttc atagttactt gaagggcctt    4080
ttctctaatc aacttgttga aaggccaacg agtaagtagc ggttcagtga atatgtataa    4140
actatcccat attaggtctt gtatcaaagg atggggatag taaagatctt cctttgcaca    4200
ttggtgacgc gctttcttcc aattaacttt ttcataaggt tgagtaaaca actcttctct    4260
taattgtaag atgagtggtg tgattggacc cacaaacctc ttcccatata agtaagacat    4320
aggcatgtat accaatcgac agtaacacca catcttagct ggatgcatag gaagaaaaga    4380
tggaaggatc caaaactctg ggggcattgg gttgcttccg caccaatcaa atacaccgag    4440
tatcgaaagc caagttttc cccatgaagg tatatgtgtt acaccaccat gatctcgaat     4500
ccactttctt gctctagcac aagcattgtc atgacctcca ttaggtcctt ctccaagcat    4560
tcgcatgcat atatagttca gtgcagtaca aaacatagtg ctatgaccct ctatgtgtag    4620
tccccatcct ccgtcttcat tctggtgata atatgtgtaa cgaagaattt ctttgcgatg    4680
ttcttctgga aatactgatt caagatttcc tgtaatatac atacaaaaaa ccaagggagg    4740
aagaaagaag agaggacctg caatttgagc aggccaatgg ccatcagagg tctgcagtgc    4800
cgcaaggtgg tgtgcgcccc ttctgacggc gcttgtgact ttttggtatg tgatttcctc    4860
tccatcttct atagtcacac gaggaattgt ttgtttgaag ttattttctc tgagaacctg    4920
aaaacgccaa aggaggtcag cgcagggctt gaccttgaag cggttgtggt agaaatgctg    4980
acgagctgct tcaacctggg cccgttcctc tggactgcct gcttcaggat caaactccca    5040
tgtctgcctc ccaacgaaat tgtttgtgct gaatatgtat ggatcatttc ctccatctgc    5100
tatcttcagc ctccacatgc ggccgcttgg ggggctatgg aagactttct tagttagttg    5160
tgtgaataag caatgttggg agaatcggga ctacttatag gataggaata aaacagaaaa    5220
gtattaagtg ctaatgaaat atttagactg ataattaaaa tcttcacgta tgtccacttg    5280
atataaaaac gtcaggaata aaggaagtac agtagaattt aaaggtactc ttttatata    5340
tacccgtgtt ctcttttttgg ctagctagtt gcataaaaaa taatctatat ttttatcatt    5400
attttaaata tcttatgaga tggtaaatat ttatcataat tttttttact attatttatt    5460
atttgtgtgt gtaatacata tagaagttaa ttacaaattt tatttacttt ttcattattt    5520
tgatatgatt caccattaat ttagtgttat tatttataat agttcatttt aatcttttg     5580
tatatattat gcgtgcagta cttttttcct acatataact actattacat tttatttata    5640
taatattttt attaatgaat tttcgtgata atatgtaata ttgttcatta ttatttcaga    5700
ttttttaaaa atatttgtgt tattattat gaaatatgta attttttag tatttgattt      5760
tatgatgata aagtgttcta aattcaaaag aagggggaaa gcgtaaacat taaaaaacgt    5820
catcaaacaa aaacaaaatc ttgttaataa agataaaact gtttgttttg atcactgtta    5880
tttcgtaata taaaaacatt atttatattt atattgttga caaccaaatt tgcctatcaa    5940
```

```
atctaaccaa tataatgcat gcgtggcagg taatgtacta ccatgaactt aagtcatgac    6000
ataataaacc gtgaatctga ccaatgcatg tacctancta aattgtattt gtgacacgaa    6060
gcaaatgatt caattcacaa tggagatggg aaacaaataa tgaagaaccc agaactaaga    6120
aagcttttct gaaaaataaa ataaaggcaa tgtcaaaagt atactgcatc atcagtccag    6180
aaagcacatg atatttttt atcagtatca atgcagctag ttttatttta caatatcgat     6240
atagctagtt taaatatatt gcagctagat ttataaatat ttgtgttatt atttatcatt    6300
tgtgtaatcc tgtttttagt attttagttt atatatgatg ataatgtatt ccaaatttaa    6360
aagaagggaa ataaatttaa acaagaaaaa aagtcatcaa acaaaaaaca aatgaaaggg    6420
tggaaagatg ttaccatgta atgtgaatgt tacagtcattt cttttattat agagttaaca   6480
aattaactaa tatgattttg ttaataatga taaaatatttt tttttattat tatttcataa   6540
tataaaaata gtttacttaa tataaaaaaa attctatcgt tcacaacaaa gttggccacc    6600
taatttaacc atgcatgtac ccatggacca tattaggtaa ccatcaaacc tgatgaagag    6660
ataaagagat gaagacttaa gtcataacac aaaaccataa aaaacaaaaa tacaatcaac    6720
cgtcaatctg accaatgcat gaaaaagctg caatagtgag tggcgacaca aagcacatga    6780
ttttcttaca acggagataa aaccaaaaaa atatttcatg aacaacctag aacaaataaa    6840
gcttttatat aataaatata taaataaata aaggctatgg aataatatac ttcaatatat    6900
ttggattaaa taaattgttg gcggggttga tatatttata cacacctaaa gtcacttcaa    6960
tctcattttc acttaacttt tatttttttt ttcttttat ttatcataaa gagaatattg     7020
ataatatact ttttaacata tttttatgac attttttatt ggtgaaaact tattaaaaat    7080
cataaatttt gtaagttaga tttatttaaa gagttcctct tcttatttta aattttttaa    7140
taaattttta aataactaaa atttgtgtta aaaatgttaa aaaagtgtgt tattaaccct    7200
tctcttcgag gatccaagct tggcgcgggc cgccaccgcg gtggggtcga ctctagtaag    7260
ctttgctcta gatcaaactc acatccaaac ataacatgga tatcttcctt accaatcata    7320
ctaattattt tgggttaaat attaatcatt attttttaaga tattaattaa gaaattaaaa   7380
gattttttaa aaaaatgtat aaaattatat tattcatgat ttttcataca tttgattttg    7440
ataataaata tattttttt aatttcttaa aaaatgttgc aagacactta ttagacatag     7500
tcttgttctg tttacaaaag cattcatcat ttaatacatt aaaaaatatt taatactaac    7560
agtagaatct tcttgtgagt ggtgtgggag taggcaacct ggcattgaaa cgagagaaag    7620
agagtcagaa ccagaagaca aataaaaagt atgcaacaaa caaatcaaaa tcaagggca    7680 aaggctgggg ttggctcaat tggttgctac attcaatttt caactcagtc aacggttgag    7740
attcactctg acttccccaa tctaagccgc ggatgcaaac ggttgaatct aacccacaat    7800
ccaatctcgt tacttagggg cttttccgtc attaactcac ccctgccacc cggtttccct    7860
ataaattgga actcaatgct cccctctaaa ctcgtatcgc ttcagagttg agaccaagac    7920
acactcgttc atatatctct ctgctcttct cttctcttct acctctcaag gtacttttct    7980
tctccctcta ccaaatccta gattccgtgg ttcaatttcg gatcttgcac ttctggttttg    8040 ctttgccttg cttttcctc aactgggtcc atctaggatc catgtgaaac tctactcttt     8100
ctttaatatc tgcggaatac gcgttggact ttcagatcta gtcgaaatca tttcataatt    8160
gcctttcttt cttttagctt atgagaaata aaatcacttt tttttatttt caaaataaac    8220
cttgggcctt gtgctgactg agatgggggt tggtgattac agaatttttag cgaatttgt    8280 aattgtactt gtttgtctgt agttttgttt tgttttcttg tttctcatac attccttagg    8340
```

```
cttcaattttt attcgagtat aggtcacaat aggaattcaa actttgagca ggggaattaa    8400
tcccttcctt caaatccagt tgtttgtat atatgtttaa aaaatgaaac ttttgcttta    8460
aattctatta taactttttt tatggctgaa attttttgcat gtgtctttgc tctctgttgt   8520
aaatttactg tttaggtact aactctaggc ttgttgtgca gtttttgaag tataaccatg    8580
ccacacaaca caatggcggc caccgcttcc agaaccaccc gattctcttc ttcctcttca    8640
cacccccacct tccccaaacg cattactaga tccaccctcc ctctctctca tcaaaccctc   8700
accaaaccca accacgctct caaaatcaaa tgttccatct ccaaaccccc cacggcggcg    8760
cccttcacca aggaagcgcc gaccacggag cccttcgtgt cacggttcgc ctccggcgaa    8820
cctcgcaagg gcgcggacat ccttgtggag gcgctggaga ggcagggcgt gacgacggtg    8880
ttcgcgtacc ccggcggtgc gtcgatggag atccaccagg cgctcacgcg ctccgccgcc    8940
atccgcaacg tgctcccgcg ccacgagcag ggcggcgtct tcgccgccga aggctacgcg    9000
cgttcctccg gcctccccgg cgtctgcatt gccacctccg gccccggcgc caccaacctc    9060
gtgagcggcc tcgccgacgc tttaatggac agcgtcccag tcgtcgccat caccggccag    9120
gtcgcccgcc ggatgatcgg caccgacgcc ttccaagaaa ccccgatcgt ggaggtgagc    9180
agatccatca cgaagcacaa ctacctcatc ctcgacgtcg acgacatccc ccgcgtcgtc    9240
gccgaggctt tcttcgtcgc cacctccggc cgccccggtc cggtcctcat cgacattccc    9300
aaagacgttc agcagcaact cgccgtgcct aattgggacg agcccgttaa cctccccggt    9360
tacctcgcca ggctgcccag gccccccgcc gaggcccaat tggaacacat tgtcagactc    9420
atcatggagg cccaaaagcc cgttctctac gtcggcggtg gcagtttgaa ttccagtgct    9480
gaattgaggc gctttgttga actcactggt attcccgttg ctagcacttt aatgggtctt    9540
ggaacttttc ctattggtga tgaatattcc cttcagatgc tgggtatgca tggtactgtt    9600
tatgctaact atgctgttga caatagtgat ttgttgcttg cctttggggt aaggtttgat   9660
gaccgtgtta ctgggaagct tgaggctttt gctagtaggg ctaagattgt tcacattgat    9720
attgattctg ccgagattgg gaagaacaag caggcgcacg tgtcggtttg cgcggatttg    9780
aagttggcct tgaagggaat taatatgatt ttggaggaga aaggagtgga gggtaagttt    9840
gatcttggag gttggagaga agagattaat gtgcagaaac acaagtttcc attgggttac    9900
aagacattcc aggacgcgat ttctccgcag catgctatcg aggttcttga tgagttgact    9960
aatgagatg ctattgttag tactggggtt gggcagcatc aaatgtgggc tgcgcagttt    10020
tacaagtaca agagaccgag gcagtggttg acctcagggg gtcttggagc catgggtttt    10080
ggattgcctg cggctattgg tgctgctgtt gctaaccctg gggctgttgt ggttgacatt    10140
gatggggatg gtagtttcat catgaatgtt caggagttgg ccactataag agtggagaat    10200
ctcccagtta agatattgtt gttgaacaat cagcatttgg gtatggtggt tcagttggag    10260
gataggttct acaagtccaa tagagctcac acctatcttg gagatccgtc tagcgagagc    10320
gagatattcc caaacatgct caagtttgct gatgcttgtg ggataccggc agcgcgagtg    10380
acgaagaagg aagagcttag agcggcaatt cagagaatgt tggacacccc tggcccctac    10440
cttcttgatg tcattgtgcc ccatcaggag catgtgttgc cgatgattcc cagtaatgga    10500
tccttcaagg atgtgataac tgagggtgat ggtagaacga ggtactgatt gcctagacca    10560
aatgttcctt gatgcttgtt ttgtacaata tatataagat aatgctgtcc tagttgcagg    10620
atttggcctg tggtgagcat catagtctgt agtagttttg gtagcaagac attttatttt    10680
```

-continued

```
cctttattt  aacttactac  atgcagtagc  atctatctat  ctctgtagtc  tgatatctcc   10740
tgttgtctgt  attgtgccgt  tggattttt   gctgtagtga  gactgaaaat  gatgtgctag   10800
taataatatt  tctgttagaa  atcaagtag   agaatctgtt  gaagaagtca  aaagctaatg   10860
gaatcaggtt  acatatcaat  gttttctt    ttttagcggt  tggtagacgt  gtagattcaa   10920
cttctcttgg  agctcaccta  ggcaatcagt  aaaatgcata  ttccttttt   aacttgccat   10980
ttatttactt  ttagtggaaa  ttgtgaccaa  tttgttcatg  tagaacggat  ttggaccatt   11040
gcgtccacaa  aacgtctctt  ttgctcgatc  ttcacaaagc  gataccgaaa  tccagagata   11100
gttttcaaaa  gtcagaaatg  gcaaagttat  aaatagtaaa  acagaataga  tgctgtaatc   11160
gacttcaata  acaagtggca  tcacgtttct  agttctagac  ccgggtac                11208
```

<210> SEQ ID NO 21
<211> LENGTH: 27
<212> TYPE: DNA
<213> ORGANISM: Artificial Sequence
<220> FEATURE:
<223> OTHER INFORMATION: Oligonucleotide primer BM9

<400> SEQUENCE: 21
gcggccgcga attttttgcg gacattg                                            27

<210> SEQ ID NO 22
<211> LENGTH: 31
<212> TYPE: DNA
<213> ORGANISM: Artificial Sequence
<220> FEATURE:
<223> OTHER INFORMATION: Oligonucleotide primer BM10

<400> SEQUENCE: 22
ggaaacttac gacattaaac ttcagtggaa g                                       31

<210> SEQ ID NO 23
<211> LENGTH: 31
<212> TYPE: DNA
<213> ORGANISM: Artificial Sequence
<220> FEATURE:
<223> OTHER INFORMATION: Oligonucleotide primer BM11

<400> SEQUENCE: 23
cttccactga agtttaatgt cgtaagtttc c                                       31

<210> SEQ ID NO 24
<211> LENGTH: 29
<212> TYPE: DNA
<213> ORGANISM: Artificial Sequence
<220> FEATURE:
<223> OTHER INFORMATION: Oligonucleotide primer BM12

<400> SEQUENCE: 24
taagaaaaag tcctacatac ccaaaattg                                          29

<210> SEQ ID NO 25
<211> LENGTH: 1800
<212> TYPE: DNA
<213> ORGANISM: Glycine max
<220> FEATURE:
<221> NAME/KEY: misc_feature
<222> LOCATION: (1)..(1800)
<223> OTHER INFORMATION: Genomic fragment used to amplify IFS intron

<400> SEQUENCE: 25
tgctggaact tgcacttggt tgtttgtgt tagctttgtt tctgcacttg cgtcccacac          60

-continued

```
caagtgcaaa atcaaaagca cttcgccacc tcccaaaccc tccaagccca aagcctcgtc    120
ttcccttcat tggccacctt cacctcttaa aagataaact tctccactat gcactcatcg    180
atctctccaa aaagcatggc cccttattct ctctctcctt cggctccatg ccaaccgtcg    240
ttgcctccac ccctgagttg ttcaagctct tcctccaaac ccacgaggca acttccttca    300
acacaaggtt ccaaacctct gccataagac gcctcactta cgacaactct gtggccatgg    360
ttccattcgg accttactgg aagttcgtga ggaagctcat catgaacgac cttctcaacg    420
ccaccaccgt caacaagctc aggcctttga ggacccaaca gatccgcaag ttccttaggg    480
ttatggccca aagcgcagag gcccagaagc cccttgacgt caccgaggag cttctcaaat    540
ggaccaacag caccatctcc atgatgatgc tcggcgaggc tgaggagatc agagacatcg    600
ctcgcgaggt tcttaagatc ttcggcgaat acagcctcac tgacttcatc tggcctttga    660
agtatctcaa ggttggaaag tatgagaaga ggattgatga catcttgaac aagttcgacc    720
ctgtcgttga aagggtcatc aagaagcgcc gtgagatcgt cagaaggaga agaacggag    780 aagttgttga gggcgaggcc agcggcgtct cctcgacac tttgcttgaa ttcgctgagg    840
acgagaccat ggagatcaaa attaccaagg agcaaatcaa gggccttgtt gtcgtaagtt    900
tccttcttct ctcctacttt attactttct ttcattcatc atatgtattg cattaaata    960 gtatactata tgagaaaata tgttacgcac tcacggtgta agatatgtg gtgttttttt    1020 aaaaagagat acagaagttg ctttatgca tgtatgttaa cgtatattta ctcaagtgga    1080
aactaattaa ttctcaattt tgggtatgta ggacttttc tctgcaggga cagattccac    1140
agcggtggca acagagtggg cattggcaga gctcatcaac aatcccaggg tgttgcaaaa    1200
ggctcgtgag gaggtctaca gtgttgtggg caaagataga ctcgttgacg aagttgacac    1260
tcaaaacctt ccttacatta gggccattgt gaaggagaca ttccgaatgc acccaccact    1320
cccagtggtc aaaagaaagt gcacagaaga gtgtgagatt aatgggtatg tgatcccaga    1380
gggagcattg gttctttca atgtttggca agtaggaagg gaccccaaat actgggacag    1440
accatcagaa ttccgtcccg agaggttctt agaaactggt gctgaagggg aagcagggcc    1500
tcttgatctt aggggccagc atttccaact cctcccattt gggtctggga ggagaatgtg    1560
ccctggtgtc aatttggcta cttcaggaat ggcaacactt cttgcatctc ttatccaatg    1620 cttttgacctg caagtgctgg gccctcaagg acaaatattg aaaggtgatg atgccaaagt    1680
tagcatggaa gagagagctg gcctcacagt tccaagggca catagtctcg tttgtgttcc    1740
acttgcaagg atcggcgttg catctaaact cctttcttaa ttaagggatc catcatatac    1800
```

<210> SEQ ID NO 26
<211> LENGTH: 855
<212> TYPE: DNA
<213> ORGANISM: Artificial Sequence
<220> FEATURE:
<223> OTHER INFORMATION: Chimera comprising a portion of src3c.pk024.m11
      and the IFS intron

<400> SEQUENCE: 26

```
gcggccgcga attttttgcg gacattgtag ttgaacatga atatgttgag tgcactggat     60
ctgcaatcca agctttagtt ttgttcaaga agctatatcc aggacatagg aagaaagaga    120
tagaaaattt cattaccaat gcagttcgat tccttgaaga tacacaaaca gctgatggtt    180
catggtatgg aaattgggga gtttgcttca cttatggctc ttggtttgca cttggaggtc    240
tagcagctgc tggtaagact tacaccaatt gtgctgccat tcgcaaagcc gttaaatttc    300
```

```
tacttacaac acaaagagag gacggtggat ggggagagag ttatctttca agcccaaaaa      360
agatatatgt acctctagaa ggaagccgat caaatgttgt acatacagca tgggctctta      420
tgggactaat tcatgctgga caggcggata gagaccccat gcctcttcac cgtgctgcaa      480
agttgctcat taattctcag ttggaagagg gtgattggcc ccaacaggaa atcacgggag      540
tattcatgaa aaattgcatg ttgcattatc caatgtacag agatatttat ccaatgtggg      600
ctctagctga atatcgaagg cgggttccat tgccttccac tgaagtttaa tgtcgtaagt      660
ttccttcttc tctcctactt tattactttc tttcattcat catatgtatt ggcattaaat      720
agtatactat atgagaaaat atgttacgca ctcacggtgt aaagatatgt ggtgtttttt      780
taaaaagaga tacagaagtt gcttttatgc atgtatgtta acgtatattt actcaagtgg      840
aaactaatta attct                                                      855

<210> SEQ ID NO 27
<211> LENGTH: 48
<212> TYPE: DNA
<213> ORGANISM: Artificial Sequence
<220> FEATURE:
<223> OTHER INFORMATION: Oligonucleotide primer BM13

<400> SEQUENCE: 27
ctgcaggggt atgtaggact ttttcttaaa cttcagtgga aggcaatg                   48

<210> SEQ ID NO 28
<211> LENGTH: 35
<212> TYPE: DNA
<213> ORGANISM: Artificial Sequence
<220> FEATURE:
<223> OTHER INFORMATION: Oligonucleotide primer BM14

<400> SEQUENCE: 28
gcggccgcaa ttttttgcgg acattgtagt tgaac                                 35

<210> SEQ ID NO 29
<211> LENGTH: 674
<212> TYPE: DNA
<213> ORGANISM: Artificial Sequence
<220> FEATURE:
<223> OTHER INFORMATION: Complement of the portion of the cDNA insert in
      clone src3c.pk024.m11 used in preparing PHP21157

<400> SEQUENCE: 29
gcggccgcaa ttttttgcgg acattgtagt tgaacatgaa tatgttgagt gcactggatc      60
tgcaatccaa gctttagttt tgttcaagaa gctatatcca ggacatagga agaaagagat     120
agaaaatttc attaccaatg cagttcgatt ccttgaagat acacaaacag ctgatggttc     180
atggtatgga aattggggag tttgcttcac ttatggctct tggtttgcac ttggaggtct     240
agcagctgct ggtaagactt acaccaattg tgctgccatt cgcaaagccg ttaaatttct     300
acttacaaca caaagagagg acggtggatg gggagagagt tatctttcaa gcccaaaaa     360 gatatatgta cctctagaag gaagccgatc aaatgttgta catacagcat gggctcttat     420
gggactaatt catgctggac aggcggatag agaccccatg cctcttcacc gtgctgcaaa     480
gttgctcatt aattctcagt tggaagaggg tgattggccc caacaggaaa tcacgggagt     540
attcatgaaa aattgcatgt tgcattatcc aatgtacaga gatatttatc caatgtgggc     600
tctagctgaa tatcgaaggc gggttccatt gccttccact gaagtttaag aaaaagtcct     660
acatacccct gcag                                                       674
```

<210> SEQ ID NO 30
<211> LENGTH: 10473
<212> TYPE: DNA
<213> ORGANISM: Artificial Sequence
<220> FEATURE:
<223> OTHER INFORMATION: Plasmid PHP21157
<220> FEATURE:
<221> NAME/KEY: misc_feature
<222> LOCATION: (917)..(917)
<223> OTHER INFORMATION: n is a, c, g, or t

<400> SEQUENCE: 30

```
ggccgcttgg gggctatgg  aagactttct  tagttagttg  tgtgaataag  caatgttggg    60
agaatcggga ctacttatag gataggaata aaacagaaaa gtattaagtg ctaatgaaat    120
atttagactg ataattaaaa tcttcacgta tgtccacttg atataaaaac gtcaggaata    180
aaggaagtac agtagaattt aaaggtactc tttttatata tacccgtgtt ctcttttttgg   240
ctagctagtt gcataaaaaa taatctatat tttatcatt  attttaaata tcttatgaga    300
tggtaaatat ttatcataat ttttttttact attattat   atttgtgtgt gtaatacata   360
tagaagttaa ttacaaattt tatttacttt ttcattattt tgatatgatt caccattaat    420
ttagtgttat tatttataat agttcatttt aatcttttg   tatatattat gcgtgcagta   480
cttttttcct acatataact actattacat tttatttata taatattttt attaatgaat    540
tttcgtgata atatgtaata ttgttcatta ttatttcaga ttttttaaaa atatttgtgt    600
tattatttat gaaatatgta attttttag  tatttgattt tatgatgata aagtgttcta    660
aattcaaaag aagggggaaa gcgtaaacat taaaaaacgt catcaaacaa aaacaaaatc    720
ttgttaataa agataaaact gtttgtttg  atcactgtta tttcgtaata taaaaacatt    780
atttatattt atattgttga caaccaaatt tgcctatcaa atctaaccaa tataatgcat    840
gcgtggcagg taatgtacta ccatgaactt aagtcatgac ataataaacc gtgaatctga    900
ccaatgcatg tacctancta aattgtattt gtgacacgaa gcaaatgatt caattcacaa    960
tggagatggg aaacaaataa tgaagaaccc agaactaaga aagcttttct gaaaaataaa   1020
ataaaggcaa tgtcaaaagt atactgcatc atcagtccag aaagcacatg atattttttt   1080
atcagtatca atgcagctag ttttatttta caatatcgat atagctagtt taaatatatt   1140
gcagctagat ttataaatat ttgtgttatt atttatcatt tgtgtaatcc tgtttttagt   1200
attttagttt atatatgatg ataatgtatt ccaaatttaa aagaagggaa ataaatttaa   1260
acaagaaaaa aagtcatcaa acaaaaaaca aatgaaaggg tggaaagatg ttaccatgta   1320
atgtgaatgt tacagtattt cttttattat agagttaaca aattaactaa tatgattttg   1380
ttaataatga taaaatattt ttttattat  tatttcataa tataaaaata gtttacttaa   1440
tataaaaaaa attctatcgt tcacaacaaa gttggccacc taatttaacc atgcatgtac   1500
ccatggacca tattaggtaa ccatcaaacc tgatgaagag ataaagagat gaagacttaa   1560
gtcataacac aaaaccataa aaaacaaaaa tacaatcaac cgtcaatctg accaatgcat   1620
gaaaaagctg caatagtgag tggcgacaca aagcacatga ttttcttaca acggagataa   1680
aaccaaaaaa atatttcatg aacaacctag aacaaataaa gctttatat  aataaatata   1740
taaataaata aaggctatgg aataatatac ttcaatatat ttggattaaa taaattgttg   1800
gcggggttga tatatttata cacacctaaa gtcacttcaa tctcatttttc acttaacttt   1860
tatttttttt ttcttttttat ttatcataaa gagaatattg ataatatact ttttaacata  1920
```

```
tttttatgac attttttatt ggtgaaaact tattaaaaat cataaatttt gtaagttaga      1980
tttatttaaa gagttcctct tcttatttta aatttttta  taaattttta aataactaaa      2040
atttgtgtta aaaatgttaa aaaagtgtgt tattaaccct tctcttcgag gatccaagct      2100
tggcgcgggc cgccaccgcg gtgggtcga  ctctagtaag ctttgctcta gatcaaactc      2160
acatccaaac ataacatgga tatcttcctt accaatcata ctaattattt tgggttaaat      2220
attaatcatt attttaaga  tattaattaa gaaattaaaa gattttttaa aaaaatgtat      2280
aaaattatat tattcatgat ttttcataca tttgattttg ataataaata tatttttttt      2340
aatttcttaa aaaatgttgc aagacactta ttagacatag tcttgttctg tttacaaaag      2400
cattcatcat ttaatacatt aaaaaatatt taatactaac agtagaatct tcttgtgagt      2460
ggtgtgggag taggcaacct ggcattgaaa cgagagaaag agagtcagaa ccagaagaca      2520
aataaaaagt atgcaacaaa caaatcaaaa tcaagggca  aaggctgggg ttggctcaat      2580
tggttgctac attcaattt  caactcagtc aacggttgag attcactctg acttccccaa      2640
tctaagccgc ggatgcaaac ggttgaatct aacccacaat ccaatctcgt tacttagggg      2700
cttttccgtc attaactcac ccctgccacc cggtttccct ataaattgga actcaatgct      2760
cccctctaaa ctcgtatcgc ttcagagttg agaccaagac acactcgttc atatatctct      2820
ctgctcttct cttctcttct acctctcaag gtacttttct tctccctcta ccaaatccta      2880
gattccgtgg ttcaatttcg gatcttgcac ttctggtttg ctttgccttg cttttcctc      2940 aactgggtcc atctaggatc catgtgaaac tctactcttt ctttaatatc tgcggaatac      3000
gcgttggact ttcagatcta gtcgaaatca tttcataatt gcctttcttt cttttagctt      3060
atgagaaata aaatcacttt tttttattt  caaataaaac cttgggcctt gtgctgactg      3120 agatgggtt  tggtgattac agaattttag cgaattttgt aattgtactt gtttgtctgt      3180
agttttgttt tgttttcttg tttctcatac attccttagg cttcaatttt attcgagtat      3240
aggtcacaat aggaattcaa actttgagca ggggaattaa tcccttcctt caaatccagt      3300
ttgtttgtat atatgtttaa aaatgaaac  ttttgcttta aattctatta taactttttt      3360
tatggctgaa atttttgcat gtgtctttgc tctctgttgt aaatttactg tttaggtact      3420
aactctaggc ttgttgtgca gtttttgaag tataaccatg ccacacaaca caatggcggc      3480
caccgcttcc agaaccaccc gattctcttc ttcctcttca cccccacct  tccccaaacg      3540 cattactaga tccaccctcc ctctctctca tcaaaccctc accaaaccca accacgctct      3600
caaaatcaaa tgttccatct ccaaaccccc cacggcggcg cccttcacca aggaagcgcc      3660
gaccacggag cccttcgtgt cacggttcgc ctccggcgaa cctcgcaagg gcgcggacat      3720
ccttgtggag gcgctggaga ggcagggcgt gacgacggtt ttcgcgtacc ccggcggtgc      3780
gtcgatggag atccaccagg cgctcacgcg ctccgccgcc atccgcaacg tgctcccgcg      3840
ccacgagcag ggcggcgtct cgccgccgga aggctacgcg cgttcctccg gcctcccgg      3900 cgtctgcatt gccacctccg gccccggcgc caccaacctc gtgagcggcc tcgccgacgc      3960
tttaatggac agcgtcccag tcgtcgccat caccggccag tcgcccgcc  ggatgatcgg      4020 caccgacgcc ttccaagaaa ccccgatcgt ggaggtgagc agatccatca cgaagcacaa      4080
ctacctcatc ctcgacgtcg acgacatccc ccgcgtcgtc gccgaggctt tcttcgtcgc      4140
cacctccggc cgcccggtc  cggtcctcat cgacattccc aaagacgttc agcagcaact      4200
cgccgtgcct aattgggacg agcccgttaa cctccccggt tacctcgcca ggctgccagg      4260 gcccccgcc  gaggcccaat tggaacacat tgtcagactc atcatggagg cccaaaagcc      4320
```

```
cgttctctac gtcggcggtg gcagtttgaa ttccagtgct gaattgaggc gctttgttga    4380
actcactggt attcccgttg ctagcacttt aatgggtctt ggaacttttc ctattggtga    4440
tgaatattcc cttcagatgc tgggtatgca tggtactgtt tatgctaact atgctgttga    4500
caatagtgat ttgttgcttg cctttgsggt aaggtttgat gaccgtgtta ctgggaagct    4560
tgaggctttt gctagtaggg ctaagattgt tcacattgat attgattctg ccagattgg     4620 gaagaacaag caggcgcacg tgtcggtttg cgcggatttg aagttggcct tgaagggaat    4680
taatatgatt ttggaggaga aaggagtgga gggtaagttt gatcttggag ttggagaga    4740 agagattaat gtgcagaaac acaagtttcc attgggttac aagacattcc aggacgcgat    4800
ttctccgcag catgctatcg aggttcttga tgagttgact aatggagatg ctattgttag    4860
tactggggtt gggcagcatc aaatgtgggc tgcgcagttt tacaagtaca agagaccgag    4920
gcagtggttg acctcagggg gtcttggagc catgggtttt ggattgcctg cggctattgg    4980
tgctgctgtt gctaaccctg gggctgttgt ggttgacatt gatggggatg gtagtttcat    5040
catgaatgtt caggagttgg ccactataag agtggagaat ctcccagtta agatattgtt    5100
gttgaacaat cagcatttgg gtatggtggt tcagttggag gataggttct acaagtccaa    5160
tagagctcac acctatcttg agatccgtc tagcgagagc gagatattcc caaacatgct     5220
caagtttgct gatgcttgtg gataccggc agcgcgagtg acgaagaagg aagagcttag    5280
agcggcaatt cagagaatgt tggacacccc tgggcccctac cttcttgatg tcattgtgcc    5340
ccatcaggag catgtgttgc cgatgattcc cagtaatgga tccttcaagg atgtgataac    5400
tgagggtgat ggtagaacga ggtactgatt gcctagacca aatgttcctt gatgcttgtt    5460
ttgtacaata tatataagat aatgctgtcc tagttgcagg atttggcctg tggtgagcat    5520
catagtctgt agtagttttg gtagcaagac attttatttt cctttttatt aacttactac     5580
atgcagtagc atctatctat ctctgtagtc tgatatctcc tgttgtctgt attgtgccgt     5640 tggattttt gctgtagtga gactgaaaat gatgtgctag taataatatt tctgttagaa    5700
atctaagtag agaatctgtt gaagaagtca aagctaatg gaatcaggtt acatatcaat     5760
gttttctttt ttttagcggt tggtagacgt gtagattcaa cttctcttgg agctcaccta    5820
ggcaatcagt aaaatgcata ttccttttt aacttgccat ttatttactt ttagtggaaa      5880
ttgtgaccaa tttgttcatg tagaacggat ttggaccatt gcgtccacaa aacgtctctt    5940
ttgctcgatc ttcacaaagc gataccgaaa tccagagata gttttcaaaa gtcagaaatg    6000
gcaaagttat aaatagtaaa acagaataga tgctgtaatc gacttcaata acaagtggca    6060
tcacgtttct agttctagac ccgggtaccg gcgcgcccga tcatccggat atagttcctc    6120
ctttcagcaa aaaccctc aagacccgtt tagaggcccc aaggggttat gctagttatt      6180
gctcagcggt ggcagcagcc aactcagctt cctttcgggc tttgttagca gccggatcga    6240
tccaagctgt acctcactat tcctttgccc tcggacgagt gctgggcgt cggtttccac      6300 tatcggcgag tacttctaca cagccatcgg tccagacggc cgcgcttctg cgggcgattt    6360
gtgtacgccc gacagtcccg gctccggatc ggacgattgc gtcgcatcga ccctgcgccc    6420
aagctgcatc atcgaaattg ccgtcaacca agctctgata gagttggtca agaccaatgc    6480
ggagcatata cgcccggagc cgcggcgatc ctgcaagctc cggatgcctc cgctcgaagt    6540
agcgcgtctg ctgctccata caagccaacc acggcctcca gaagaagatg ttggcgacct    6600
cgtattggga atccccgaac atcgcctcgc tccagtcaat gaccgctgtt atgcggccat    6660
```

```
tgtccgtcag acattgttg gagccgaaat ccgcgtgcac gaggtgccgg acttcggggc    6720
agtcctcggc ccaaagcatc agctcatcga gagcctgcgc gacggacgca ctgacggtgt    6780
cgtccatcac agtttgccag tgatacacat ggggatcagc aatcgcgcat atgaaatcac    6840
gccatgtagt gtattgaccg attccttgcg gtccgaatgg gccgaacccg ctcgtctggc    6900
taagatcggc cgcagcgatc gcatccatag cctccgcgac cggctgcaga acagcgggca    6960
gttcggtttc aggcaggtct tgcaacgtga caccctgtgc acggcgggag atgcaatagg    7020
tcaggctctc gctgaattcc ccaatgtcaa gcacttccgg aatcgggagc gcggccgatg    7080
caaagtgccg ataaacataa cgatctttgt agaaaccatc ggcgcagcta tttacccgca    7140
ggacatatcc acgccctcct acatcgaagc tgaaagcacg agattcttcg ccctccgaga    7200
gctgcatcag gtcggagacg ctgtcgaact tttcgatcag aaacttctcg acagacgtcg    7260
cggtgagttc aggcttttcc atgggtatat ctccttctta agttaaaca aaattatttc    7320
tagagggaaa ccgttgtggt ctccctatag tgagtcgtat taatttcgcg ggatcgagat    7380
ctgatcaacc tgcattaatg aatcggccaa cgcgcgggga gaggcggttt gcgtattggg    7440
cgctcttccg cttcctcgct cactgactcg ctgcgctcgg tcgttcggct gcggcgagcg    7500
gtatcagctc actcaaaggc ggtaatacgg ttatccacag aatcagggga taacgcagga    7560
aagaacatgt gagcaaaagg ccagcaaaag gccaggaacc gtaaaaaggc cgcgttgctg    7620
gcgttttttcc ataggctccg cccccctgac gagcatcaca aaaatcgacg ctcaagtcag    7680
aggtggcgaa acccgacagg actataaaga taccaggcgt ttccccctgg aagctccctc    7740
gtgcgctctc ctgttccgac cctgccgctt accggatacc tgtccgcctt tctcccttcg    7800
ggaagcgtgg cgctttctca atgctcacgc tgtaggtatc tcagttcggt gtaggtcgtt    7860
cgctccaagc tgggctgtgt gcacgaaccc cccgttcagc ccgaccgctg cgccttatcc    7920
ggtaactatc gtcttgagtc aacccggta agacacgact tatcgccact ggcagcagcc    7980
actggtaaca ggattagcag agcgaggtat gtaggcggtg ctacagagtt cttgaagtgg    8040
tggcctaact acggctacac tagaaggaca gtatttggta tctgcgctct gctgaagcca    8100
gttaccttcg gaaaaagagt tggtagctct tgatccggca acaaaccac cgctggtagc    8160
ggtggttttt tgtttgcaa gcagcagatt acgcgcagaa aaaaggatc tcaagaagat    8220
cctttgatct tttctacggg gtctgacgct cagtggaacg aaaactcacg ttaagggatt    8280
ttggtcatga cattaaccta aaaaatagg cgtatcacga ggccctttcg tctcgcgcgt    8340
ttcggtgatg acggtgaaaa cctctgacac atgcagctcc cggagacggt cacagcttgt    8400
ctgtaagcgg atgccgggag cagacaagcc cgtcagggcg cgtcagcggg tgttggcggg    8460
tgtcggggct ggcttaacta tgcggcatca gagcagattg tactgagagt gcaccatatg    8520
gacatattgt cgttagaacg cggctacaat taatacataa ccttatgtat catacacata    8580
cgatttaggt gacactatag aacgcgcgcg gttaccgggg ccccccctcg aggtcgacgg    8640
tatcgataag cttgatatcg aattcctgca gcccggggga tccactagtt ctagagcggc    8700
ccgcgccgtc gacggatata atgagccgta acaaagatg attaagtagt aattaatacg    8760
tactagtaaa agtggcaaaa gataacgaga agaaccaat ttctttgcat tcggccttag    8820
cggaaggcat atataagctt tgattatttt atttagtgta atgatttcgt acaaccaaag    8880
cattttattta gtactctcac acttgtgtcg cggccgcgaa ttttttgcgg acattgtagt    8940
tgaacatgaa tatgttgagt gcactggatc tgcaatccaa gctttagttt tgttcaagaa    9000
gctatatcca ggacatagga agaaagagat agaaaatttc attaccaatg cagttcgatt    9060
```

```
ccttgaagat acacaaacag ctgatggttc atggtatgga aattggggag tttgcttcac      9120
ttatggctct tggtttgcac ttggaggtct agcagctgct ggtaagactt acaccaattg      9180
tgctgccatt cgcaaagccg ttaaatttct acttacaaca caaagagagg acggtggatg      9240
gggagagagt tatctttcaa gcccaaaaaa gatatatgta cctctagaag gaagccgatc      9300
aaatgttgta catacagcat gggctcttat gggactaatt catgctggac aggcggatag      9360 agacccatg cctcttcacc gtgctgcaaa gttgctcatt aattctcagt ggaagaggg       9420 tgattggccc caacaggaaa tcacgggagt attcatgaaa aattgcatgt tgcattatcc      9480
aatgtacaga gatatttatc caatgtgggc tctagctgaa tatcgaaggc gggttccatt      9540
gccttccact gaagtttaag aaaaagtcct acatacccct gcagaattcg ccctttaaga      9600
aaaagtccta catacccaaa attgagaatt aattagtttc cacttgagta aatatacgtt      9660
aacatacatg cataaaagca acttctgtat ctcttttaa aaaacacca catatcttta       9720 caccgtgagt gcgtaacata ttttctcata tagtatacta tttaatgcca atacatatga     9780
tgaatgaaag aaagtaataa agtaggagag aagaaggaaa cttacgacat taaacttcag     9840
tggaaggcaa tggaacccgc cttcgatatt cagctagagc ccacattgga taaatatctc     9900
tgtacattgg ataatgcaac atgcaatttt tcatgaatac tcccgtgatt tcctgttggg     9960
gccaatcacc ctcttccaac tgagaattaa tgagcaactt gcagcacgg tgaagaggca     10020 tggggtctct atccgcctgt ccagcatgaa ttagtcccat aagagcccat gctgtatgta    10080
caacatttga tcggcttcct tctagaggta catatatctt ttttgggctt gaaagataac    10140
tctctcccca tccaccgtcc tctctttgtg ttgtaagtag aaatttaacg gctttgcgaa    10200
tggcagcaca attggtgtaa gtcttaccag cagctgctag acctccaagt gcaaaccaag    10260
agccataagt gaagcaaact ccccaatttc cataccatga accatcagct gtttgtgtat   10320
cttcaaggaa tcgaactgca ttggtaatga aattttctat ctctttcttc ctatgtcctg    10380
gatatagctt cttgaacaaa actaaagctt ggattgcaga tccagtgcac tcaacatatt    10440
catgttcaac tacaatgtcc gcaaaaaatt cgc                                 10473

<210> SEQ ID NO 31
<211> LENGTH: 8695
<212> TYPE: DNA
<213> ORGANISM: Artificial
<220> FEATURE:
<223> OTHER INFORMATION: recombinant AscI DNA fragment from PHP20767
<220> FEATURE:
<221> NAME/KEY: misc_feature
<222> LOCATION: (3520)..(3520)
<223> OTHER INFORMATION: n is a, c, g, or t

<400> SEQUENCE: 31
cgcgccggta ccgggccccc cctcgaggtc gacggtatcg ataagcttga tatcgaattc       60
ctgcagcccg ggggatccac tagttctaga gcggccgcg ccgtcgacgg atataatgag      120
ccgtaaacaa agatgattaa gtagtaatta atacgtacta gtaaaagtgg caaaagataa     180
cgagaaagaa ccaatttctt tgcattcggc cttagcggaa ggcatatata agctttgatt    240 atttattta gtgtaatgat ttcgtacaac caaagcattt atttagtact ctcacacttg     300
tgtcgcggcc gcttaaactt cagtggaagg caatggaacc cgccttcgat attcagctag    360
agcccacatt ggataaatat ctctgtacat tggataatgc aacatgcaat ttttcatgaa    420
tactcccgtg atttcctgtt ggggccaatc accctcttcc aactgagaat taatgagcaa    480
```

```
ctttgcagca cggtgaagag gcatggggtc tctatccgcc tgtccagcat gaattagtcc    540
cataagagcc catgctgtat gtacaacatt tgatcggctt ccttctagag gtacatatat    600
cttttttggg cttgaaagat aactctctcc ccatccaccg tcctctcttt gtgttgtaag    660
tagaaattta acggctttgc gaatggcagc acaattggtg taagtcttac cagcagctgc    720
tagacctcca agtgcaaacc aagagccata agtgaagcaa actccccaat ttccatacca    780
tgaaccatca gctgtttgtg tatcttcaag gaatcgaact gcattggtaa tgaaattttc    840
tatctctttc ttcctatgtc ctggatatag cttcttgaac aaaactaaag cttggattgc    900
agatccagtg cactcaacat attcatgttc aactacaatg tccgcaaaaa attctgtggg    960
attgagtaat tctaaccact cttgagctcc tgcaggctcc catgctgcta aaccaccttt   1020
tttactctga agcgacaaca agacattgac tgaatcgtat aatctttcag gttccatctt   1080
ttctcccaca atctctggtg gcaacattga tagaagtaga caacacttta aaccttctgc   1140
agtgcaatca gaaacttgcc atccatggtc ttgatcagag aatgtccaag acccttaga    1200 aatatgacga tgcatacttt taaaatctcc aaaaggatta tccttcacct gagacttctt   1260
gatgaaatca tgtccttttg caaacgtagg accaatttct tcaattatgt tagtggcaag   1320
caaagcttga acagcaaagc cagcatccca ttcttggcta ccaaaactct gcatggtcat   1380
tccatcttca gaaacccata agtaatctgg gaccccttgca agatgcttct tgaaagcatc   1440
tccgtttgga tcttccaccc aacaagcaag catacataaa acctttttcca cacaaccaat   1500 ggttatgtat cgactagtct catcttcata atgaatatgt ttcatagtta cttgaagggc   1560 ctttttctcta atcaacttgt tgaaaggcca acgagtaagt agcggttcag tgaatatgta   1620
taaactatcc catattaggt cttgtatcaa aggatgggga tagtaaagat cttcctttgc   1680
acattggtga cgcgctttct tccaattaac tttttcataa ggttgagtaa acaactcttc   1740
tcttaattgt aagatgagtg gtgtgattgg acccacaaac ctcttcccat ataagtaaga   1800
cataggcatg tataccaatc gacagtaaca ccacatctta gctggatgca taggaagaaa   1860
agatggaagg atccaaaact ctgggggcat tgggttgctt ccgcaccaat caaatacacc   1920
gagtatcgaa agccaagttt ttccccatga aggtatatgt gttacaccac catgatctcg   1980
aatccacttt cttgctctag cacaagcatt gtcatgacct ccattaggtc cttctccaag   2040
cattcgcatg catatatagt tcagtgcagt acaaaacata gtgctatgac cctctatgtg   2100
tagtccccat cctccgtctt cattctggtg ataatatgtg taacgaagaa tttcttttgcg   2160 atgttcttct ggaaatactg attcaagatt tcctgtaata tacatacaaa aaaccaaggg   2220
aggaagaaag aagagaggac ctgcaatttg agcaggccaa tggccatcag aggtctgcag   2280
tgccgcaagg tggtgtgcgc cccttctgac ggcgcttgtg acttttttggt atgtgatttc   2340 ctctccatct tctatagtca cacgaggaat tgtttgtttg aagttatttt ctctgagaac   2400
ctgaaaacgc caaaggaggt cagcgcaggg cttgaccttg aagcggttgt ggtagaaatg   2460
ctgacgagct gcttcaacct gggcccgttc ctctggactg cctgcttcag gatcaaactc   2520
ccatgtctgc ctcccaacga aattgttgt gctgaatatg tatggatcat ttcctccatc    2580
tgctatcttc agcctccaca tgcggccgct tgggggggcta tggaagactt tcttagttag   2640
ttgtgtgaat aagcaatgtt gggagaatcg ggactactta aggatagga ataaaacaga    2700 aaagtattaa gtgctaatga aatatttaga ctgataatta aaatcttcac gtatgtccac   2760
ttgatataaa aacgtcagga ataaaggaag tacagtagaa tttaaaggta ctcttttttat  2820 atatacccgt gttctctttt tggctagcta gttgcataaa aaataatcta tattttttatc  2880
```

```
attattttaa atatcttatg agatggtaaa tatttatcat aattttttt actattattt    2940
attatttgtg tgtgtaatac atatagaagt taattacaaa ttttatttac tttttcatta   3000
ttttgatatg attcaccatt aatttagtgt tattatttat aatagttcat tttaatcttt   3060
ttgtatatat tatgcgtgca gtactttttt cctacatata actactatta catttatt    3120
ataatatt tttattaatg aattttcgtg ataatatgta atattgttca ttattatttc    3180
agatttttta aaaatatttg tgttattatt tatgaaatat gtaattttt tagtatttga   3240
ttttatgatg ataagtgtt ctaaattcaa agaaggggg aaagcgtaaa cattaaaaaa    3300
cgtcatcaaa caaaaacaaa atcttgttaa taaagataaa actgtttgtt ttgatcactg   3360
ttatttcgta atataaaaac attatttata tttatattgt tgacaaccaa atttgcctat   3420
caaatctaac caatataatg catgcgtggc aggtaatgta ctaccatgaa cttaagtcat   3480
gacataataa accgtgaatc tgaccaatgc atgtacctan ctaaattgta tttgtgacac   3540
gaagcaaatg attcaattca caatggagat gggaaacaaa taatgaagaa cccagaacta   3600
agaaagcttt tctgaaaaat aaaataaagg caatgtcaaa agtatactgc atcatcagtc   3660
cagaaagcac atgatatttt tttatcagta tcaatgcagc tagttttatt ttacaatatc   3720
gatatagcta gtttaaatat attgcagcta gatttataaa tatttgtgtt attatttatc   3780
atttgtgtaa tcctgttttt agtattttag tttatatatg atgataatgt attccaaatt   3840
taaaagaagg gaaataaatt taaacaagaa aaaaagtcat caaacaaaaa acaaatgaaa   3900
gggtggaaag atgttaccat gtaatgtgaa tgttacagta tttcttttat tatagagtta   3960
acaaattaac taatatgatt ttgttaataa tgataaaata tttttttat tattatttca    4020
taatataaaa atagtttact taatataaaa aaaattctat cgttcacaac aaagttggcc   4080
acctaattta accatgcatg tacccatgga ccatattagg taaccatcaa acctgatgaa   4140
gagataaaga gatgaagact taagtcataa cacaaaacca taaaaacaa aaatacaatc    4200
aaccgtcaat ctgaccaatg catgaaaaag ctgcaatagt gagtggcgac acaaagcaca   4260
tgattttctt acaacggaga taaaccaaa aaaatatttc atgaacaacc tagaacaaat    4320
aaagcttta tataataaat atataaataa ataaaggcta tggaataata tacttcaata    4380
tatttggatt aaataaattg ttggcggggt tgatatattt atacacacct aaagtcactt   4440
caatctcatt ttcacttaac ttttattttt tttttctttt tatttatcat aaagagaata   4500
ttgataatat acttttaac atattttat gacattttt attggtgaaa acttattaaa     4560
aatcataaat tttgtaagtt agatttattt aaagagttcc tcttcttatt ttaaatttt    4620
taataaattt ttaaataact aaaatttgtg ttaaaaatgt taaaaaagtg tgttattaac   4680
ccttctcttc gaggatccaa gcttggcgcg gccgccacc gcggtgggt cgactctagt     4740
aagctttgct ctagatcaaa ctcacatcca aacataacat ggatatcttc cttaccaatc   4800
atactaatta ttttgggtta aatattaatc attattttta agatattaat taagaaatta   4860
aaagattttt taaaaaatg tataaaatta tattattcat gattttcat acatttgatt     4920
ttgataataa atatatttt tttaatttct taaaaaatgt tgcaagacac ttattagaca   4980
tagtcttgtt ctgtttacaa aagcattcat catttaatac attaaaaaat atttaatact   5040
aacagtagaa tcttcttgtg agtggtgtgg gagtaggcaa cctggcattg aaacgagaga   5100
aagagagtca gaaccagaag acaaataaaa agtatgcaac aaacaaatca aaatcaaagg   5160
gcaaaggctg gggttggctc aattggttgc tacattcaat tttcaactca gtcaacggtt   5220
```

```
gagattcact ctgacttccc caatctaagc cgcggatgca aacggttgaa tctaacccac   5280
aatccaatct cgttacttag gggcttttcc gtcattaact cacccctgcc acccggtttc   5340
cctataaatt ggaactcaat gctcccctct aaactcgtat cgcttcagag ttgagaccaa   5400
gacacactcg ttcatatatc tctctgctct tctcttctct tctacctctc aaggtacttt   5460
tcttctccct ctaccaaatc ctagattccg tggttcaatt tcggatcttg cacttctggt   5520
ttgctttgcc ttgcttttc ctcaactggg tccatctagg atccatgtga aactctactc   5580
tttctttaat atctgcggaa tacgcgtttg actttcagat ctagtcgaaa tcatttcata   5640
attgcctttc tttcttttag cttatgagaa ataaaatcac ttttttttta tttcaaaata   5700
aaccttgggc cttgtgctga ctgagatggg gtttggtgat tacagaattt tagcgaattt   5760
tgtaattgta cttgtttgtc tgtagttttg ttttgttttc ttgtttctca tacattcctt   5820
aggcttcaat tttattcgag tataggtcac aataggaatt caaactttga gcaggggaat   5880
taatcccttc cttcaaatcc agtttgtttg tatatatgtt taaaaaatga aacttttgct   5940
ttaaattcta ttataacttt tttatggct gaaattttg catgtgtctt tgctctctgt   6000
tgtaaattta ctgtttaggt actaactcta ggcttgttgt gcagttttg aagtataacc   6060 atgccacaca acacaatggc ggccaccgct tccagaacca cccgattctc ttcttcctct   6120
tcacacccca ccttccccaa acgcattact agatccaccc tccctctctc tcatcaaacc   6180
ctcaccaaac ccaaccacgc tctcaaaatc aaatgttcca tctccaaacc ccccacggcg   6240
gcgcccttca ccaaggaagc gccgaccacg gagcccttcg tgtcacggtt cgcctccggc   6300
gaacctcgca agggcgcgga catccttgtg gaggcgctgg agaggcaggg cgtgacgacg   6360
gtgttcgcgt accccggcgg tgcgtcgatg gagatccacc aggcgctcac gcgctccgcc   6420
gccatccgca acgtgctccc gcgccacgag cagggcggcg tcttcgccgc cgaaggctac   6480
gcgcgttcct ccggcctccc cggcgtctgc attgccacct ccggcccggg cgccaccaac   6540
ctcgtgagcg gcctcgccga cgctttaatg gacagcgtcc cagtcgtcgc catcaccggc   6600
caggtcgccc gccggatgat cggcaccgac gccttccaag aaaccccgat cgtgagggtg   6660
agcagatcca tcacgaagca caactacctc atcctcgacg tcgacgacat cccccgcgtc   6720
gtcgccgagg cttttcttcgt cgccacctcc ggccgcccg gtccggtcct catcgacatt   6780
cccaaagacg ttcagcagca actcgccgtg cctaattggg acgagcccgt taacctcccc   6840
ggttacctcg ccaggctgcc caggcccccc gccgaggccc aattggaaca cattgtcaga   6900
ctcatcatgg aggcccaaaa gcccgttctc tacgtcggcg gtggcagttt gaattccagt   6960
gctgaattga ggcgctttgt tgaactcact ggtattcccg ttgctagcac tttaatgggt   7020
cttggaactt ttcctattgg tgatgaatat tcccttcaga tgctgggtat gcatggtact   7080
gtttatgcta actatgctgt tgacaatagt gatttgttgc ttgcctttgg ggtaaggttt   7140
gatgaccgtg ttactgggaa gcttgaggct tttgctagta gggctaagat tgttcacatt   7200
gatattgatt ctgccgagat tgggaagaac aagcaggcgc acgtgtcggt ttgcgcggat   7260
ttgaagttgg ccttgaaggg aattaatatg atttttggagg agaaaggagt ggagggtaag   7320
tttgatcttg gaggttggag agaagagatt aatgtgcaga acacaagtt tccattgggt   7380 tacaagacat tccaggacgc gatttctccg cagcatgcta tcgaggttct tgatgagttg   7440
actaatggag atgctattgt tagtactggg gttgggcagc atcaaatgtg ggctgcgcag   7500
ttttacaagt acaagagacc gaggcagtgg ttgacctcag ggggtcttgg agccatgggt   7560
tttggattgc ctgcggctat tggtgctgct gttgctaacc ctggggctgt tgtggttgac   7620
```

```
attgatgggg atggtagttt catcatgaat gttcaggagt tggccactat aagagtggag    7680
aatctcccag ttaagatatt gttgttgaac aatcagcatt tgggtatggt ggttcagttg    7740
gaggataggt tctacaagtc caatagagct cacacctatc ttggagatcc gtctagcgag    7800
agcgagatat tcccaaacat gctcaagttt gctgatgctt gtgggatacc ggcagcgcga    7860
gtgacgaaga aggaagagct tagagcggca attcagagaa tgttggacac ccctggcccc    7920
taccttcttg atgtcattgt gccccatcag gagcatgtgt tgccgatgat tcccagtaat    7980
ggatccttca aggatgtgat aactgagggt gatggtagaa cgaggtactg attgcctaga    8040
ccaaatgttc cttgatgctt gttttgtaca atatatataa gataatgctg tcctagttgc    8100
aggatttggc ctgtggtgag catcatagtc tgtagtagtt ttggtagcaa gacattttat    8160 tttccttttta tttaacttac tacatgcagt agcatctatc tatctctgta gtctgatatc    8220
tcctgttgtc tgtattgtgc cgttggattt tttgctgtag tgagactgaa aatgatgtgc    8280
tagtaataat atttctgtta gaaatctaag tagagaatct gttgaagaag tcaaaagcta    8340
atggaatcag gttacatatt caatgttttt cttttttttag cggttggtag acgtgtagat    8400
tcaacttctc ttggagctca cctaggcaat cagtaaaatg catattcctt ttttaacttg    8460
ccatttattt acttttagtg gaaattgtga ccaatttgtt catgtagaac ggatttggac    8520
cattgcgtcc acaaaacgtc tcttttgctc gatcttcaca aagcgatacc gaaatccaga    8580 gatagtttc aaaagtcaga aatggcaaag ttataaatag taaaacagaa tagatgctgt    8640
aatcgacttc aataacaagt ggcatcacgt ttctagttct agacccgggt accgg         8695
```

<210> SEQ ID NO 32
<211> LENGTH: 7960
<212> TYPE: DNA
<213> ORGANISM: Artificial
<220> FEATURE:
<223> OTHER INFORMATION: recombinant AscI DNA fragment from PHP21157
<220> FEATURE:
<221> NAME/KEY: misc_feature
<222> LOCATION: (2785)..(2785)
<223> OTHER INFORMATION: n is a, c, g, or t

<400> SEQUENCE: 32

```
cgcgccggta ccgggccccc cctcgaggtc gacggtatcg ataagcttga tatcgaattc     60
ctgcagcccg gggatccac tagttctaga gcggccgcg ccgtcgacgg atataatgag      120
ccgtaaacaa agatgattaa gtagtaatta atacgtacta gtaaaagtgg caaaagataa    180
cgagaaagaa ccaatttctt tgcattcggc cttagcggaa ggcatatata agctttgatt   240
attttattta gtgtaatgat ttcgtacaac caaagcattt atttagtact ctcacacttg    300
tgtcgcggcc gcgaatttt tgcggacatt gtagttgaac atgaatatgt tgagtgcact    360
ggatctgcaa tccaagcttt agttttgttc aagaagctat atccaggaca taggaagaaa    420
gagatagaaa atttcattac caatgcagtt cgattccttg aagatacaca aacagctgat    480
ggttcatggt atgaaattg gggagtttgc ttcacttatg gctcttggtt tgcacttgga    540
ggtctagcag ctgctggtaa gacttacacc aattgtgctg ccattcgcaa agccgttaaa    600
tttctactta caacacaaag agaggacggt ggatggggag agagttatct ttcaagccca    660
aaaaagatat atgtacctct agaaggaagc cgatcaaatg ttgtacatac agcatgggct    720
cttatgggac taattcatgc tggacaggcg gatagagacc ccatgcctct tcaccgtgct    780
gcaaagttgc tcattaattc tcagttggaa gagggtgatt ggccccaaca ggaaatcacg    840
```

```
ggagtattca tgaaaaattg catgttgcat tatccaatgt acagagatat ttatccaatg      900
tgggctctag ctgaatatcg aaggcgggtt ccattgcctt ccactgaagt ttaagaaaaa      960
gtcctacata cccctgcaga attcgcccctt taagaaaaag tcctacatac ccaaaattga    1020
gaattaatta gtttccactt gagtaaatat acgttaacat acatgcataa aagcaacttc    1080
tgtatctctt tttaaaaaaa caccacatat ctttacaccg tgagtgcgta acatattttc    1140
tcatatagta tactatttaa tgccaataca tatgatgaat gaaagaaagt aataaagtag    1200
gagagaagaa ggaaacttac gacattaaac ttcagtggaa ggcaatggaa cccgccttcg    1260
atattcagct agagcccaca ttggataaat atctctgtac attggataat gcaacatgca    1320
atttttcatg aatactcccg tgatttcctg ttggggccaa tcaccctctt ccaactgaga    1380
attaatgagc aactttgcag cacggtgaag aggcatgggg tctctatccg cctgtccagc    1440
atgaattagt cccataagag cccatgctgt atgtacaaca tttgatcggc ttccttctag    1500
aggtacatat atctttttg ggcttgaaag ataactctct ccccatccac cgtcctctct    1560
ttgtgttgta agtagaaatt taacggcttt gcgaatggca gcacaattgg tgtaagtctt    1620
accagcagct gctagacctc caagtgcaaa ccaagagcca taagtgaagc aaactcccca    1680
atttccatac catgaaccat cagctgtttg tgtatcttca aggaatcgaa ctgcattggt    1740
aatgaaattt tctatctctt tcttcctatg tcctggatat agcttcttga acaaaactaa    1800
agcttggatt gcagatccag tgcactcaac atattcatgt tcaactacaa tgtccgcaaa    1860
aaattcgcgg ccgcttgggg ggctatgaa gactttctta gttagttgtg tgaataagca    1920
atgttgggag aatcgggact acttatagga taggaataaa acagaaaagt attaagtgct    1980
aatgaaatat ttagactgat aattaaaatc ttcacgtatg tccacttgat ataaaaacgt    2040
caggaataaa ggaagtacag tagaatttaa aggtactctt tttatatata cccgtgttct    2100
cttttttggct agctagttgc ataaaaaata atctatattt ttatcattat tttaaatatc    2160
ttatgagatg gtaaatattt atcataattt ttttactat tatttattat ttgtgtgtgt    2220
aatacatata gaagttaatt acaaatttta tttacttttt cattattttg atatgattca    2280
ccattaattt agtgttatta tttataatag ttcatttaa tcttttttgta tatattatgc    2340
gtgcagtact ttttttcctac atataactac tattacattt tattttatata atattttat    2400
taatgaattt tcgtgataat atgtaatatt gttcattatt atttcagatt ttttaaaaat    2460
atttgtgtta ttatttatga aatatgtaat tttttttagta tttgattta tgatgataaa    2520
gtgttctaaa ttcaaaagaa gggggaaagc gtaaacatta aaaaacgtca tcaaacaaaa    2580
acaaaatctt gttaataaag ataaaactgt ttgttttgat cactgttatt tcgtaatata    2640
aaaacattat ttatatttat attgttgaca accaaaatttg cctatcaaat ctaaccaata    2700
taatgcatgc gtggcaggta atgtactacc atgaacttaa gtcatgacat aataaaccgt    2760
gaatctgacc aatgcatgta cctanctaaa ttgtatttgt gacacgaagc aaatgattca    2820
attcacaatg gagatgggaa acaaataatg aagaacccag aactaagaaa gcttttctga    2880
aaaataaaat aaaggcaatg tcaaaagtat actgcatcat cagtccagaa agcacatgat    2940
atttttttat cagtatcaat gcagctagtt ttattttaca atatcgatat agctagttta    3000
aatatattgc agctagattt ataaatattt gtgttattat ttatcatttg tgtaatcctg    3060
tttttagtat tttagtttat atatgatgat aatgtattcc aaatttaaaa gaagggaaat    3120
aaatttaaac aagaaaaaaa gtcatcaaac aaaaaacaaa tgaaagggtg gaaagatgtt    3180
accatgtaat gtgaatgtta cagtatttct tttattatag agttaacaaa ttaactaata    3240
```

```
tgattttgtt aataatgata aaatatttt tttattatta tttcataata taaaaatagt    3300
ttacttaata taaaaaaaat tctatcgttc acaacaaagt tggccaccta atttaaccat    3360
gcatgtaccc atggaccata ttaggtaacc atcaaacctg atgaagagat aaagagatga    3420
agacttaagt cataacacaa aaccataaaa aacaaaaata caatcaaccg tcaatctgac    3480
caatgcatga aaaagctgca atagtgagtg gcgacacaaa gcacatgatt ttcttacaac    3540
ggagataaaa ccaaaaaaat atttcatgaa caacctagaa caaataaagc ttttatataa    3600
taaatatata aataaataaa ggctatggaa taatatactt caatatattt ggattaaata    3660
aattgttggc ggggttgata tatttataca cacctaaagt cacttcaatc tcattttcac    3720
ttaactttta tttttttttt ctttttattt atcataaaga gaatattgat aatatacttt    3780
ttaacatatt tttatgacat tttttattgg tgaaaactta ttaaaaatca taaattttgt    3840
aagttagatt tatttaaaga gttcctcttc ttattttaaa tttttaata aattttttaaa    3900
taactaaaat ttgtgttaaa aatgttaaaa aagtgtgtta ttaacccttc tcttcgagga    3960
tccaagcttg gcgcgggccg ccaccgcggt ggggtcgact ctagtaagct tgctctaga    4020
tcaaactcac atccaaacat aacatggata tcttccttac caatcatact aattattttg    4080
ggttaaatat taatcattat ttttaagata ttaattaaga aattaaaaga tttttttaaaa   4140
aaatgtataa aattatatta ttcatgattt ttcatacatt tgattttgat aataaatata    4200
ttttttttaa tttcttaaaa aatgttgcaa gacacttatt agacatagtc ttgttctgtt    4260
tacaaaagca ttcatcattt aatacattaa aaaatattta atactaacag tagaatcttc    4320
ttgtgagtgg tgtgggagta ggcaacctgg cattgaaacg agagaaagag agtcagaacc    4380
agaagacaaa taaaaagtat gcaacaaaca aatcaaaatc aaagggcaaa ggctggggtt    4440
ggctcaattg gttgctacat tcaattttca actcagtcaa cggttgagat tcactctgac    4500
ttccccaatc taagccgcgg atgcaaacgg ttgaatctaa cccacaatcc aatctcgtta    4560
cttaggggct tttccgtcat taactcaccc ctgccacccg gtttccctat aaattggaac    4620
tcaatgctcc cctctaaact cgtatcgctt cagagttgag accaagacac actcgttcat    4680
atatctctct gctcttctct tctcttctac ctctcaaggt acttttcttc tccctctacc    4740
aaatcctaga ttccgtggtt caatttcgga tcttgcactt ctggtttgct ttgccttgct    4800
ttttcctcaa ctgggtccat ctaggatcca tgtgaaactc tactcttct ttaatatctg     4860
cggaatacgc gtttgacttt cagatctagt cgaaatcatt tcataattgc ctttcttct     4920
tttagcttat gagaaataaa atcactttt tttattca aaataaaacct tgggccttgt     4980
gctgactgag atggggtttg gtgattacag aattttagcg aattttgtaa ttgtacttgt    5040
ttgtctgtag ttttgttttg ttttcttgtt tctcatacat tccttaggct tcaattttat    5100
tcgagtatag gtcacaatag gaattcaaac tttgagcagg ggaattaatc ccttccttca    5160
aatccagttt gtttgtatat atgtttaaaa aatgaaactt tgctttaaa ttctattata     5220
acttttttta tggctgaaat ttttgcatgt gtctttgctc tctgttgtaa atttactgtt    5280
taggtactaa ctctaggctt gttgtgcagt ttttgaagta taaccatgcc acacaacaca    5340
atggcggcca ccgcttccag aaccacccga ttctcttctt cctcttcaca ccccacctc    5400
cccaaacgca ttactagatc caccctccct ctctctcatc aaaccctcac caaacccaac    5460
cacgctctca aaatcaaatg ttccatctcc aaacccccca cggcggcgcc cttcaccaag    5520
gaagcgccga ccacggagcc cttcgtgtca cggttcgcct ccggcgaacc tcgcaagggc    5580
```

```
gcggacatcc ttgtggaggc gctggagagg cagggcgtga cgacggtgtt cgcgtacccc   5640
ggcggtgcgt cgatggagat ccaccaggcg ctcacgcgct ccgccgccat ccgcaacgtg   5700
ctcccgcgcc acgagcaggg cggcgtcttc gccgccgaag gctacgcgcg ttcctccggc   5760
ctccccggcg tctgcattgc cacctccggc cccgcgccca ccaacctcgt gagcggcctc   5820
gccgacgctt taatggacag cgtcccagtc gtcgccatca ccggccaggt cgcccgccgg   5880
atgatcggca ccgacgcctt ccaagaaacc ccgatcgtgg aggtgagcag atccatcacg   5940
aagcacaact acctcatcct cgacgtcgac gacatccccc gcgtcgtcgc cgaggctttc   6000
ttcgtcgcca cctccggccg ccccggtccg gtcctcatcg acattcccaa agacgttcag   6060
cagcaactcg ccgtgcctaa ttgggacgag cccgttaacc tccccggtta cctcgccagg   6120
ctgcccaggc ccccgccgga gcccaattg gaacacattg tcagactcat catggaggcc   6180
caaaagcccg ttctctacgt cggcggtggc agtttgaatt ccagtgctga attgaggcgc   6240
tttgttgaac tcactggtat tcccgttgct agcactttaa tgggtcttgg aacttttcct   6300
attggtgatg aatattccct tcagatgctg ggtatgcatg gtactgttta tgctaactat   6360
gctgttgaca atagtgattt gttgcttgcc tttggggtaa ggtttgatga ccgtgttact   6420
gggaagcttg aggcttttgc tagtagggct aagattgttc acattgatat tgattctgcc   6480
gagattggga agaacaagca ggcgcacgtg tcggtttgcg cggatttgaa gttggccttg   6540
aagggaatta atatgatttt ggaggagaaa ggagtggagg gtaagtttga tcttggaggt   6600
tggagagaag agattaatgt gcagaaacac aagtttccat tgggttacaa gacattccag   6660
gacgcgattt ctccgcagca tgctatcgag gttcttgatg agttgactaa tggagatgct   6720
attgttagta ctggggttgg gcagcatcaa atgtgggctg cgcagtttta caagtacaag   6780
agaccgaggc agtggttgac ctcagggggt cttggagcca tgggttttgg attgcctgcg   6840
gctattggtg ctgctgttgc taaccctggg gctgttgtgg ttgacattga tggggatggt   6900
agtttcatca tgaatgttca ggagttggcc actataagag tggagaatct cccagttaag   6960
atattgttgt tgaacaatca gcatttgggt atggtggttc agttggagga taggttctac   7020
aagtccaata gagctcacac ctatcttgga gatccgtcta gcgagagcga gatattccca   7080
aacatgctca gtttgctga tgcttgtggg ataccggcag cgcgagtgac gaagaaggaa   7140
gagcttagag cggcaattca gagaatgttg gacacccctg gcccctacct tcttgatgtc   7200
attgtgcccc atcaggagca tgtgttgccg atgattccca gtaatggatc cttcaaggat   7260
gtgataactg agggtgatgg tagaacgagg tactgattgc ctagaccaaa tgttccttga   7320
tgcttgtttt gtacaatata tataagataa tgctgtccta gttgcaggat ttggcctgtg   7380
gtgagcatca tagtctgtag tagttttggt agcaagacat tttatttcc ttttatttaa   7440 cttactacat gcagtagcat ctatctatct ctgtagtctg atatctcctg ttgtctgtat   7500
tgtgccgttg gatttttgc tgtagtgaga ctgaaaatga tgtgctagta ataatatttc   7560
tgttagaaat ctaagtagag aatctgttga agaagtcaaa agctaatgga atcaggttac   7620
atattcaatg ttttctttt tttagcggtt ggtagacgtg tagattcaac ttctcttgga   7680
gctcacctag gcaatcagta aaatgcatat tcctttttta acttgccatt tatttacttt   7740
tagtggaaat tgtgaccaat tgttcatgt agaacggatt tggaccattg cgtccacaaa   7800
acgtctcttt tgctcgatct tcacaaagcg ataccgaaat ccagagatag ttttcaaaag   7860
```

```
tcagaaatgg caaagttata aatagtaaaa cagaatagat gctgtaatcg acttcaataa    7920
caagtggcat cacgtttcta gttctagacc cgggtaccgg                          7960
```

COMPOSITIONS WITH INCREASED PHYTOSTEROL LEVELS OBTAINED FROM PLANTS WITH DECREASED TRITERPENE SAPONIN LEVELS

FIELD OF THE INVENTION

This application claims the benefit of U.S. Provisional Application No. 60/734,682 filed Nov. 7, 2005, now expired, and U.S. Provisional Application No. 60/760,515, filed Jan. 19, 2006, now expired. The entire contents of each of these applications is incorporated herein by reference.

This invention is in the field of plant molecular biology. More specifically, the invention includes compositions having increased levels of phytosterols and methods of obtaining such compositions. The compositions may be obtained from plants or plant parts having decreased levels of triterpene saponins. The plants may have decreased activity of at least one oxidosqualene cyclase that catalyzes the cyclization of 2,3-oxidosqualene to form cyclyzed triterpene. The plants or plant parts may be transformed with at least one recombinant DNA molecule comprising a promoter operably linked to at least a portion of a polynucleotide from at least one oxidosqualene cyclase gene. The invention includes any progeny of said plant, wherein said progeny comprise said recombinant DNA molecule. Compositions such as food and feed products, including oils, obtained from plants and/or seeds having an increased level of one or more phytosterols are also part of the invention.

BACKGROUND OF THE INVENTION

Elevated blood cholesterol is a major risk factor for heart disease, which is responsible for ⅓ of all deaths worldwide. Phytosterols have been found effective in lowering elevated cholesterol when incorporated into a variety of low fat foods, demonstrating an 18 to 15% reduction in LDL cholesterol with no reported adverse health effects. Phytosterols have been shown to inhibit uptake from the intestine of dietary and endogenously-produced cholesterol (see, for example, Moreau, et al. (2002) Prog. Lipid Res. 41:457-500).

Naturally occurring phytosterols include, and are not limited to, isofucosterol, sitosterol, stigmasterol, campesterol, cholesterol, cycloartenol, and dihydrobrassicasterol. The most abundant sterols commonly are campesterol, sitosterol, and stigmasterol. Phytosterols commonly occur as free alcohols, or as fatty acid esters, steryl glycosides, or acylated steryl glycosides which are commonly referred to as phytosterol conjugates. Phytostanols are fully-saturated phytosterols (contain no double bonds) and, as such, are considered a subgroup of phytosterols. Phytostanols occur in trace levels in many plant species. Phytosterols can be converted to phytostanols by chemical hydrogenation.

Products and compositions comprising phytosterols are available in the United States for the purpose of increasing heart health. There is a demand for phytosterol formulations that could be included in beverages, dairy drinks, and non-fat foods. Thus, plants having altered phytosterol compositions may be useful in the preparation of the above-mentioned compositions and the compositions will have a different distribution of phytosterols.

Phytosterols, including phytostanols, and triterpenes are biosynthesized via the isoprenoid pathway. In this pathway, two molecules of farnesyl pyrophosphate are joined head-to-head to form squalene, a triterpene. Squalene is then converted to 2,3-oxidosqualene. Various oxidosqualene cyclases catalyze the cyclization of 2,3-oxidosqualene to form various polycyclic skeletons including, but not limited to cycloartenol, lanosterol, lupeol, isomultiflorenol, β-amyrin, α-amyrin, and thalianol. This cyclization event catalyzed by oxidosqualene cyclases forms a branch point between the sterol and triterpene saponin biosynthetic pathways. The various oxidosqualene cyclases are evolutionarily related (Kushiro, T., et al. (1998) Eur. J. Biochem. 256:238-244) and produce a wide variety of three-, four-, and five-ring structures that can be further modified.

For sterol synthesis, the cyclization of 2,3-oxidosqualene is catalyzed by the 2,3-oxidosqualene cyclases, cycloartenol synthase and lanosterol synthase. Cycloartenol (in photosynthetic organisms) and lanosterol (in non-photosynthetic organisms) are 30 carbon, 4-ring structures that can be further modified to form sterols. In photosynthetic organisms, sterols have a wide range of functions including regulation of membrane fluidity and as precursors for the brassinosteroids. In some plants, sterols can also be glycosylated to form steroidal saponins. Cycloatenol serves as a precursor for the production of numerous other sterols. In most plants, cycloartenol is converted to 24-methylene cycloartenol, cycloeucalenol, obtusifoliol, isofucosterol, sitostero, stigmasterol, campesterol, and cholesterol. Cycloartenol is formed by the enzyme cycloartenol synthase (EC 5.4.99.8), also called 2,3-epoxysqualene-cycloartenol cyclase. The basic nucleus of cycloartenol can be further modified by reactions such as desaturation or demethylation to form the common sterol backbones.

For triterpene saponin synthesis, the cyclization of 2,3-oxidosqualene is catalyzed by 2,3-oxidosqualene cyclases, such as lupeol synthase, β-amyrin synthase, α-amyrin synthase, isomultiflorenol synthase, thalianol synthase and dammarenediol synthase. Lupeol, β-amyrin, α-amyrin, isomultiflorenol and thalianol, can be further modified (e.g., oxidation, substitution, and glycosylation) to form triterpene saponins. For example, the basic β-amyrin ring structure may be modified by glycosylation (sometimes preceded by hydroxylation) to form triterpene saponins. The function of triterpene saponins is unclear although it is thought that they play a defense role against pathogens in plant tissues.

SUMMARY OF THE INVENTION

The present invention relates to compositions having increased phytosterol content and methods of obtaining thereof. The compositions may be obtained from transgenic plants and/or plant parts having reduced levels of triterpene saponins. The plants or plant parts may be transformed with at least one recombinant DNA molecule comprising a promoter operably linked to at least a portion of a polynucleotide from at least one oxidosqualene cyclase gene, sufficient to decrease the activity of an oxidosqualene cyclase and increase the production of phytosterols. It is preferred that the composition of the invention contain at least 1.5 times as much phytosterol by weight as a composition prepared from a plant or plant part not expressing the recombinant DNA molecule.

In a preferred embodiment, the oxidosqualene cyclase catalyzes the cyclization of 2,3-oxidosqualene to form at least one triterpene selected from the group consisting of β-amyrin, lupeol, α-amyrin, isomultiflorenol, thalianol, and any combination thereof. In a more preferred embodiment, the oxidosqualene cyclase is selected from the group consisting of lupeol synthase, β-amyrin synthase, α-amyrin synthase, isomultiflorenol synthase, thalianol synthase and dammarenediol synthase. In an even more preferred embodiment, the oxidosqualene cyclase is a β-amyrin synthase. In an even more preferred embodiment, the β amyrin synthase has the amino acid sequence encoded by SEQ ID NO:2. The recombinant DNA molecule may comprise the nucleotide sequence of SEQ ID NO:32.

Methods of producing a composition containing increased levels of phytosterols are encompassed by the invention. In one embodiment, the method of the invention comprises processing a transgenic plant or portion thereof having an increased level of phytosterols as compared to a plant not comprising the recombinant DNA molecule when such a plant or portion thereof has a reduced level of one or more triterpene saponins as compared to a plant not comprising the recombinant DNA molecule.

The processed transgenic plant may have a decreased level of at least one triterpene saponin due to the presence of a recombinant DNA molecule comprising at least a portion of at least one gene that encodes an oxidosqualene cyclase that catalyzes the cyclization of 2,3-oxidosqualene to form cyclyzed triterpene including, but not limited to, lupeol synthase, β-amyrin synthase, α-amyrin synthase, isomultiflorenol synthase, thalianol synthase and dammarenediol synthase. In a specific embodiment the oxidosqualene cyclase is β-amyrin synthase. In another specific embodiment, the transgenic plant is a soybean. In another embodiment the portion of the plant may be a seed, particularly a soybean seed. In an embodiment of the invention, a composition containing increased level of phytosterols may be made by obtained from a transformed soybean seed comprising at least a portion of SEQ ID. NO:2. In an embodiment the recombinant DNA molecule may comprise SEQ ID NO:2. In another embodiment the recombinant DNA molecule may comprise a portion of SEQ ID NO:2 and a portion of SEQ ID NO:1. In a further embodiment the recombinant DNA molecule may comprise a portion of SEQ ID NO:2 separated by an intron from the complement of a portion of SEQ ID NO:2. In an alternative embodiment the intron in the recombinant DNA molecule is the isoflavone synthase (IFS) intron. The composition described herein contains at least 1.5 times as much phytosterol by weight as a composition prepared from a plant or plant part not containing the recombinant DNA molecule. An embodiment of the invention is an extract containing increased level of phytosterols prepared from a plant or plant part comprising a recombinant DNA molecule comprising at least a portion of SEQ ID NO:2. It is preferred that the extract of the invention contain at least 1.5 times as much phytosterol by weight as a composition prepared from a plant or plant part not comprising a recombinant DNA molecule of the invention.

In another embodiment, the invention encompasses a method of producing a phytosterol-containing extract, wherein the extract contains an increased level of one or more phytosterols. The extract may contain a reduced level of one or more triterpene saponins. Such methods comprise processing a transgenic plant or portion thereof having an increased level of one or more phytosterols to produce an oil and extracting the phytosterol-containing extract from the resulting oil. The plant or portion thereof may have a reduced level of one or more triterpene saponins as compared to a plant not comprising the recombinant DNA molecule. In a specific embodiment, the processed transgenic plant has decreased level of at least one triterpene saponin due to the presence of a recombinant DNA molecule comprising at least a portion of at least one gene that encodes an oxidosqualene cyclase that catalyzes the cyclization of 2,3-oxidosqualene to form cyclyzed triterpene including, but not limited to, lupeol synthase, β-amyrin synthase, α-amyrin synthase, isomultiflorenol synthase, thalianol synthase and dammarenediol synthase. In a specific embodiment the oxidosqualene cyclase is β-amyrin synthase. In another specific embodiment, the transgenic plant is a soybean.

Transgenic plant or portions thereof are also encompassed by the invention. In an embodiment, the transgenic plants have decreased levels of triterpene saponins due to the presence of a recombinant DNA molecule comprising at least a portion of at least one gene that encodes an oxidosqualene cyclase that catalyzes the cyclization of 2,3-oxidosqualene to form cyclyzed triterpene including, but not limited to, lupeol synthase, β-amyrin synthase, α-amyrin synthase, isomultiflorenol synthase, thalianol synthase and dammarenediol synthase. In a specific embodiment the oxidosqualene cyclase is β-amyrin synthase. In another specific embodiment, the transgenic plant is a soybean. In an embodiment of the invention, the transgenic plant comprises a recombinant DNA comprising SEQ ID NO:2. In another embodiment the transgenic plant comprises a recombinant DNA comprising a portion of SEQ ID NO:2 and a portion of SEQ ID NO:1. In a further embodiment the plant comprises a recombinant DNA molecule comprising a portion of SEQ ID NO:2 separated by an intron from the complement of the same portion of SEQ ID NO:2. In an alternative embodiment the intron in the recombinant DNA molecule is the IFS intron. In a specific embodiment the recombinant DNA molecule comprises SEQ ID NO:32.

The invention further encompasses methods of supplementing the phytosterol content in food, feed, or dietary supplement. Such methods comprising extracting phytosterol from a transgenic plant or portion thereof having an increased level of one or more phytosterols and adding said extract to the food, feed or dietary supplement. The plant or portion thereof may have a reduced level of one or more triterpene saponins as compared to a transgenic plant not comprising the recombinant DNA molecule. Included in the invention are food, feed, and dietary supplements produced according to the method. Methods of providing at least one phytosterol to an organism, including, but not limited to, humans, monkeys, cows, pigs, horses, sheep, cats, dogs, rats, and mice, by administration of the food, feed or dietary supplements of the invention are also provided.

In another embodiment, the invention relates to a method of producing a composition containing increased level of phytosterols, comprising, a) obtaining a transformed soybean seed, wherein the soybean seed comprises at least one recombinant DNA molecule, wherein expression of said recombinant DNA molecule is sufficient to decrease the activity of an oxidosqualene cyclase and to increase production of phytosterols, b) processing said soybean seed to obtain a composition; c) measuring the phytosterol levels of the composition of b); and comparing the phytosterol levels obtained in c) to the phytosterol levels of a composition prepared with a soybean seed that does not comprise the recombinant DNA molecule.

BRIEF DESCRIPTION OF THE DRAWINGS

The invention can be more fully understood from the following detailed description and the accompanying drawings which form a part of this application.

DEFINITIONS

Figure 1:
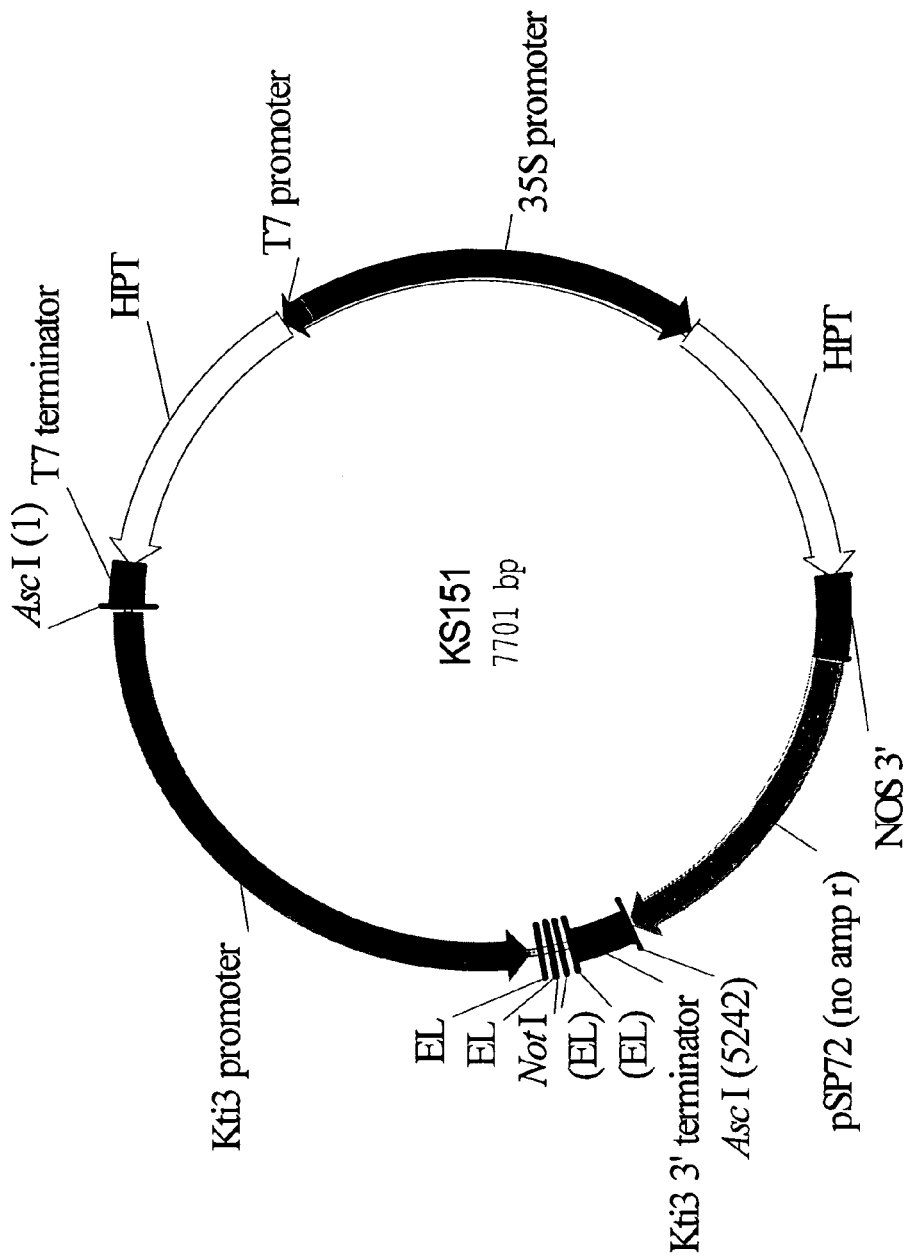
FIG. 1 depicts expression vector pKS151.

In the context of this disclosure, a number of terms shall be utilized.

The term "phytosterol" refers to sterols produced in plants. Phytosterols are further characterized by alkylation of the C-17 side-chain with a methyl or ethyl substituent at the C-24 position. Major phytosterols include, but are not limited to, sitosterol, stigmasterol, campesterol, and brassicasterol.

The term "phytostanol" refers to a fully-saturated subgroup of phytosterols. Phytostanols occur in trace levels in many plant species. Phytosterols can be converted to phytostanols by chemical hydrogenation.

The terms "recombinant DNA molecule," "recombinant DNA fragment," "recombinant DNA expression cassette," "recombinant construct," "expression construct," "chimeric construct," "recombinant DNA construct," "cassette," and "expression cassette" are used interchangeably herein and are nucleic acid fragments. A recombinant construct comprises a combination of nucleic acid fragments, including, and not limited to, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such construct may be used by itself, may be used with at least one other recombinant DNA construct, or may be used in conjunction with a vector.

A "vector" is a polynucleotide fragment to which at least one fragment of DNA from a different organism may be integrated and, which, when introduced into a host cell is capable of either self-replicating or integrating itself in the host chromosome. The choice of vector is dependent upon the method used to transform host cells as is well known to those skilled in the art.

The terms "polynucleotide" and "nucleic acid fragment" are used interchangeably herein. A polynucleotide may be a polymer of RNA or DNA that is single-or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. "Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell. "Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available. "Gene" refers to a nucleic acid fragment that expresses a specific protein or RNA, and may include regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism or a gene that is found in the host organism but in a different location. Foreign genes may be introduced into the host organism by gene transfer. Foreign genes can comprise native genes inserted into a non-native organism, recombinant DNA constructs, or chimeric genes. A "transgene" is an isolated nucleic acid fragment or recombinant DNA construct that has been introduced into the organism by a transformation procedure and may or may not integrate into the genome of the organism.

The term "intron" refers to the DNA nucleotides interrupting the protein-coding sequences of a gene; these nucleotides are transcribed into RNA but are removed from the message before it is translated into a protein. The isoflavone synthase (IFS) intron used herein was obtained from a genomic clone which has the sequence found in the NCBI database Locus AF195818 having General Identifier No. 7288452.

"Coding sequence" refers to a nucleotide sequence that encodes a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences. "Promoter" refers to a region of DNA capable of controlling the expression of a coding sequence or functional RNA. The promoter may consist of proximal and more distal upstream elements. These upstream elements include, but are not limited to, enhancers, repressor binding motifs, tissue-specific motifs, developmental responsive motifs, and hormone responsive motifs. An "enhancer" is a region of DNA capable of stimulating promoter activity. These upstream elements may be innate regions of the promoter or a heterologous element inserted to enhance the level or tissue-specificity of a promoter.

A number of promoters can be used in the practice of the present invention. The promoters can be selected based on the desired outcome. Nucleic acid fragments used to accomplish the invention can be combined in any host organism with a promoter or element that is global, tissue-specific (including, but not limited to, seed-, seed coat-, leaf-, stem-, tuber-, root-, flower-, vacuole-, fruit-, and embryo-specific), constitutive, or inducible (by, e.g., anaerobic conditions, elevated temperature, the presence of light, or spraying with chemicals/hormones).

In some embodiments, promoters or enhancers can be used or modified to accomplish the present invention. For example, endogenous promoters can be altered in vivo by mutation, deletion, and/or substitution (see for example U.S. Pat. No. 5,565,350). Gene expression can be modulated under conditions suitable for host cell growth so as to alter the total concentration and/or alter the composition of the oxidosqualene cyclases of the present invention in a host cell to yield higher phytosterols.

"Tissue-specific" promoters preferentially direct RNA production in particular types of cells or tissues. Promoters that cause a gene to be expressed in most cell types at most times are commonly referred to as "constitutive promoters." New promoters of various types useful in plant cells are constantly being discovered; the compilation by Okamuro, J. K. and Goldberg, R. B. (1989, *Biochemistry of Plants* 15:1-82) provides numerous examples. It is further recognized that since in most cases the exact boundaries of regulatory sequences have not been completely defined, DNA fragments of some variation may have identical promoter activity.

Commonly used promoters include, but are not limited to, the nopaline synthase (NOS) promoter (Ebert et al. (1987) *Proc. Natl. Acad. Sci. U.S.A.* 84:5745-5749), the octapine synthase (OCS) promoter, caulimovirus promoters such as the cauliflower mosaic virus (CaMV) 19S promoter (Lawton et al. (1987) *Plant Mol. Biol.* 9:315-324), the CaMV 35S promoter (Odell et al. (1985) *Nature* 313:810-812), and the figwort mosaic virus 35S promoter; the light inducible promoter from the small subunit of rubisco, the Adh promoter (Walker et al. (1987) *Proc. Natl. Acad. Sci. U.S.A.* 84:6624-66280), the sucrose synthase promoter (Yang et al. (1990) *Proc. Natl. Acad. Sci. U.S.A.* 87:4144-4148), the R gene complex promoter (Chandler et al. (1989) *Plant Cell* 1:1175-1183), and the chlorophyll a/b binding protein gene promoter. Other commonly used promoters are, the promoters for the potato tuber ADPGPP genes, the granule bound starch synthase promoter, the glutelin gene promoter, the maize waxy promoter, the Brittle gene promoter, the Shrunken 2 promoter, the acid chitinase gene promoter, and the zein gene promoters (15 kD, 16 kD, 19 kD, 22 kD, and 27 kD; Perdersen et al. (1982) *Cell* 29:1015-1026). A plethora of promoters is described in PCT Publication No. WO 00/18963, published on Apr. 6, 2000.

The "translation leader sequence" or "leader" refers to a polynucleotide sequence located upstream or 5' of the coding sequence. The translation leader sequence is present in the fully processed mRNA upstream of the translation start site. The translation leader sequence may affect processing of the primary transcript to mRNA, mRNA stability or translation efficiency. Examples of translation leader sequences have been described (Turner, R. and Foster, G. D. (1995) *Mol. Biotechnol.* 3:225-236).

The "3' non-coding region" and "terminator region" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989, *Plant Cell* 1:671-680).

The term "operably linked" and "under the control of" refer to the association of nucleic acid fragments on a single polynucleotide so that the function of one is affected by the function of the other. For example, a promoter is operably linked with a coding sequence when it is capable of affecting the expression of that coding sequence (i.e., that the coding sequence is under the transcriptional control of the promoter). Similarly, a polynucleotide may be under the control of a promoter that is capable of affecting the expression of the polynucleotide. Coding sequences can be operably linked to regulatory sequences in sense or antisense orientation.

"RNA transcript" refers to the product resulting from RNA polymerase-catalyzed transcription of a DNA sequence. When the RNA transcript is a perfect complementary copy of the DNA sequence, it is referred to as the primary transcript. An RNA sequence derived from posttranscriptional processing of the primary transcript and is referred to as the mature RNA. "Messenger RNA (mRNA)" refers to the RNA that is without introns and that can be translated into protein by the cell. "cDNA" refers to a DNA that is complementary to and derived from an mRNA. The cDNA can be single-stranded or converted into the double stranded form using, for example, the Klenow fragment of DNA polymerase 1. "Sense" RNA refers to an RNA transcript that includes the mRNA and can be translated into a polypeptide by the cell. "Antisense RNA" refers to an RNA transcript that is complementary to all or part of a target primary transcript or mRNA. The complement of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The terms "PCR," "polymerase chain reaction," and "PCR amplification" are used interchangeably herein and refer to a technique for the synthesis of easily detectable quantities of specific DNA fragments. It is well known by those skilled in the art as a technique used for the amplification of specific DNA segments (U.S. Pat. Nos. 4,683,195 and 4,800,159).

The term "transformation" refers to the transfer of a nucleic acid fragment into the genome of a host organism. Host organisms containing a transferred nucleic acid fragment are referred to as "transgenic" or "transformed" organisms. "Host cell" refers the cell into which a nucleic acid fragment is transferred and may include a yeast cell, a bacterial cell, an insect cell, or a plant cell. Examples of methods of plant transformation include, among others, *Agrobacterium*-mediated transformation (De Blaere et al. (1987) *Meth. Enzymol.* 143:277) and particle-accelerated transformation (Klein et al. (1987) *Nature (London)* 327:70-73; U.S. Pat. No. 4,945,050). Particle accelerated transformation is also referred to as "gene gun" transformation.

There are a variety of methods for the regeneration of plants from plant tissue. The particular method of regeneration will depend on the starting plant tissue and the particular plant species to be regenerated.

The regeneration, development and cultivation of plants from single transgenic plant cells or from various transgenic explants is well known in the art (Weissbach and Weissbach, In.: Methods for Plant Molecular Biology, (Eds.), Academic Press, Inc., San Diego, Calif. (1988)). This regeneration and growth process typically includes the steps of selection of transgenic cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The term "event" refers to a unique incidence of transformation and multiple, identical plants can be regenerated from a single event.

The term "T0 plant" refers to a primary transformant regenerated from the initially transformed host cell. The term "T1 seed" refers to the seed produced by a "T0 plant."

The term "progeny" refers to the plants and seed obtained after selfing or crossing a plant of interest. The first generation progeny from T0 plants are referred to as "T1 plants", the next generation is referred to as "T2 plants" and so on.

Preferably, the regenerated plants are self-pollinated to provide homozygous transgenic plants. Pollen obtained from the regenerated plants may also be crossed to plants of agronomically important lines. Conversely, pollen from plants of these agronomically important lines is used to pollinate regenerated plants. A transgenic plant of the present invention, comprising a decreased activity of at least one oxidosqualene cyclase sufficient to increase the levels of phytosterols in said transgenic plant, is cultivated using methods well known to one skilled in the art.

The term "expression," as used herein refers to the transcription and stable accumulation of mRNA or RNA derived from a polynucleotide of the invention. Expression may also refer to translation of mRNA into a polypeptide.

The terms "altered levels" and "altered expression" refer to the production of gene product(s) in transgenic organisms in amounts or proportions that differ from that of non-transformed organisms or organisms transformed with nucleic acid fragments other than those in the current invention.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989.

An "allele" is one of several alternative forms of a gene occupying a given locus on a chromosome. When the alleles present at a given locus on a pair of homologous chromosomes in a diploid plant are the same that plant is "homozygous" at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

As stated herein, "suppression" refers to the reduction of the level of enzyme or enzyme activity detectable in a transgenic plant when compared to the level of enzyme or enzyme activity detectable in a plant not transformed with a recombinant DNA of the invention. This reduction may be due to the decrease in translation of the native mRNA into an active enzyme. It may also be due to the transcription of the native DNA into decreased amounts of mRNA and/or to rapid degradation of the native mRNA. Screening to obtain lines displaying the desired phenotype may be accomplished by Southern analysis of DNA, Northern analysis of mRNA expression, RT-PCR, immunoblotting analysis of protein expression, or phenotypic analysis, among others.

"Antisense inhibition" refers to the production of antisense RNA transcripts capable of suppressing the expression of the target protein. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence. "Cosuppression" refers to the production of sense RNA transcripts capable of suppressing the expression of identical or substantially similar native genes (U.S. Pat. No. 5,231,020). Co-suppression constructs in plants have been previously designed by focusing on overexpression of a nucleic acid sequence having homology to a native mRNA, in the sense orientation, which results in the reduction of all RNA having homology to the sequence. "Antisense inhibition" refers to the production of antisense RNA transcripts capable of suppressing the expression of the target protein. Plant viral sequences may be used to direct the suppression of proximal mRNA encoding sequences (PCT Publication WO 98/36083 published on Aug. 20, 1998). Chimeric genes encoding sense and antisense RNA molecules comprising nucleotide sequences respectively homologous and complementary to at least a part of the nucleotide sequence of the gene of interest and wherein the sense and antisense RNA are capable of forming a double stranded RNA molecule or "Hairpin" structure have been described (PCT Publication WO 99/53050 published on Oct. 21, 1999). For review of hairpin suppression see Wesley, S. V. et al. (2003) Methods in Molecular Biology, Plant Functional Genomics: Methods and Protocols 236:273-286. The use of poly-T and poly-A sequences to generate the stem in the stem-loop structure has also been described (WO 02/00894 published Jan. 3, 2002). Yet another variation includes using synthetic repeats to promote formation of a stem in the stem-loop structure. Transgenic organisms prepared with such recombinant DNA fragment show reduced levels of the protein encoded by the polynucleotide from which the nucleotide fragment forming the loop is derived as described in PCT Publication WO 02/00904, published Jan. 3, 2002. The use of constructs having convergent promoters directing transcription of gene-specific sense and antisense RNAs inducing gene suppression has also been described (see for example Shi, H. et al. (2000) RNA 6:1069-1076; Bastin, P. et al. (2000) J. Cell Sci. 113: 3321-3328; Giordano, E. et al. (2002) Genetics 160:637-648; LaCount, D. J. and Donelson, J. E. U.S. patent Application No. 20020182223, published Dec. 5, 2002; Tran, N. et al. (2003) BMC Biotechnol. 3:21; and Applicant's U.S. Provisional Application No. 60/578,404, filed Jun. 9, 2004).

Other methods for suppressing an enzyme include, but are not limited to, use of polynucleotides that may form a catalytic RNA or may have ribozyme activity (U.S. Pat. No. 4,987,071 issued Jan. 22, 1991), and micro RNA (also called miRNA) interference (Javier et al. (2003) Nature 425:257-263).

The terms "soy" and "soybean" are used interchangeably herein. Within the scope of the invention are soybean plants (*Glycine soja* or *Glycine max*), seeds, and plant parts obtained from such transformed plants. Also within the scope of the invention are soybean products derived from the transformed plants such as grain, protein products, oils, and products including such soybean products like feed and foodstuffs. Plant parts include differentiated and undifferentiated tissues, including and not limited to, roots, stems, shoots, leaves, pollen, seeds, tumor tissue, and various forms of cells and cultures such as single cells, protoplasts, embryos, and callus tissue. The plant tissue may be in plant or in organ, tissue or cell culture.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNα-containing organelle, of a host organism resulting in gene expression without integration or stable inheritance. The term "transformation" as used herein refers to both stable transformation and transient transformation.

A "portion capable of decreasing the activity of oxidosqualene cyclase" refers to a portion or subfragment of an isolated nucleic acid fragment in which the ability to alter gene expression or produce a certain phenotype is retained whether or not the fragment or subfragment may be translated into an active enzyme. For example, a portion may be a portion capable of suppressing expression of a native gene. A fragment or subfragment may be used in the design of chimeric genes or recombinant DNA constructs to produce the desired phenotype in a transformed plant. Chimeric genes may be designed for use in suppression by linking a nucleic acid fragment or subfragment thereof, whether or not it is translated into an active enzyme, in the sense or antisense orientation relative to a plant promoter sequence. Recombinant DNA fragments may be designed to comprise nucleic acid fragments capable of promoting formation of a stem-loop structure. In a stem-loop structure either the loop or the stem comprises a portion of the gene to be suppressed. The nucleic acid fragment should have a stretch of at least about 20 contiguous nucleotides that are identical to the gene to be suppressed. The stretch of contiguous nucleotides may be any number, from at least about 20, or about 22, or about 25, or about 32, to the size of the entire gene to be suppressed.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989.

DETAILED DESCRIPTION OF THE INVENTION

The present invention relates to compositions having increased phytosterol content that were obtained from transgenic plants and/or plant parts and methods thereof. The plants or plant parts may have reduced levels of triterpene saponins.

In the present invention the increased phytosterol levels are obtained by redirecting the flux of oxidosqualenes by suppressing the activity of an oxidosqualene cyclase at a step in the pathway downstream of HMG CoA reductase.

An embodiment of the present invention concerns a method of producing a composition containing increased levels of phytosterols, comprising, obtaining a transgenic plant or portion thereof, wherein the plant has a decreased level of at least one triterpene saponin due to the presence of a recombinant DNA molecule comprising at least a portion of at least one gene that encodes an oxidosqualene cyclase that catalyzes the cyclization of 2,3-oxidosqualene to form cyclyzed triterpene, processing said plant or portion thereof to obtain a composition; measuring the phytosterol levels of the composition, and comparing the phytosterol levels of the composition with the phytosterol levels of a composition prepared with a plant not comprising the recombinant DNA molecule. The plant may comprise at least one recombinant DNA molecule comprising a promoter operably linked to at least a portion of at least one oxidosqualene cyclase gene, wherein expression of said recombinant DNA molecule is sufficient to decrease production of triterpene saponins and to increase production of a phytosterol as compared to a plant that does not comprise the recombinant DNA molecule. The composition may contain at least 1.5 times as much of phytosterol as a composition prepared from a plant or plant part not comprising said recombinant DNA molecule.

Transgenic plants with increased phytosterol levels by manipulation of cellular biosynthetic pathways are the subject of several Patents, Patent Applications, and Publications. For example U.S. Pat. No. 5,306,862; U.S. Pat. No. 5,349, 126; U.S. Pat. No. 5,365,017; U.S. Pat. No. 5,589,619; U.S. Pat. No. 6,822,142; PCT publication WO 01/04314, published Jan. 18, 2001; PCT publication WO 00/617,771, published Oct. 19, 2000; PCT publication WO 02/61,072, published Aug. 08, 2002; and Schaller et al. (1995) Plant Physiol. 109:761-770; among others.

Another embodiment concerns a method of producing a phytosterol-containing extract, wherein the extract contains an increased level of phytosterols, comprising, obtaining a transformed plant or portion thereof, wherein the plant has a decreased activity of an oxidosqualene cyclase sufficient to increase the levels of phytosterols, processing said plant or portion thereof to obtain oil; and extracting the phytosterol-containing extract from the resulting oil. The plant may comprise at least one recombinant DNA molecule comprising a promoter operably linked to at least a portion of at least one oxidosqualene cyclase gene, wherein expression of said recombinant DNA molecule is sufficient to decrease production of triterpene saponins and to increase production of phytosterols as compared to a plant that does not comprise the recombinant DNA molecule.

It may be possible to prepare the composition containing an increased level of phytosterols from any part of the plant including, and not limited to, the seed, leaf, stem, root, or flower.

The plants used to prepare a composition of the invention, such as oil, comprise a recombinant DNA molecule sufficient to decrease activity of an oxidosqualene cyclase. The plants may have an decreased production of a triterpene saponin.

In a specific embodiment, the processed transgenic plant has a decreased level of at least one triterpene saponin due to the presence of a recombinant DNA molecule comprising at least a portion of at least one gene that encodes at least one oxidosqualene cyclase that catalyzes the cyclization of 2,3-oxidosqualene to form a cyclyzed triterpene including, but not limited to, lupeol, β-amyrin, α-amyrin, isomultiflorenol, thalianol, and dammarenediol or any combination thereof. In a preferred embodiment, the transgenic plant has a recombinant DNA molecule comprising at least a portion of at least one gene that encodes β-amyrin synthase. β amyrin synthases have been functionally characterized from Panax ginseng (Kushiro, T., et al. (1998) Eur. J. Biochem. 256:238-244); pea (Morita, M., et al. (2000) Eur. J. Biochem. 267: 3453-3460), oat (Haralampidis, K., et al. (2001) Proc. Natl. Acad. Sci. U.S.A. 98:13431-13436), soybean (PCT Publication WO 01/66,773, published Sep. 13, 2001), Glycyrrhiza glabra (Hayashi, H. et al. (2001) Biol. Pharm. Bull. 24:912-916), *Betula platyphylla* (Zhang, H. et al. (2003) Biol. Pharm. Bull. 26:642-650), and Medicago truncatula (Iturbe-Ormaetxe, I., et al. (2003) Plant Mol. Biol. 51:731-743). In a preferred embodiment, the processed transgenic plant has a recombinant DNA molecule comprising at least a portion of at least one gene that encodes a β amyrin synthase where the β amyrin synthase has the amino acid sequence encoded by SEQ ID NO:2. In an embodiment the recombinant DNA molecule may comprise SEQ ID NO:2. In another embodiment the recombinant DNA molecule may comprise a portion of SEQ ID NO:2 and a portion of SEQ ID NO:1.

In a further embodiment the transgenic plant comprises a recombinant DNA molecule comprising a portion of SEQ ID NO:2 separated by an intron from the complement of the same portion of SEQ ID NO:2. In an alternative embodiment the intron in the recombinant DNA molecule is the isoflavone synthase (IFS) intron. Polynucleotides encoding IFS, including a soybean genomic sequence and its intron has been described (PCT publication WO 00/44909 published 3 August, 2000; Jung, W. et al. (2000) Nat. Biotechnol. 18:208-

212). In an embodiment the recombinant molecule comprises SEQ ID NO:32. Other examples of oxidosqualene cyclases are disclosed in U.S. Patent Publication 20030208791, which is incorporated by reference, and by Iturbe-Ormaetxe et al., (2003) Plant Mol. Biol. 51:731-743.

A phytosterol-containing composition or extract produced according to the methods of the invention is an embodiment of the invention.

Another embodiment of the invention relates to a method of supplementing the phytosterol content in a food, feed or dietary supplement comprising extracting phytosterol from a transgenic plant or portion thereof of the present invention, and adding said extract to the food, feed or dietary supplement. The transgenic plant may comprises at least one recombinant DNA molecule comprising a promoter operably linked to at least a portion of at least one oxidosqualene cyclase gene, wherein expression of said recombinant DNA molecule is sufficient to decrease production of at least one triterpene saponin and to increase production of phytosterols as compared to a plant that does not comprise the recombinant DNA molecule. Food, feed, and dietary supplements produced according to the methods of the invention are also included.

One embodiment of the invention is a method of providing phytosterols to an organism (including, but not limited to, humans, monkeys, cows, pigs, horses, sheep, cats, dogs, rats, and mice) by providing a dietary supplement, food or feed comprising phytosterol extracted from a transformed plant or portion thereof, wherein the plant comprises at least one recombinant DNA molecule comprising a promoter operably linked to at least a portion of at least one oxidosqualene cyclase gene, wherein expression of said recombinant DNA molecule is sufficient to decrease production of triterpene saponins and to increase production of phytosterols.

Any method can be used to process the transgenic plants of the invention or parts thereof to make compositions of the invention. In preferred embodiments, transgenic plants of the invention are soybeans and compositions containing increased phytosterols are isolated therefrom. Methods for processing soybeans are well known in the art. Compositions containing increased levels of phytosterols may be derived from the plants comprising a recombinant DNA molecule sufficient to decrease production of triterpene saponins by pressing the plant material or by processing the soybean seeds as follows. Seeds are cleaned to remove foreign material and are dried to 9.5% moisture, the seeds are then cracked, heated to remove the flakes, passed through a roller mill, and extracted with a solvent which in most cases is hexane (see, for example the Soybean Processing Fact Sheet provided by the United Soybean Board). Phytosterols normally partition with the oil fraction. Soybean oil may be prepared by one of many methods known in the art. For example, the oil/hexane mixture is separated from the flakes and then the hexane evaporated to leave soybean oil. Soybean oil may also be prepared by mechanically squeezing the oil from heated soybeans or by extruding-expelling. Extruding-expelling is a process by which the soybeans are first treated with a dry extruder and then the oil is mechanically recovered (Nelson et al. (1987) J. Am. Oil Chem. Soc. 64:1341-1347).

Compositions of the invention may have increased levels of at least one phytosterol and may be isolated from transgenic plants or portions thereof with increased levels of at least one phytosterol. In one embodiment, the level of one phytosterol (e.g., isofucosterol, sitosterol, stigmasterol, campesterol, cholesterol, cycloartenol, or dihydrobrassicasterol) is increased. In a preferred embodiment, the level of more than one phytosterol is increased. In a more preferred embodiment, the total level of phytosterol in a plant is increased. The level of increase in the one or more phytosterols is at least 1.0, 1.5, 2.0, 2.5, 3.0, 3.5, 5.0, 10 fold by weight as compared to the level in a plant not comprising a recombinant DNA molecule of the invention.

Any method for extracting and/or measuring phytosterols in a plant or composition therefrom may be used. Phytosterols are extracted by common methods used in the extraction of lipids. Free phytosterols may be quantitatively extracted from crude soybean oils using non-polar solvents such as hexane or mixtures of chloroform and methanol. Phytosterols may be recovered from the deodorizer distillate of vegetable oils by crystallization (Moreira and Baltana (2004) J. Am. Oil. Chem. Soc. 81:161-167); or by separation using supercritical carbon dioxide (Mendes et al. (2005) J. Supercritical Fluids 34:157-162). Sterols may also be recovered using a lipase-catalyzed reaction and distillation (Nagao, et al. (2004) Lipids 39:789-794).

Methods of measuring phytosterols are well known in the art. These include high performance liquid chromatography (HPLC) methods which have been developed to separate and analyze phytosterol lipid classes (see, for example, the review by Moreau et al. (2002) Prog. Lipid Res. 41:457-500); gas chromatography-mass spectrometry (GC-MS); thin layer chromatography (TLC); or gas-liquid-chromatography (Marshall J A, et al. (2001) Phytochemistry 58:423428.); liquid chromatography/atmospheric pressure chemical ionization-mass spectrometry( (LC/APCI-MS) (Rozenberg R. et al. (2003) J. Cereal Sci. 38:189-197) among other methods.

Compositions of the invention may have increased levels of at least one phytosterol and may be isolated from transgenic plants or portions thereof with decreased levels of at least one triterpene saponin. The decreased triterpene saponin levels refer to triterpene saponin levels lower than those found in plants not comprising a recombinant DNA molecule. The decreased triterpene saponin levels may be at least 100 ppm lower, 250 ppm lower, 500 ppm lower, 750 ppm lower, 1000 ppm lower, 1250 ppm lower, 1500 ppm lower, 3000 ppm lower, or any integer thereof.

The level of triterpene saponins can be determined by measurement of sapongenols. Measurement of sapongenols directly correlates to the level of triterpene saponins. Sapongenols are derived from triterpene saponins via in vitro acid hydrolysis and their measurement provides a relative value which can be directly correlated into the amount of triterpene saponins present in the tissue from which the saponins are extracted.

The triterpene saponin levels can be measured using techniques known in the art. For example, one could use HPLC-MS or HPLC with a light scattering detector (see for example Rupasinghe, H. P. et al., (2003) J. Agri. Food Chem. 51:5888-5894). Alternatively, one could use HPLC with a UV detector (Hubert J, et al. (2005) J. Agric. Food Chem. 53:3923-3930). Other methods include using GC-FAB. (see for example Gee et al. (1993) J Sci Food Agric. 63:201-209). Other methods involve separating saponins using thin layer chromatography (TLC) coupled with densitometry (see for example Oleszek W A. (2002) J. Chromatogr. A 967:147-162.; Gurfinkel D M, and Rao A V (2002) J. Agric. Food Chem. 50:426-430.

Any method may be used to decrease the activity and/or expression of the at least one oxidosqualene cyclase that catalyzes the cyclization of 2,3-oxidosqualene to form cyclyzed triterpene. In a preferred embodiment, the activity and/or expression of at least one oxidosqualene cyclase that catalyzes the cyclization of 2,3-oxidosqualene to form cyclyzed triterpene is decreased by introduction of a transgene. The level of activity and/or expression of the oxidosqualene cyclase targeted by the transgene is decreased when compared to the level of enzyme activity and/or expression detectable in a plant not containing the transgene. This reduction may be due to the decrease in translation of the native mRNA into an active enzyme. It may also be due to the transcription of the native DNA into decreased amounts of mRNA and/or to rapid degradation of the native mRNA. The term "native enzyme" refers to an enzyme that is produced naturally in the desired cell.

In one embodiment, cosuppression is used to decrease the expression of the at least one oxidosqualene cyclase that catalyzes the cyclization of 2,3-oxidosqualene to form cyclyzed triterpene. Cosuppression refers to the production of sense RNA transcripts capable of suppressing the expression of identical or substantially similar native genes (U.S. Pat. No. 5,231,020). Co-suppression constructs in plants have been previously designed by focusing on overexpression of a nucleic acid sequence having homology to a native mRNA, in the sense orientation, which results in the reduction of all RNA having homology to the overexpressed sequence (see Vaucheret et al. (1998) *Plant J.* 16:651-659; and Gura (2000) *Nature* 404:804-808).

In another embodiment, antisense inhibition is used to decrease the expression of the at least one oxidosqualene cyclase that catalyzes the cyclization of 2,3-oxidosqualene to form cyclyzed triterpene. Antisense inhibition refers to the production of antisense RNA transcripts capable of suppressing the expression of the target protein. Antisense nucleic acid molecules are molecules which are complementary to all or part of a sense nucleic acid encoding the target protein (i.e., oxidosqualene cyclase), e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids. An antisense oligonucleotide can be, for example, about 5, 10, 15, 20, 25, 30, 35, 40, 45 or 50 nucleotides in length.

In another embodiment, hairpin structures are used to decrease the expression of the at least one oxidosqualene cyclase that catalyzes the cyclization of 2,3-oxidosqualene to form cyclyzed triterpene. Chimeric genes encoding sense and antisense RNA molecules comprising nucleotide sequences respectively homologous and complementary to at least a part of the nucleotide sequence of the gene of interest and wherein the sense and antisense RNA are capable of forming a double stranded RNA molecule or "Hairpin" structure have been described (PCT Publication WO 99/53050 published on Oct. 21, 1999). For review of hairpin suppression see Wesley, S. V. et al. (2003) Methods in Molecular Biology, Plant Functional Genomics: Methods and Protocols 236:273-286. A construct comprising at least 30 nucleotides from a gene to be suppressed (or its homolog) separated from another copy of the same at least 30 nucleotides by a random nucleotide sequence has also effectively been used for suppression (WO 99/61632 published on Dec. 2, 1999). The use of poly-T and poly-A sequences to generate the stem in the stem-loop structure has also been described (WO 02/00894 published Jan. 3, 2002). Yet another variation includes using synthetic repeats to promote formation of a stem in the stem-loop structure. Transgenic organisms prepared with such recombinant DNA fragment show reduced levels of the protein encoded by the polynucleotide from which the nucleotide fragment forming the loop is derived as described in PCT Publication WO 02/00904, published Jan. 3, 2002.

In another embodiment, ribozymes are used to decrease the expression of the at least one oxidosqualene cyclase that catalyzes the cyclization of 2,3-oxidosqualene to form cyclyzed triterpene. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes; described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding oxidosqualene cyclase can be designed based upon the nucleotide sequence of oxidosqualene cyclase. For example, a derivative of a Tetrahymena L-19 IVS RNA can be constructed in which the nucleotide sequence of the active site is complementary to the nucleotide sequence to be cleaved in U.S. Pat. Nos. 4,987,071 and 5,116,742. Alternatively, an mRNA encoding a oxidosqualene cyclase can be used to select a catalytic RNA having a specific ribonuclease activity from a pool of RNA molecules. See, e.g., Bartel and Szostak, 1993, Science 261: 1411.

It is well understood by those skilled in the art, that other sequences commonly used in molecular manipulations may be used here. These sequences may include any seed-specific promoter, any structure that promotes stem-loop formation, any portion of the gene or genes of interest inserted in sense or anti-sense orientation with respect to the promoter and stem-loop structure, and any termination signal. It is also well known by those skilled in the art that gene suppression may result from sequences other than those that promote stem-loop formation.

In another embodiment, RNA interference is used to decrease the expression of the at least one oxidosqualene cyclase that catalyzes the cyclization of 2,3-oxidosqualene to form cyclyzed triterpene. RNA interference (RNAi) is defined as the ability of double-stranded RNA (dsRNA) to suppress the expression of a gene corresponding to its own sequence. RNAi is also called post-transcriptional gene silencing or PTGS. Since the only RNA molecules normally found in the cytoplasm of a cell are molecules of single-stranded mRNA, the cell has enzymes that recognize and cut dsRNA into fragments containing 21-25 base pairs (approximately two turns of a double helix). The antisense strand of the fragment separates enough from the sense strand so that it hybridizes with the complementary sense sequence on a molecule of endogenous cellular mRNA. This hybridization triggers cutting of the mRNA in the double-stranded region, thus destroying its ability to be translated into a polypeptide. Introducing dsRNA corresponding to a particular gene thus knocks out the cell's own expression of that gene in particular tissues and/or at a chosen time.

Any method can be used for transforming a plant or plant cell with a nucleic acid molecule to make a transgenic plant of the present invention. Nucleic acid molecules can be incorporated into plant DNA (e.g., genomic DNA or chloroplast DNA) or be maintained without insertion into the plant DNA (e.g., through the use of artificial chromosomes). The transgenic nucleic acids may be under the control of any type of promoter including, but not limited to, global, tissue-specific (including, but not limited to, seed-, seed coat-, leaf-, stem-, tuber-, root-, flower-, vacuole-, fruit-, and embryo-specific), constitutive, and inducible (by, e.g., anaerobic conditions, elevated temperature, the presence of light, or spraying with chemicals/hormones). Suitable methods of introducing nucleic acid molecules into plant cells include microinjection (Crossway et al., 1986, *Biotechniques* 4:320-334); electroporation (Riggs et al., 1986, *PNAS* 83:5602-5606; D'Halluin et al., 1992, *Plant Cell* 4:1495-1505); Agrobacterium-mediated transformation (U.S. Pat. Nos. 5,563,055 and 5,981,840, Osjoda et al., 1996, *Nature Biotechnology* 14:745-750; Horsch et al., 1984, Science 233:496498, Fraley et al., 1983, *PNAS* 80:4803, and *Gene Transfer to Plants*, Potrykus, ed., Springer-Verlag, Berlin 1995); direct gene transfer (Paszkowski et al., 1984, *EMBO J.* 3:2717-2722); ballistic particle acceleration (U.S. Pat. Nos. 4,945,050; 5,879,918; 5,886, 244; 5,932,782; Tomes et al., 1995, "Direct DNA Transfer into Intact Plant Cells via Microprojectile Bombardment, in *Plant Cell, Tissue, and Organ Culture: Fundamental Methods*, ed. Gamborg and Phillips, Springer-Verlag, Berlin; and McCabe et al., 1988, *Biotechnology* 6:923-926); virus-mediated transformation (U.S. Pat. Nos. 5,889,191, 5,889,190, 5,866,785, 5,589,367 and 5,316,931); pollen transformation (De Wet et al., 1985, in *The Experimental Manipulation of Ovule Tissues*, ed. Chapman et al., Longman, N.Y., pp. 197-209); Lec 1 transformation (U.S. patent application Ser. No. 09/435,054; International Publication No. WO 00/28058); whisker-mediated transformation (Kaeppler et al., 1990, *Plant Cell Reports* 9:415-418; Kaeppler et al., 1992, *Theor. Appl. Genet.* 84:560-566); and chloroplast transformation technology (Bogorad, 2000, *Trends in Biotechnology* 18: 257-263; Ramesh et al., 2004, *Methods Mol Biol.* 274:301-7; Hou et al., 2003, *Transgenic Res.* 12:111-4; Kindle et al., 1991, *PNAS* 88:1721-5; Bateman and Purton, 2000, *Mol Gen Genet* 263:404-10; Sidorov et al., 1999, *Plant J.* 19:209-216).

The choice of transformation protocols used for generating transgenic plants and plant cells can vary depending on the type of plant or plant cell, i.e., monocot or dicot, targeted for transformation. Examples of transformation protocols particularly suited for a particular plant type include those for: potato (Tu et al., 1998, *Plant Molecular Biology* 37:829-838; Chong et al., 2000, *Transgenic Research* 9:71-78); soybean (Christou et al., 1988, *Plant Physiol.* 87:671-674; McCabe et al., 1988, *BioTechnology* 6:923-926; Finer and McMullen, 1991, *In Vitro Cell Dev. Biol.* 27P:175-182; Singh et al., 1998, *Theor. Appl. Genet.* 96:319-324); maize (Klein et al., 1988, *Proc. Natl. Acad. Sci.* 85:4305-4309; Klein et al., 1988, *Biotechnology* 6:559-563; Klein et al., 1988, *Plant Physiol.* 91:440-444; Fromm et al., 1990, *Biotechnology* 8:833-839; Tomes et al., 1995, "Direct DNA Transfer into Intact Plant Cells via Microprojectile Bombardment," in *Plant Cell, Tissue, and Organ Culture: Fundamental Methods*, ed. Gamborg (Springer-Verlag, Berlin)); cereals (Hooykaas-Van Slogteren et al., 1984, *Nature* 311:763-764; U.S. Pat. No. 5,736,369).

In some embodiments, more than one construct is used for transformation in the generation of transgenic plants and plant cells.

Transgenic plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in the art (e.g., Evans et al., *Protoplasts Isolation and Culture, Handbook of Plant Cell Culture*, pp. 124-176, MacMillilan Publishing Company, New York, 1983; and Binding, Regeneration of Plants, Plant Protoplasts, pp. 21-73, CRC Press, Boca Raton, 1985). Regeneration can also be obtained from plant callus, explants, organs, or parts thereof. Such regeneration techniques are also described in the art (e.g., Klee et al. 1987, Ann. Rev. of Plant Phys. 38:467-486).

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in methods of the present invention includes the class of higher and lower plants amenable to transformation techniques, including angiosperms (monocotyledonous and dicotyledonous plants), gymnosperms, ferns, and multicellular algae. Plants of a variety of ploidy levels, including aneuploid, polyploid, diploid, haploid and hemizygous plants are also included.

The transgenes of the invention can be used to confer desired traits on essentially any plant. Thus, the invention has use over a broad range of plants, including species from the genera *Agrotis, Allium, Ananas, Anacardium, Apium, Arachis, Asparagus, Athamantha, Atropa, Avena, Bambusa, Beta, Brassica, Bromus, Browaalia, Camellia, Cannabis, Carica, Ceratonia. Cicer, Chenopodium, Chicorium, Citrus, Citrullus, Capsicum, Carthamus, Cocos, Coffea, Coix, Cucumis, Cucurbita, Cynodon, Dactylis, Datura, Daucus, Dianthus, Digitalis, Dioscorea, Elaeis, Eliusine, Euphorbia, Festuca, Ficus, Fragaria, Geranium, Glycine, Graminae, Gossypium, Helianthus, Heterocallis, Hevea, Hibiscus, Hordeum, Hyoscyamus, Ipomoea, Lactuca, Lathyrus, Lens, Lilium, Linum, Lolium, Lotus, Lupinus, Lycopersicon, Macadamia, Macrophylla, Malus, Mangifera, Manihot, Majorana, Medicago, Musa, Narcissus, Nemesia, Nicotiana, Onobrychis, Olea, Olyreae, Oryza, Panicum, Panicum, Panieum, Pannisetum, Pennisetum, Petunia, Pelargonium, Persea, Pharoideae, Phaseolus, Phleum, Picea, Poa, Pinus, Pistachia, Pisum, Populus, Pseudotsuga, Pyrus, Prunus, Pseutotsuga, Psidium, Quercus, Ranunculus, Raphanus, Ribes, Ricinus, Rhododendron, Rosa, Saccharum, Salpiglossis, Secale, Senecio, Setaria, Sequoia, Sinapis, Solanum, Sorghum, Stenotaphrum, Theobromus, Trigonella, Trifolium, Trigonella, Triticum, Tsuga, Tulipa, Vicia, Vitis, Vigna,* and *Zea.*

In specific embodiments, transgenic plants are soybean, maize, potato, and rice.

Transgenic plants may be grown and pollinated with either the same transformed strain or different strains. Two or more generations of the plants may be grown to ensure that expression of the desired nucleic acid molecule, polypeptide and/or phenotypic characteristic is stably maintained and inherited. One of ordinary skill in the art will recognize that after the nucleic acid molecule of the present invention is stably incorporated in transgenic plants and confirmed to be operable, it can be introduced into other plants by sexual crossing. Any of a number of standard breeding techniques can be used, depending upon the species to be crossed.

The choice of recombinant expression construct is dependent upon the method that will be used to transform host cells. The skilled artisan is well aware of the genetic elements that must be present on the recombinant expression construct in order to successfully transform, select and propagate host cells. The skilled artisan will also recognize that different independent transformation events may be screened to obtain lines displaying the desired expression level and pattern. Such screening may be accomplished by, but is not limited to, Southern analysis of DNA, Northern analysis of mRNA expression, Western analysis of protein expression, or phenotypic analysis.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Preparation of Chimeric Oxidosqualene Cyclase Plasmids

Chimeric recombinant DNA molecules were prepared containing polynucleotides from at least a portion of one or more oxidosqualene cyclase genes to be used in transformation of soybean embryos. Construction of plasmids AC18, PHP20767 and PHP21157 follows.

Construction of Plasmid AC18

Plasmid AC18 was prepared containing a seed-specific expression promoter followed by nucleotide sequences that promote formation of a stem-loop structure (comprising nucleotide sequences derived from portions of two oxidosqualene cyclase genes forming the loop flanked by nucleotide sequences that promote formation of a stem) followed by a transcription termination signal. Plasmid AC18 was prepared by inserting at the unique Not I site of the seed-specific expression vector pKS151 (described below) a polynucleotide fragment comprising portions of two oxidosqualene cyclase genes ("oSC chimera") which were obtained from clones sah1c.pk002.n23 and src3c.pk024.m11. Clones sah1c.pk002.n23 and src3c.pk024.m11 have been previously identified as encoding oxidosqualene cyclases (PCT publication No. WO01/66773, published 13 Sep. 2001) where the cDNA insert in clone src3c.pk024.m11 was further identified as encoding a α-amyrin synthase due to its demonstrated ability of producing β-amyrin. SEQ ID NO:1 represents the nucleotide sequence of the cDNA insert from clone sah1c.pk002.n23 and SEQ ID NO:2 represents the nucleotide sequence of the cDNA insert from clone src3c.pk024.m11.

The seed-specific expression vector pKS151 is depicted in FIG. 1 and has been described in PCT Publication No. WO 02/0094 published 3 Jan. 2002. SEQ ID NO:3 represents the nucleotide sequence of vector pKS151. This vector is derived from the commercially available plasmid pSP72 (Promega, Madison, Wis.). Vector pKS151 and comprises a seed-specific expression cassette composed of the promoter and transcription terminator from the gene encoding the kunitz trypsin inhibitor 3 (KTi3; Jofuku, K. D. and Goldberg, R. B. (1989) Plant Cell 1:1079-1093) separated by a unique Not I restriction endonuclease site which is flanked by two copies of a 36-nucleotide sequence ("EL"; set forth in SEQ ID NO:4) at its 5' end and two copies of the inverted repeat of the same 36 nucleotides ("(EL)") at its 3' end. The seed-specific expression cassette includes about 2088 nucleotides upstream (5') from the translation initiation codon and about 202 nucleotides downstream (3') from the translation stop codon of KTi3.

Besides the seed-specific expression cassette described above, vector pKS151 also contains two copies of polynucleotides encoding a protein that provide resistance to the selective agent hygromycin. One of the polynucleotides is under the control of the bacteriophage T7 promoter and allows for selection in bacterial systems such as E. coli. The other polynucleotide is under control of the cauliflower mosaic virus 35S promoter and allows for selection in plant species such as soybean.

The polynucleotide fragment comprising portions of two oxidosqualene cyclase genes was prepared by amplifying a portion of the cDNA insert from clone sah1c.pk002.n23 and amplifying a portion of the cDNA insert from clone src3c.pk024.m11 using primers designed in such a way that the amplification products from the two reactions hybridize to form a chimeric recombinant DNA fragment. A portion of the cDNA insert from clone sah1c.pk002.n23 was amplified using oligonucleotide primers BM1 (SEQ ID NO:5) and BM2 (SEQ ID NO:6). A portion of the cDNA insert from clone src3c.pk024.m11 was amplified using oligonucleotide primers BM3 (SEQ ID NO:7) and BM4 (SEQ ID NO:8).

```
BM1:
5'-GCGGCCGCCAACAATTTAGAAGAGGCTCGG-3'    (SEQ ID NO:5)

BM2:
5'-TTCTTGGAGAAGGACCTAATGGAGGTCATG-3'    (SEQ ID NO:6)

BM3:
5'-GCGGCCGCATGTGGAGGCTGAAGATAGCAG-3'    (SEQ ID NO:7)

BM4:
5'-GTCATGACCTCCATTAGGTCCTTCTCCAAG-3'    (SEQ ID NO:8)
```

Figure 2:
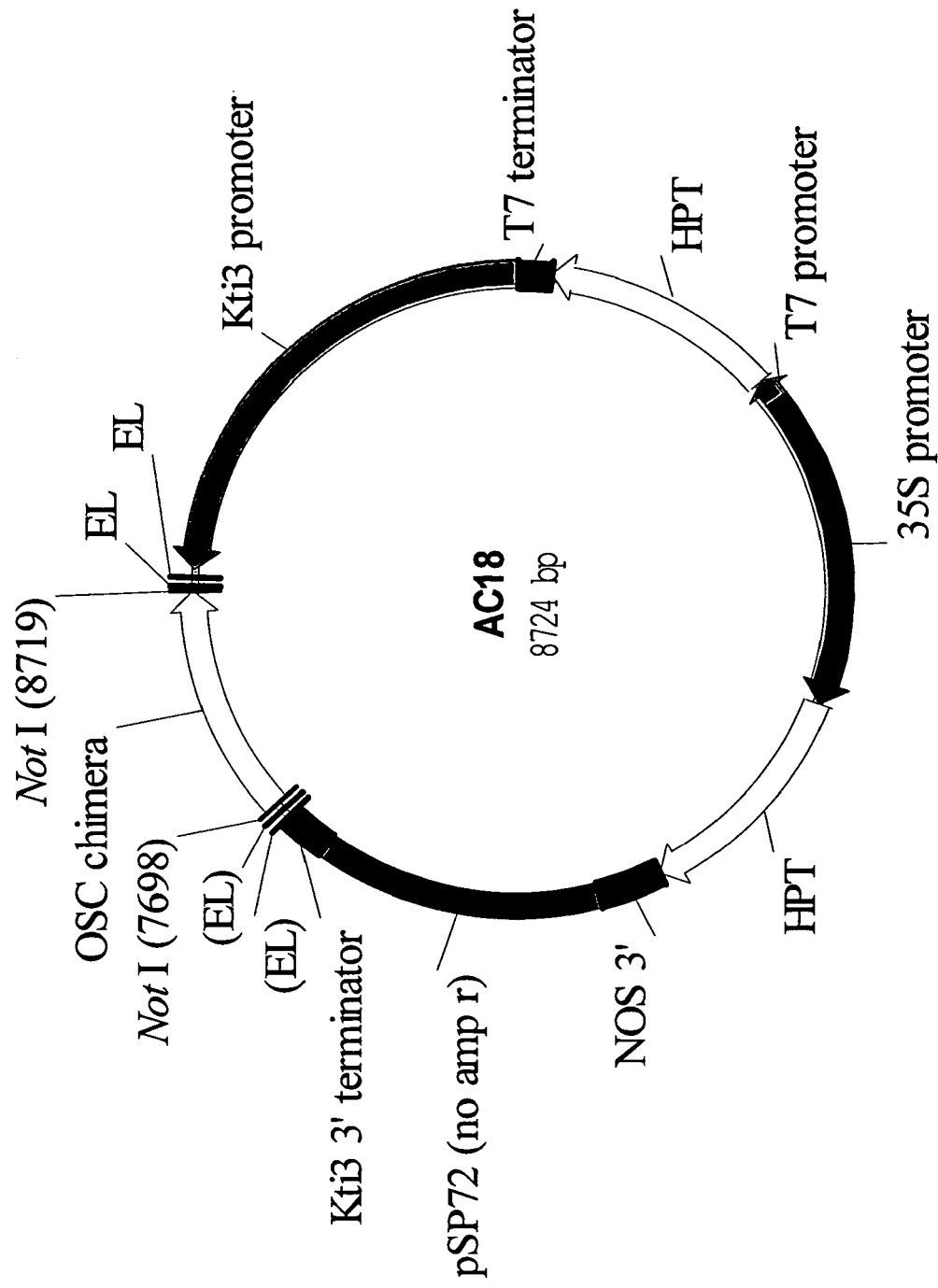
FIG. 2 depicts plasmid AC18.

Primers BM2 and BM3 were designed in such a way that the amplification products of the two reactions hybridize to form a chimeric recombinant DNA fragment. A fresh amplification reaction was assembled using as template a mixture of product from each reaction and primers BM1 and BM4. All amplifications were carried out using the Advantage-GC cDNA PCR kit (Clontech, Palo Alto, Calif.) and a Perkin-Elmer Applied Biosystem GeneAmp PCR System 9700. The resulting amplification product was introduced into plasmid pCR2.1 using the TOPO TA Cloning Kit (Invitrogen) and is shown in SEQ ID NO:9. The amplified product was removed from plasmid pCR2.1 using the restriction enzyme Not I and ligated into the Not I restriction endonuclease site of vector pKS151. Bacterial colonies were selected and grown overnight in LB media and appropriate antibiotic selection. DNA was isolated from the resulting culture using a Qiagen Miniprep Kit according to the manufacturer's protocol and then analyzed by restriction digest. DNA with the appropriate restriction pattern was named plasmid AC18 and used for transformation of somatic soybean embryo cultures as described in Example 2. Plasmid AC18 is depicted in FIG. 2 and SEQ ID NO:10 represents its nucleotide sequence.

B. Construction of Intermediate Plasmid DN10

An intermediate cloning vector, known as plasmid DN10, was constructed in order to assist in the preparation of plasmids PHP20767 and PHP21157. Plasmid DN10 comprises a bacterial origin of replication, bacterial and plant selectable marker gene expression cassettes, and a promoter and terminator separated by a unique Not I restriction endonuclease site. This plasmid was prepared by ligating a fragment comprising a plant selectable marker gene expression cassette and a cassette comprising a promoter and terminator separated by a unique Not I restriction endonuclease site to a fragment comprising the bacterial origin of replication and selectable marker gene. These two fragments were prepared as follows:

The first fragment has 6383 bp, was obtained by Kpn I digestion of pKS231, and SEQ ID NO:11 represents its nucleotide sequence, and it contains two cassettes: 1) a plant selectable marker gene expression cassette, and 2) a cassette comprising a promoter and terminator separated by a unique Not I restriction endonuclease site. The plant selectable marker gene expression cassette comprises a 1.3-Kb DNA fragment that functions as the promoter for a soybean S-adenosylmethionine synthase (SAMS) gene directing expression of a mutant soybean acetolactate synthase (ALS) gene which is followed by the soybean ALS 3' transcription terminator. The 1.3-Kb DNA fragment that functions as the promoter for a soybean SAMS gene has been described in PCT Publication No. WO 00/37662, published 29 Jun., 2000. The mutant soybean ALS gene ("mALS") encodes an enzyme that is resistant to inhibitors of ALS, such as sulfonylurea herbicides.

Mutant plant ALS genes encoding enzymes resistant to sulfonylurea herbicides are described in U.S. Pat. No. 5,013,659. One such mutant is the tobacco SURB-Hra gene, which encodes an herbicide-resistant ALS with two substitutions in the amino acid sequence of the protein. This tobacco herbicide-resistant ALS contains alanine instead of proline at position 191 in the conserved "subsequence B" and leucine instead of tryptophan at position 568 in the conserved "subsequence F" (U.S. Pat. No. 5,013,659; Lee et al., 1988, *EMBO J.* 7:1241-1248).

The mutant soybean ALS gene was constructed using a polynucleotide for a soybean ALS to which the two Hrα-like mutations were introduced by site directed mutagenesis. Thus, this recombinant DNA fragment will translate to a soybean ALS having alanine instead of proline at position 183 and leucine instead of tryptophan at position 560. The deduced amino acid sequence of the mutant soybean ALS present in the mutant ALS gene is set forth in SEQ ID NO:12. During construction of SAMS promoter-mutant ALS expression cassette, the coding region of the soybean ALS gene was extended at the 5' end by five additional codons, resulting in five amino acids, added to the amino-terminus of the ALS protein (amino acids 1 through 5 of SEQ ID NO:12). These extra amino acids are adjacent to and presumably removed with the transit peptide during targeting of the mutant soybean ALS protein to the plastid.

The cassette comprising a promoter and terminator separated by a unique Not I restriction endonuclease site comprises the KTi3 promoter, a unique Not I restriction endonuclease site, and the KTi3 terminator region. This cassette comprises about 2088 nucleotides of the KTi3 promoter, a unique Not I restriction endonuclease site, and about 202 nucleotides of the KTi3 transcription terminator. The gene encoding KTi3 has been described (Jofuku, K. D. and Goldberg, R. B., 1989, *Plant Cell* 1:1079-1093).

The second fragment, comprising the bacterial origin of replication and bacterial selectable marker gene was obtained by PCR amplification from plasmid pKS210 as follows. Plasmid pKS210 is derived from the commercially available cloning vector pSP72 (Promega, Madison, Wis.). To prepare plasmid pKS210 the beta lactamase coding region in vector pSP72 has been replaced by a hygromycin phosphotransferase (HPT) gene for use as a selectable marker in *E. coli*. SEQ ID NO:13 represents the nucleotide sequence of plasmid pKS210. A fragment of plasmid pKS210 comprising the bacterial origin of replication and HPT gene was amplified by PCR using oligonucleotide primers BM5 (SEQ ID NO:14) and BM6 (SEQ ID NO:15), and the Advantage High Fidelity polymerase (BD Biosciences, San Jose, Calif.) according to the manufacturer's instructions.

```
BM5:
5'-GCCGGGGTACCGGCGCGCCCGATCATCCGGAT    (SEQ ID NO:14)
ATAGTTCC-3'

BM6:
5'-GCCGGGGTACCGGCGCGCCGTTCTATAGTGTC    (SEQ ID NO:15)
ACCTAATC-3'
```

A GeneAmp PCR System 9700 machine (Applied Biosystems, Foster City, Calif.) machine was used and the resulting 2600 bp fragment was gel purified using the Qiagen Gel Purification System, digested with Kpn I and treated with Calf Intestinal Alkaline Phosphatase.

Figure 3:
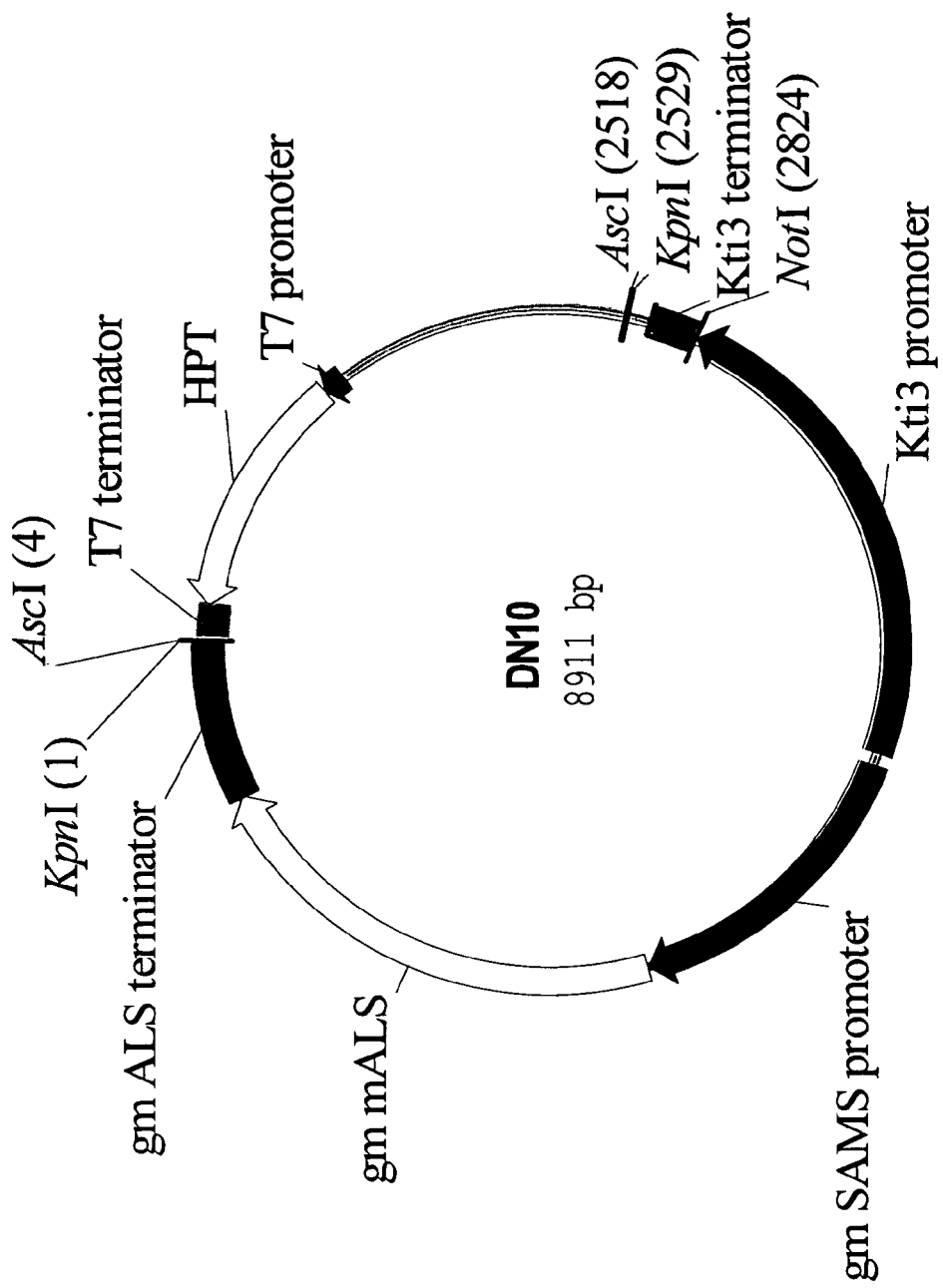
FIG. 3 depicts intermediate plasmid pDN10.

The two Kpn I fragments described above were ligated together and transformed into *E. coli*. Bacterial colonies were selected and grown overnight in LB media and appropriate antibiotic selection. DNA was isolated from the resulting culture using a Qiagen Miniprep Kit according to the manufacturer's protocol and then analyzed by restriction digest. DNA with the appropriate restriction pattern was named plasmid DN10, is depicted in FIG. 3, and SEQ ID NO:16 represents its nucleotide sequence.

C. Construction of Plasmid PHP20767

Plasmid PHP20767 was prepared by inserting nucleotides corresponding to the coding portion of the cDNA insert in clone src3c.pk024.m11 into the intermediate cloning vector pDN10. The coding portion of the cDNA clone src3c.pk024.m11 was amplified using primers BM7 (SEQ ID NO:17) and BM8 (SEQ ID NO:18) and using Advantage High Fidelity polymerase.

```
BM7:
5'-GCGGCCGCATGTGGAGGCTGAAGATAGCA      (SEQ ID NO:17)
G-3'

BM8:
5'-GCGGCCGCTTAAACTTCAGTGGAAGGCAAT      SEQ ID NO:18)
G-3'
```

The resulting amplification product was introduced into plasmid pCR2.1 using the TOPO TA Cloning Kit (Invitrogen) and SEQ ID NO:19 represents its nucleotide sequence. The resulting clone was completely sequenced using a mixture of external and internal primers and shown to correspond with the expected sequence.

Figure 4:
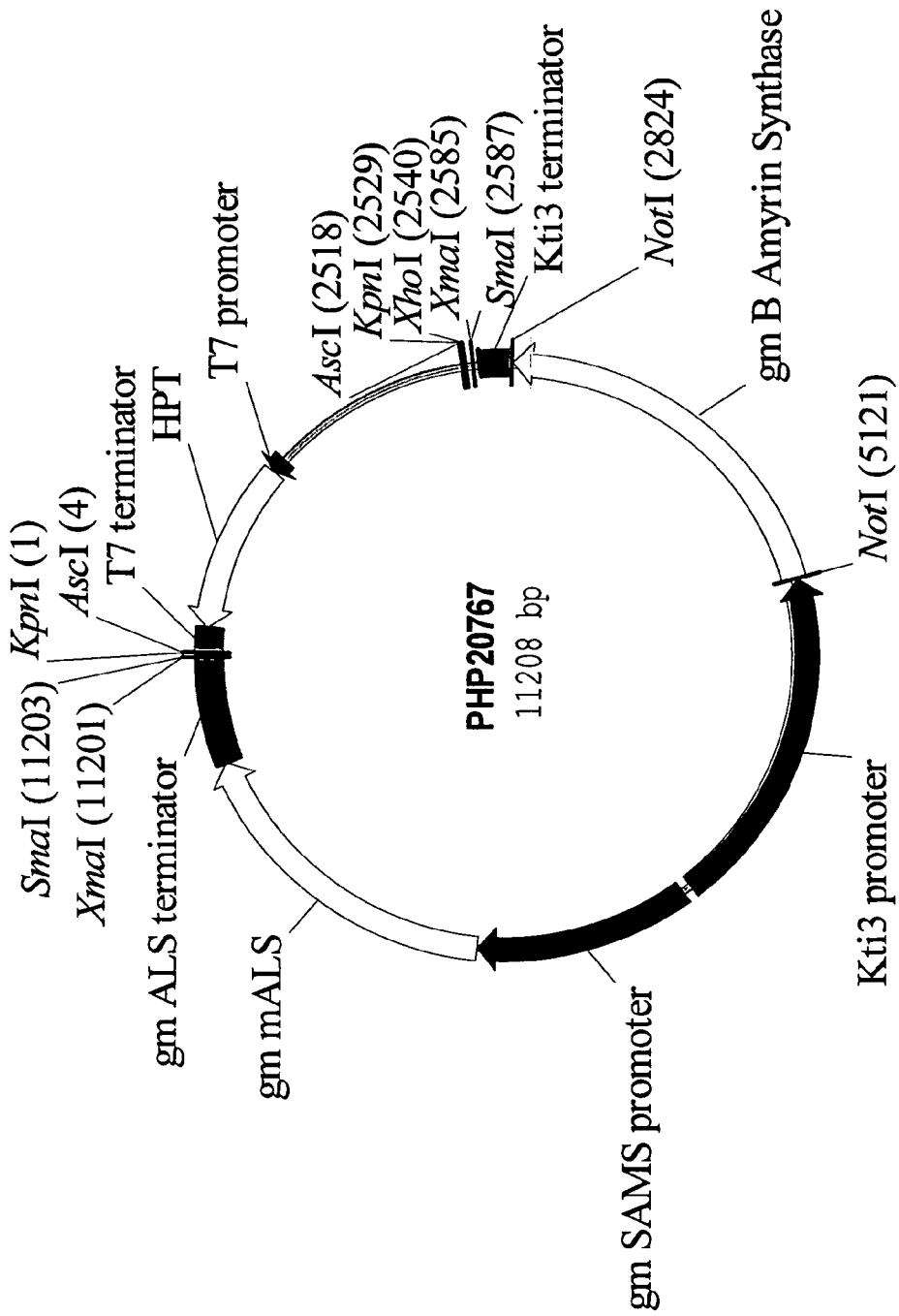
FIG. 4 depicts plasmid PHP20767.

The amplified product having the nucleotide sequence set forth in SEQ ID NO:19 was removed from plasmid pCR2.1 by restriction digestion with Not I and the resulting fragment was gel purified using Qiagen gel purification kit. Plasmid DN10 was digested with Not I, treated with Calf Intestinal Alkaline Phosphatase according to the manufacturer's instructions and the resulting 8911 bp fragment was gel purified using Qiagen gel purification kit. The two fragments were ligated together and transformed into *E. coli*. Bacterial colonies were selected and grown overnight in LB media and appropriate antibiotic selection. DNA was isolated from the resulting cultures using a Qiagen Miniprep Kit according to the manufacturer's protocol and then analyzed by restriction digest. DNA with the appropriate restriction pattern was named plasmid PHP20767 and SEQ ID NO:20 represents its nucleotide sequence. Plasmid PHP20767 is depicted in FIG. 4 and was used for transformation of somatic soybean embryo cultures as described in Example 2.

Construction of Plasmid PHP21157

Plasmid PHP21157 was prepared by inserting into the Not I site of plasmid DN10 (prepared as in B, above) a chimeric fragment comprising a portion of the cDNA insert in clone src3c.pk024.m11 and the isoflavone synthase (IFS) intron, and a fragment comprising the complement of the portion of the cDNA insert in clone src3c.pk024.m11. The cDNA insert in clone src3c.pk024.m11 has been described above. Polynucleotides encoding IFS, including a soybean genomic sequence and its intron has been described (PCT publication WO 00/44909 published 3 Aug., 2000; Jung, W. et al. (2000) Nat. Biotechnol. 18:208-212).

XXXA portion of the cDNA insert from clone src3c.pk024.m11 was amplified using primers BM9 (SEQ ID NO:21) and BM10 (SEQ ID NO:22). The intron from the isoflavone synthase genomic clone was amplified using primers BM11 (SEQ ID NO:23) and BM12 (SEQ ID NO:24). SEQ ID NO:25 represents the nucleotide sequence of the isoflavone synthase genomic clone used as a template. Primers BM10 and BM11 were designed in such a way that the amplification products of the two reactions hybridize to form a chimeric recombinant DNA fragment. A fresh amplification reaction was assembled using as template a mixture of product from each reaction and primers BM9 and BM12. All amplifications were carried out using the Advantage-GC cDNA PCR kit (Clontech, Palo Alto, Calif.) and a Perkin-Elmer Applied Biosystem GeneAmp PCR System 9700. The resulting amplification product was introduced into plasmid pCR2.1 using the TOPO TA Cloning Kit (Invitrogen) and in SEQ ID NO:26 represents its nucleotide sequence.

```
BM9:
5'-GCGGCCGCGAATTTTTTGCGGACATTG-3'     (SEQ ID NO:21)

BM10:
5'-GGAAACTTACGACATTAAACTTCAGTGGAA     (SEQ ID NO:22)
G-3'

BM11:
5'-CTTCCACTGAAGTTTAATGTCGTAAGTTTC     (SEQ ID NO:23)
C-3'

BM12:
5'-TAAGAAAAAGTCCTACATACCCAAAATTG-3'   (SEQ ID NO:24)
```

A portion of the cDNA insert from clone src3c.pk024.m11 was amplified using oligonucleotide primers BM13 (SEQ ID NO:27) and BM14 (SEQ ID NO:28). The resulting amplification product was introduced into plasmid pCR2.1 using the TOPO TA Cloning Kit (Invitrogen).

```
BM13:
5'-CTGCAGGGGTATGTAGGACTTTTTCTTAAACT   (SEQ ID NO:27)
TCAGTGGAAGGCAATG-3'

BM14:
5'-GCGGCCGCAATTTTTTGCGGACATTGTAGTTG   (SEQ ID NO:28)
AAC-3'
```

Figure 5:
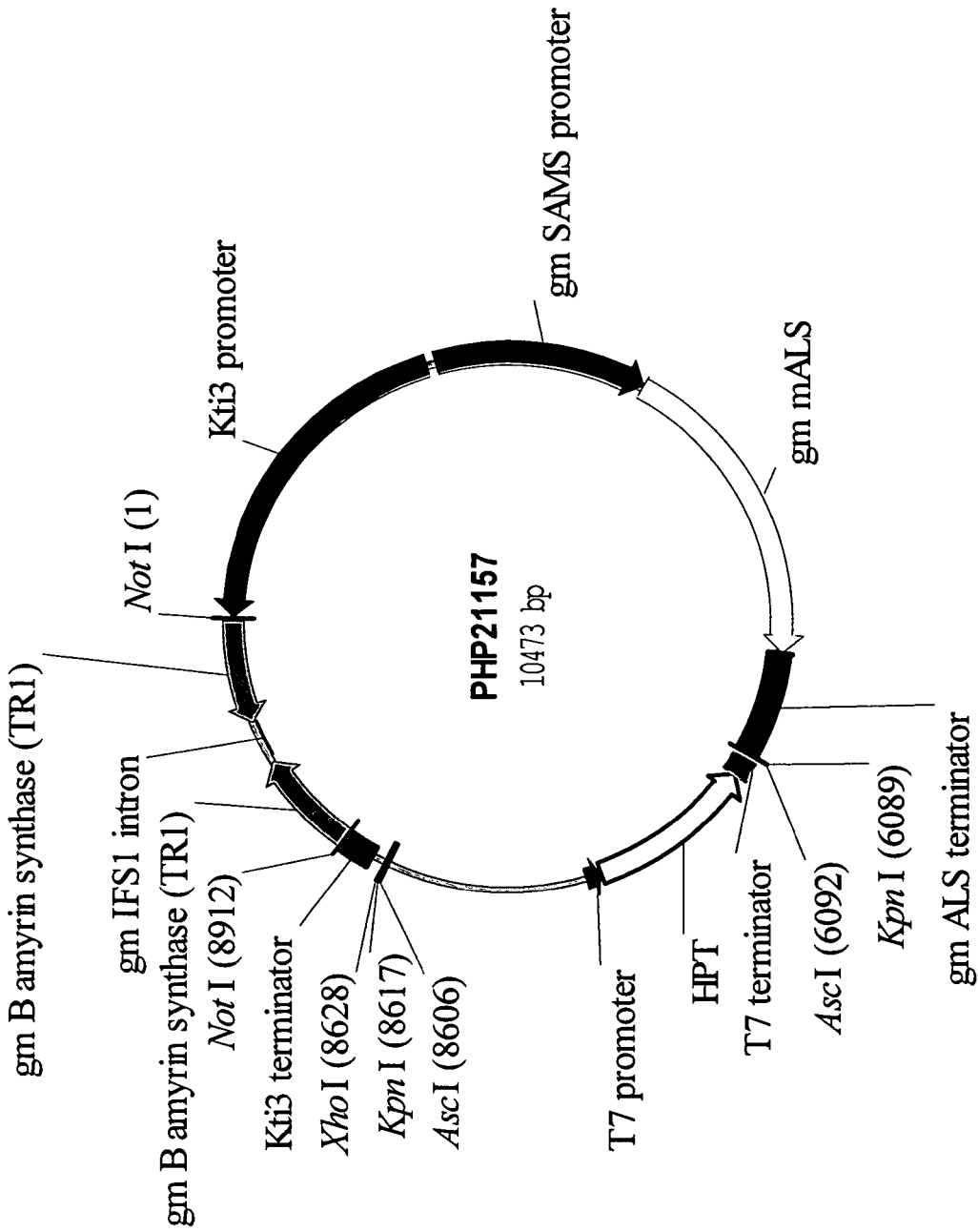
FIG. 5 depicts plasmid PHP21157.

The amplified product having the nucleotide sequence set forth in SEQ ID NO:26 was removed from plasmid pCR2.1 by restriction digestion with Not I and Pst I and the resulting fragment was gel purified using Qiagen gel purification kit. The amplified product having the nucleotide sequence represented in SEQ ID NO:29 was removed from plasmid pCR2.1 by restriction digestion with Not I and Pst I and the resulting fragment was gel purified using Qiagen gel purification kit. Plasmid DN10 was digested with Not I, treated with Calf Intestinal Alkaline Phosphatase according to the manufacturer's instructions and the resulting 8911 bp fragment was gel purified using Qiagen gel purification kit. The three fragments were ligated together and transformed into E. coli. Bacterial colonies were selected and grown overnight in LB media and appropriate antibiotic selection. DNA was isolated from the resulting culture using a Qiagen Miniprep Kit according to the manufacturer's protocol and then analyzed by restriction digest. DNA with the appropriate restriction pattern was named plasmid PHP21157 and in SEQ ID NO:30 represents its nucleotide sequence. Plasmid PHP21157 is depicted in FIG. 5 and was used for transformation of somatic soybean embryo cultures as described in Example 2.

Example 2

Transformation of Somatic Soybean (*Glycine max*) Embryo Cultures and Regeneration of Soybean Plants Soybean embryogenic suspension cultures were transformed by the method of particle gun bombardment using procedures known in the art (Klein et al. (1987) Nature (London) 327:70-73; U.S. Pat. No. 4,945,050; Hazel, et al. (1998) Plant Cell. Rep. 17:765-772; Samoylov, et al. (1998) In Vitro Cell Dev. Biol.-Plant 34:8-13). In particle gun bombardment procedures it is possible to use purified entire plasmid DNA or, purified DNA fragments containing only the recombinant DNA expression cassette(s) of interest.

The entire plasmid was used for transformations using plasmid AC18. The recombinant DNA fragments were isolated from plasmids PHP20767 and PHP21157 by digestion with restriction endonuclease Asc I and purified by gel electrophoresis before bombardment. SEQ ID NO:31 and SEQ ID NO:32 represent the nucleotide sequence of the recombinant DNA fragments obtained from plasmids PHP20767 and PHP21157 by digestion with Asc I and used for transformation. Gold particle/DNA suspensions sufficient for eight bombardments were prepared. Suspensions for transformation with plasmid AC18 contained 3 mg 0.6 mm gold particles and 5 pg plasmid DNA for every 40 µL suspension. Suspensions for transformation with the recombinant DNA fragments from plasmids PHP20767 and PHP21157 contained 3 mg of 0.6 mm gold particles and 1 to 90 picograms (pg) of base pair or DNA per fragment in a 40 µL suspension. The DNA/particle suspension was sonicated three times for one second each and 5 µL of the gold particle/DNA suspension were then loaded on each macro carrier disk.

Stock tissue for these transformation experiments were obtained by initiation from soybean immature seeds. Secondary embryos were excised from explants after 6 to 8 weeks on culture initiation medium. The initiation medium was an agar-solidified modified MS (Murashige and Skoog (1962) Physiol. Plant. 15:473497) medium supplemented with vitamins, 2,4-D and glucose. Secondary embryos were placed in flasks in liquid culture maintenance medium and maintained for 7-9 days on a gyratory shaker at 26 +/−2° C. under ~80 $\mu Em^{-2}s^{-1}$ light intensity. The culture maintenance medium was a modified MS medium supplemented with vitamins, 2,4-D, sucrose and asparagine. Prior to bombardment, clumps of tissue were removed from the flasks and moved to an empty 60×15 mm petri dish for bombardment. Tissue was dried by blotting on Whatman #2 filter paper. Approximately 100-200 mg of tissue corresponding to 10-20 clumps (1-5 mm in size each) were used per plate of bombarded tissue. After bombardment, tissue from each bombarded plate was divided and placed into two flasks of liquid culture maintenance medium per plate of bombarded tissue.

For transformation experiments using plasmid AC18 the liquid media was exchanged with fresh media five to seven days post bombardment, and eleven to twelve days post bombardment it was replaced with fresh media containing 50 mg/mL hygromycin. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures.

For transformation experiments using the recombinant DNA fragments from plasmids PHP20767 and PHP21157, seven days post bombardment, the liquid medium in each flask was replaced with fresh culture maintenance medium supplemented with 100 ng/mL selective agent (selection medium). For selection of transformed soybean cells the selective agent used was a sulfonylurea (SU) compound with the chemical name, 2-chloro-N-((4-methoxy-6 methyl-1,3,5-triazine-2-yl)aminocarbonyl) benzenesulfonamide (common names: DPX-W4189 and chlorsulfuron). Chlorsulfuron is the active ingredient in the DuPont sulfonylurea herbicide, GLEAN®. The selection medium containing SU was replaced every week for 6-8 weeks. After the 6-8 week selection period, islands of green, transformed tissue were observed growing from untransformed, necrotic embryogenic clusters. These putative transgenic events were isolated and kept in media with SU at 100 ng/mL for another 2-6 weeks with media changes every 1-2 weeks to generate new, clonally propagated, transformed embryogenic suspension cultures. Embryos spent a total of approximately 8-12 weeks in selection medium.

Suspension cultures were subcultured and maintained as clusters of immature embryos and also regenerated into whole plants by maturation and germination of individual somatic embryos.

Example 3

Analyses of Soyasaponegols in Transgenic Soybean Plants

The effect on the saponin content of the expression of the oxidosqualene cyclase recombinant DNA molecules in soybean plants was measured by analyzing the T1 seed obtained from soybean transgenic plants transformed with the previously described plasmids. Soyasapogenol A and soyasapogenol B content was calculated after removing the sugar moieties from saponins by acid hydrolysis and comparing to concentration curves prepared by HPLC/Mass Spec (LC/MS) of authentic standards. Because soyasapogenol A and soyasapogenol B are derived from saponins, their measurement provides a relative value for the amount of saponins present.

Transgenic soybean plants were analyzed as follows. Five to ten seeds per transformant were combined. Seeds from transformants obtained by bombarding with plasmid AC18 were ground using an Adsit grinder (Adsit Co., Inc., Ft. Meade, Fla.). Seeds from transformants obtained by bombarding with the recombinant DNA fragments from plasmids PHP20767 and PHP21157 were pulverized to a fine powder. About 100 mg ground soybean was accurately weighed into a microcentrifuge tube with screw cap, and a ¼ inch stainless steel bead was added along with 1 mL of 60% acetonitrile in water. The mixture was agitated on a Geno/Grinder™ Model 2000 (SPEX Certiprep, Metuchen, N.J.) for 1 minute with the machine set at 1500 strokes per minute and then placed on an end-over-end tumbler for 1 hour. The microcentrifuge tube was then placed in the Geno/Grinder™ for 1 minute with the machine set at 1500 strokes per minute. Samples were centrifuged at 12,000 rpm for 4 minutes and then the supernatant transferred to a 13×100 mm glass test tube fitted with a Teflon-lined® cap. The extraction procedure was repeated once and the supernatants combined into the same 13×100 mm glass test tube. To the tube containing the combined supernatants, 0.4 mL of 12N HCl was added when working with material obtained by bombarding with plasmid AC18 and 0.1 mL of 12N HCL was added when working with material obtained by bombarding with the recombinant DNA fragments from plasmids PHP20767 or PHP21157. After mixing, the tube was placed into an 80° C. heating block overnight (16 to 17 hours).

After overnight incubation, the tube was removed from the heating block and allowed to cool to room temperature. At that point, to the extracts derived from material obtained by bombarding with plasmid AC18, 0.5 mL of 30% ammonium hydroxide was added, the solution mixed, next, 2 mL of acetonitrile, 100 µL DMSO and 1.5 mL of methanol was added to the extracts and the solution mixed. To the extracts derived from material obtained by bombarding with the recombinant DNA fragments from plasmids PHP20767 or PHP21157, 5.0 mL of 12.5% methanol in acetonitrile were added and the solution mixed. The liquid in the tubes was sonicated for 10 minutes and the volume was measured and recorded. The tubes were centrifuged for 10 minutes at 3500 rpm at 20° C. and an aliquot of the supernatant was placed into an HPLC vial to analyze the soyasapogenols using LC/MS.

LC/MS was performed using a Waters™ (Waters Corp., Milford, Mass.) 2690 Alliance HPLC interfaced with a ThermoFinnigan (San Jose, Calif.) LCQ™ mass spectrometer. Samples were maintained at 25° C. (material obtained by bombarding with plasmid AC18) or 20° C. (material obtained by bombarding with the recombinant DNA fragments from plasmids PHP20767 or PHP21157) prior to injection. A 10 µL sample was injected onto a Phenomenex® (Torrance, Calif.) Luna™ C18 column (3µ, 4.6 mm×50 mm), equipped with a guard cartridge of the same material, and maintained at 40° C. Compounds were eluted from the column at a flow rate of 0.8 mL/minute using a solvent gradient. For the first two minutes the eluent was a 50/50 mixture of solvent A (0.1% formic acid in water) and solvent B (0.1% formic acid in acetonitrile). From 2 to 5 minutes the eluent was a linear gradient from 50% solvent B to 100% solvent B. From 5 to 8 minutes the eluent was 100% solvent B, and from 8 to 11 minutes the eluent was a 50/50 mixture of solvent A and solvent B. The mass spectrometer was equipped with an APCI source set to scan m/z of 250 to 500 in positive ion mode. The vaporizer temperature was set to 400° C., the capillary temperature was at 160° C. and the sheath gas flow was at 60 psi. Identification and quantification of soyasapogenol A and B was based on m/z and co-chromatography of authentic standards (Apin Chemicals, LTD, Oxon, UK or ChromaDex, Santa Ana, Calif.).

Example 4

Analyses of Phytosterols in Transgenic Soybean Plants

Soybeans from events transformed with plasmid AC18, or the recombinant DNA fragment from plasmid PHP20767 or PHP21157 and identified as having decreased levels of saponins based on sapogenol measurements were propagated. After harvest, seeds were analyzed again as described in Example 3 and seeds from lines that were shown to be lower in sapogenol levels were analyzed for phytosterols as described below.

Plants Transformed with plasmid AC18

Soybeans from events transformed with plasmid AC18 and identified as having decreased levels of saponins based on sapogenol measurements were propagated. After harvest, seeds were analyzed again as described in Example 3 and seeds from lines that were shown to be lower in sapogenol levels were combined and analyzed for phytosterols as described below.

The level of various phytosterols as well as cycloartenol was analyzed under the direction of Morgan Petty, Technical Manager of Woodson-Tenent Laboratories, A Division of Eurofins Scientific using AOAC 994.10. Briefly, soybean samples were ground and then were saponified using a potassium hydroxide solution and heat. The sterols were then extracted into toluene with shaking. An aliquot of the toluene was dried and the residue was dissolved in dimethylformamide. A portion of this solution was then derivatized to form trimethylsilyl ethers. These ethers were extracted into heptane containing an internal standard and injected onto a gas chromatograph with a capillary column and flame ionization detection for quantification. Results are shown in Table 1 where the amounts are shown as ppm.

TABLE 1

Sterol Content in Control and Decreased-Saponin Soybeans

| | Sterol Content (ppm) | |
|---|---|---|
| | Control | Low saponin |
| Sapogenol | 2000 | 300 |
| Cholesterol | <1 | <1 |
| Campesterol | 166 | 174 |
| Stigmasterol | 150 | 203 |
| Sitosterol | 480 | 1111 |
| Cycloartenol | 34 | 138 |
| Total sterols | 830 | 1626 |

This data shows that plants with decreased levels of saponins have an increased amount of total phytosterols. Control plants had more than 6 times as many saponins as plants transformed with plasmid AC18. Cholesterol levels were less than 1 ppm and campesterol levels were very similar in both cases. Stigmasterol levels were approximately 1.3 times higher, sitosterol levels were approximately 2.3 times higher, and cycloartenol levels were approximately 4 times higher in plants transformed with plasmid AC18 when compared to control plants. Total sterols were over 2 times higher in plants transformed with plasmid AC18 when compared to control plants.

B. Plants Transformed with the Recombinant DNA Fragment Isolated from Plasmid PHP20767

Soybeans from events transformed with the recombinant DNA fragment isolated from plasmid PHP20767 and identified as having decreased levels of saponins based on sapogenol measurements were propagated. After harvest seeds were analyzed again as described in Example 3 and seeds from putative homozygotes that were shown to be altered in sapogenol levels were analyzed for phytosterols as described below.

Eight to ten soybean seeds, from individual plants, were pulverized into a fine powder. A subsample of approximately 50 mg was accurately weighed into a 17×100 mm polypropylene tube and then 40 μL of cholestane (1 mg/mL acetone) were added with 2 mL of 10% (w/v) KOH in ethanol. Samples were sonicated for 10 minutes in a bath sonicator, on the highest power setting, at room temperature. Tubes were incubated at 60° C. for 1 hour with shaking and then cooled to room temperature. Two mL of water were added to each tube, contents mixed, and then partitioned against 4 mL of hexane. Tubes were centrifuged 2 minutes at 3500 rpm to facilitate phase separation and then the upper hexane phase removed and placed in a 13×100 mm glass tube. Partitioning of the lower phase against hexane was repeated twice more for a total of three times. The upper phases were combined with the first and then dried in a SpeedVac (Savant, Holbrook, N.Y.). Dried samples were dissolved in 1 mL acetone by sonicating 2 minutes and then transferred to GC vials after centrifugation at 3500 rpm for 10 minutes.

Samples were analyzed by Gas Chromatograph with a Flame Ionization Detector. The Gas Chromatograph was equipped with a DB-5MS capillary column that was 60 meters long, 250 pm ID with a 0.25 pm film thickness. The inlet was set to splitless mode and temperature of 300° C. The detector temperature was 320° C. The column oven was initially 220° C. and held at that temperature for the first minute after sample injection followed by an increase of 8° C./minute for the next 12.5 minutes and then held at 320° C. for 5 minutes for a total run time of 18.5 minutes. Hydrogen was the carrier gas at a flow rate of 2 mL/minute.

Results are shown in Table 2 where the amounts are shown as ppm. Soybean cultivar Jack was transformed with the recombinant DNA fragment isolated from plasmid PHP20767 and wild type Jack plants grown under similar conditions were analyzed as a control. As an additional control seeds of the cultivar 93B41 were also analyzed.

TABLE 2

Sterol and Saponin Content in Soybeans Transformed with the Recombinant DNA Fragment Isolated from Plasmid PHP20767

| EVENT | Campesterol | Stigmasterol | Sitosterol | Total Sterols | Soyasapogenol A + B/ |
|---|---|---|---|---|---|
| AFS 3786.5.7.1 | 174 | 184 | 563 | 920 | 5936 |
| AFS 3786.5.7.1 | 194 | 215 | 639 | 1049 | 6232 |
| AFS 3786.5.7.2 | 194 | 206 | 601 | 1001 | 5371 |
| AFS 3786.5.7.2 | 162 | 176 | 540 | 877 | 5560 |
| AFS 3786.8.5.1 | 211 | 199 | 764 | 1174 | 4861 |
| AFS 3786.8.5.2 | 210 | 199 | 721 | 1131 | 4692 |
| AFS 3788.1.2.1 | 208 | 199 | 743 | 1149 | 4518 |
| AFS 3792.5.1.1 | 245 | 242 | 1372 | 1859 | 87 |
| AFS 3792.5.1.1 | 235 | 249 | 1348 | 1831 | 95 |
| AFS 3792.5.1.1 | 272 | 235 | 1526 | 2034 | 82 |
| AFS 3792.5.1.1 | 296 | 262 | 1537 | 2095 | 90 |
| AFS 3792.5.1.1 | 254 | 268 | 1435 | 1957 | 63 |
| AFS 3792.5.1.2 | 240 | 241 | 1354 | 1835 | 94 |
| AFS 3792.5.1.2 | 203 | 283 | 1123 | 1609 | 93 |
| AFS 3792.5.1.2 | 248 | 246 | 1414 | 1908 | 93 |
| AFS 3792.5.1.2 | 246 | 277 | 1369 | 1893 | 329 |
| AFS 3792.5.5.1 | 222 | 237 | 1354 | 1813 | 90 |
| AFS 3792.5.5.1 | 196 | 207 | 1140 | 1542 | 78 |
| AFS 3792.7.2.1 | 140 | 215 | 791 | 1145 | 374 |
| AFS 3788.3.2.1 | 151 | 216 | 919 | 1285 | 298 |
| AFS 3792.7.2.2 | 180 | 233 | 1092 | 1505 | 79 |
| AFS 3792.1.5.1 | 181 | 248 | 1131 | 1560 | 80 |
| AFS 3792.1.5.1 | 176 | 254 | 1190 | 1620 | 59 |
| AFS 3792.1.5.1 | 199 | 257 | 1253 | 1710 | 52 |
| Jack | 215 | 200 | 722 | 1137 | 3252 |
| 93B41 | 209 | 196 | 650 | 1055 | 3083 |

The data in Table 2 shows that plants with decreased levels of saponins have an increased amount of total phytosterols.

Plants Transformed with the Recombinant DNA Fragment Isolated from Plasmid PHP21157

Soybeans from events transformed with recombinant DNA fragment in plasmid PHP21157 and identified as having decreased levels of saponins based on sapogenol measurements were propagated. After harvest, seeds were analyzed again as described in Example 3 and seeds from putative homozygotes that were shown to be lower in sapogenol levels were analyzed for phytosterols as described in Example 4B above.

Results are shown in Table 3 where the amounts are shown as ppm. Soybean cultivar Jack was transformed with the recombinant DNA fragment isolated from plasmid PHP20767 and wild type Jack plants grown under similar conditions were analyzed as a control. As an additional control seeds of the cultivar 93B41 were also analyzed.

TABLE 3

Sterol and Saponin Content in Soybeans Transformed with The Recombinant DNA Fragment Isolated From Plasmid PHP21157

| EVENT | Campesterol | Stigmasterol | Sitosterol | Total Sterols | Soyasapogenol A + B |
|---|---|---|---|---|---|
| AFS 3748.8.12.2 | 231 | 320 | 1425 | 1976 | 0 |
| AFS 3751.2.2.2 | 227 | 408 | 1303 | 1938 | 0 |
| AFS 3751.8.3.2 | 169 | 289 | 1197 | 1655 | 0 |
| AFS 3748.7.2.2 | 193 | 254 | 768 | 1215 | 4650 |
| AFS 3748.8.12.2 | 196 | 260 | 865 | 1321 | 4053 |
| AFS 3748.8.12.2 | 206 | 284 | 737 | 1228 | 4219 |
| AFS 3752.3.2.1 | 148 | 265 | 691 | 1104 | 2112 |
| AFS 3751.3.1.3 | 191 | 305 | 933 | 1430 | 1899 |
| Jack | 214 | 310 | 955 | 1479 | 2890 |
| 93B41 | 213 | 213 | 584 | 1010 | 2615 |

This data shows that plants with decreased levels of saponins have an creased amount of total phytosterols.

TABLE 4

Sequences Disclosed

| SEQ ID NO. | Name | Type |
|---|---|---|
| 1 | cDNA insert from clone sah1c.pk002.n23 | nucleotide |
| 2 | cDNA insert from clone src3c.pk024.m11 | nucleotide |
| 3 | expression vector Pks151 | nucleotide |
| 4 | 36 nucleotide sequence, two copies of which are found 5' of the Not I site in vector pKS151 | nucleotide |
| 5 | primer BM1 | nucleotide |
| 6 | primer BM2 | nucleotide |
| 7 | primer BM3 | nucleotide |
| 8 | primer BM4 | nucleotide |
| 9 | chimera comprising portions of the oxidosqualene cyclase genes found in clones sah1c.pk002.n23 and src3c.pk024.m11 | nucleotide |
| 10 | plasmid AC18 | nucleotide |
| 11 | 6383 bp fragment comprising a plant selectable marker gene expression cassette and a cassette comprising a promoter and terminator separated by a unique Not I restriction endonuclease site of the intermediate cloning vector pDN10 | nucleotide |
| 12 | mutant soybean ALS | polypeptide |
| 13 | plasmid pKS210 | nucleotide |
| 14 | primer BM5 | nucleotide |
| 15 | primer BM6 | nucleotide |
| 16 | plasmid pDN10 | nucleotide |
| 17 | primer BM7 | nucleotide |
| 18 | primer BM8 | nucleotide |
| 19 | insert in clone src3c.pk024.m11 amplified using oligonucleotide primers BM7 and BM8 | nucleotide |
| 20 | plasmid PHP20767 | nucleotide |
| 21 | primer BM9 | nucleotide |
| 22 | primer BM10 | nucleotide |
| 23 | primer BM11 | nucleotide |
| 24 | primer BM12 | nucleotide |
| 25 | IFS genomic clone | nucleotide |
| 26 | chimera comprising a portion of the of the cDNA insert in clone src3c.pk024.m11 and the IFS intron | nucleotide |
| 27 | primer BM13 | nucleotide |
| 28 | primer BM14 | nucleotide |
| 29 | complement of the portion of the cDNA insert in clone src3c.pk024.m11 used in preparing plasmid PHP21157 | nucleotide |
| 30 | plasmid PHP21157 | nucleotide |
| 31 | recombinant DNA fragment obtained from plasmid PHP20767 by digestion with Asc I | nucleotide |
| 32 | recombinant DNA fragment obtained from plasmid PHP21157 by digestion with Asc I | nucleotide |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

What is claimed is:

1. A method of producing a composition containing increased level of one or more phytosterols comprising processing a plant or portion thereof, wherein said plant comprises at least one recombinant DNA molecule, wherein expression of said recombinant DNA molecule is sufficient to decrease activity of a β-amyrin synthase and to increase production of a phytosterol as compared to a plant not comprising said recombinant DNA molecule, wherein the composition contains at least 1.5 times by weight as much of a phytosterol as a composition prepared from a plant not expressing said recombinant DNA molecule.

2. A method of producing a phytosterol-containing extract, wherein the extract contains an increased level of at least one phytosterol comprising:
   a) obtaining oil by processing a plant or portion thereof wherein said plant comprises at least one recombinant DNA molecule, wherein expression of said recombinant DNA molecule is sufficient to decrease the activity of a β-amyrin synthase and to increase production of a phytosterol as compared to a plant not comprising said recombinant DNA molecule; and
   b) extracting the phytosterol-containing extract from the oil of (a), wherein the extract contains at least 1.5 times by weight as much of a phytosterol as an extract prepared from a plant not expressing said recombinant DNA molecule.

3. A recombinant DNA molecule comprising:
   a) a portion of a β-amyrin synthase gene
   b) an intron, and
   c) an inverted repeat of a), wherein the intron is an isoflavone synthase intron.

4. A recombinant DNA molecule comprising:
   a) a portion of a β-amyrin synthase gene
   b) an intron, and
   c) an inverted repeat of a), wherein the recombinant DNA molecule comprises a nucleotide sequence of SEQ ID NO:32.

* * * * *